United States Patent [19]

Nomura et al.

[11] Patent Number: 5,554,615
[45] Date of Patent: Sep. 10, 1996

[54] CONDENSED PYRIMIDINE DERIVATIVE

[75] Inventors: Hiroaki Nomura; Toru Haneda; Yoshihiko Kotake; Norihiro Ueda; Kyosuke Kitoh, all of Ibaraki, Japan

[73] Assignee: Eisai Co., Ltd., Tokyo, Japan

[21] Appl. No.: 300,564

[22] Filed: Sep. 6, 1994

Related U.S. Application Data

[63] Continuation of Ser. No. 928,102, Aug. 11, 1992, abandoned.

[30] Foreign Application Priority Data

Aug. 21, 1991 [JP] Japan .................................... 3-209252
Sep. 30, 1991 [JP] Japan .................................... 3-251548

[51] Int. Cl.⁶ ...................... C07D 487/04; C07D 239/70; A61K 31/505
[52] U.S. Cl. .......................... 514/258; 544/253; 544/280
[58] Field of Search ............................. 544/280; 514/258

[56] References Cited

U.S. PATENT DOCUMENTS

| | | | |
|---|---|---|---|
| 4,997,838 | 3/1991 | Akimoto | 544/280 |
| 5,028,608 | 6/1991 | Taylor | 544/280 |
| 5,106,974 | 4/1992 | Akimoto | 544/280 |
| 5,354,754 | 10/1994 | Akimoto | 544/280 |
| 5,403,843 | 4/1995 | Akimoto | 544/280 |

FOREIGN PATENT DOCUMENTS 0438261  7/1991  European Pat. Off. .

OTHER PUBLICATIONS

Drugs of the Future 16, pp. 856–857 (1991).
Casper, Cancer 73, 766 (1993).
Schnur et al. J. Med. Chem. 34, 914–918 (1991).
Martin et al Cancer Research 46, 2189–2192 (1986).
Pazdur, ASCO Abstracts, #C–856 in Proceeding Am. Soc. Clin. OncDlogy 3, 219 (1984).
Paull, Arzheim–Forch/Drug Res. 34(II), 1984, pp. 1243–1246.
Estey, Cancer Treatment Reports 70, 1105–1115 (1986).
Goodman L. Gilman "The Pharmacological Basis of Therapeutics" 8th Edition (1990), pp. 1226–1227 (1989).
DeGraw Drugs of the Future 14, 849–851 (1989).

*Primary Examiner*—Mark L. Berch
*Attorney, Agent, or Firm*—Birch, Stewart, Kolasch & Birch, LLP

[57] ABSTRACT

A novel pyrimidine derivative having an excellent antitumor activity, which is represented by the following general formula (I) or a pharmacologically acceptable salt thereof:

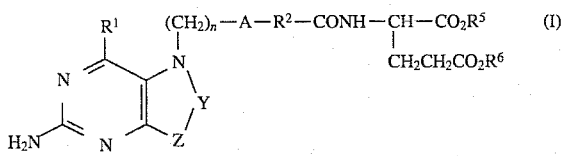

wherein $R^1$ represents a hydroxyl or amino group; $R^2$ represents a phenylene, pyridinediyl, thiendiyl, furandiyl or thiazoldiyl group, $—CO_2R^5$ and $—CO_2R^6$ may be the same or different from each other and each represents a carboxyl group or a carboxylic acid ester, the part

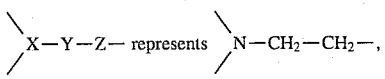

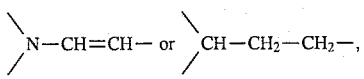

A represents an oxygen atom, a group represented by the formula:

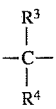

(wherein $R^3$ and $R^4$ may be the same or different from each other and each represents a hydrogen or halogen atom or a hydrocarbon group which may be substituted, or alternatively $R^3$ and $R^4$ may be united to form an alkylidene group which may be substituted) or a group represented by the formula:

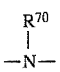

(wherein $R^{70}$ represents a hydrogen atom or a hydrocarbon group), and n is an integer of 1 to 3, provided that the compound in which $R^1$ represents oxygen, and hydrogen is attached to nitrogen at 3-position is included in the above shown definition, a process for preparation the same, and an antitumor drug containing the same.

26 Claims, No Drawings

CONDENSED PYRIMIDINE DERIVATIVE

This application is a continuation of application Ser. No. 07/928,102 filed on Aug. 11, 1992, now abandoned.

FIELD OF THE INVENTION

The present invention relates to novel heterocyclic compounds fused with a pyrimidine ring (hereinafter abbreviated to condensed pyrimidine derivatives) such as a pyrrolo[3,2-d]pyrimidine and a 6,7-dihydro-5H-cyclopenta[d]-pyrimidine which are useful as as antitumor agents, and to a production process thereof.

DESCRIPTION OF THE RELATED ART

Methotrexate (hereinafter abbreviated to "MTX") is a folic acid antagonist and has been developed as an antitumor agent. Since its introduction in the early 1950s, it continues to take a clinically important position. MTX is used by itself mainly in the treatment of choriocarcinoma, osteosarcoma and acute lymphocytic leukemia, chronic lymphocytic leukemia and, in addition, the range of its therapeutic application is being gradually widened by the concomitant use of other antitumor drugs or the development of a new administration method. MTX exhibits a high inhibitory activity against dihydrofolate reductase (DHFR). However, DHFR is present in both tumoral and normal tissues, so that MTX exerts an influence on both of them. In fact, MTX causes potent adverse effects such as bone marrow suppression and degradation of the intestinal epithelium, which limits the clinical application thereof. Further, MTX is rather narrow in the therapeutic spectrum and effect on solid tumors.

Furthermore, the therapeutic effect of MTX drastically decreased with the development of resistance to this drug by tumor cells which occured after the repeated MTX treatment for a certain period. These defective properties of MTX limit the scope of its therapeutic applicaiton and lower the clinical usefulness thereof.

In the last 40 yeas, over several hundred folic acid analogs have been synthesized, and biochemically and pharmacologically tested. These compounds were examined for inhibitory activity against folate-dependent enzymes and tumor cell growth and tested for therapeutic effect on tumor bearing mice. A great quantity of biochemical and pharmacological data accumulated with these analogs provided much information on both structure-activity and structure-toxicity relationships. A comprehensive account of these results have been given by many papers and review, e.g., Chemistry and Biology of Pteridines 1989, Ed. by H. Ch. Curtius, S. Ghisla, N. Blau. Walter de Gruyter, Berlin, New York 1990; Progress in Medicinal Chemistry, vol. 26, pp. 1 to 252(1989), Elsevier Science Publishers.)

In considering the chemical modification, the molecular structure of folic acid may be conveniently dissected into four moieties, i.e., heterocycle, bridge, benzoic acid and amino acid moieties. The primary structrural feature of such folic acid analogs resides in the heterocycle moiety. In fact, an overwhelming number of folic acid antagonists have been known so far which possess a hereto bicycle comprising two 6-membered rings fused with each other, as exemplified by a pteridine ring or a related 6-6 fused heterocyclic ring.

In relatively recent years, reports have been made of folic acid analogs possessing various deazapteridine ring such as 5-deazapteridine, 8-deazapteridine, 10-deazapteridine, 5,8-dideazapteridine, and their dihydro-and 5,6,7,8-tetrahydrodeazapteridines. DHFR inhibitors, MTX and 10-ethyl-10-deazaaminopterin (10-EDAM) [K. Y. Shum et al., J. Clinical Oncology, 6(3), 446–450(1988)] which possess a pteridine ring; thymidylate synthetase inhibitors, $N^{10}$-propagyl-5,8-dideazafolic Acid (CB3717) [A. H. Calvert et al., J. Clinical Oncology, 4(8), 1245–52(1986)] and N-[5-[N-(3,4-Dihydro-2-methyl-4 -oxoquinazolin-6-ylmethyl)-N-methylamino]-2-thenoyl]-L-glutamic Acid) (D1694) [A. L. Jackman et al., Cancer Research, 51, 5579–86(1991)] which have a 5,8-dideazapteridine ring; and a glycinamide ribonucleotide transformylase inhibitor, 5,10-Dideaza- 5,6, 7,8-tetrahydrofolate (DDATHF) [E. C. Taylor et al., J. Med. Chem., 28, 914–921(1985)] which has 5-deaza- 5,6,7,8-tetrahydropteridine ring fall under such category (analogs with a condensed 6-membered heterocyclic ring).

On the other hand, only a few analogs having a heterobicycle system comprising a 6- and a 5-membered ring fused with each other have been known to this time. As one such example, 2,4-diaminopurine-based antifolate, a folic acid analog possessing a purine ring in place of the pterindine ring, is described in L. T. Weinstock, Journal of Medicinal Chemistry, 13, 995 (1970) and shown to be entirely devoid of inhibitory activity against both folate relating enzymes and L1210 leukemia. Another example is concerned with pyrrolo[2,3-d]pyrimidne-based antifolates with the structure shown below. This class of compounds has been described by Miwa et al. in Journal of Medicinal Chemistry, 34, 55 to 560(1991). These compounds showed the property as a folate antagonist and potent inhibitory effects on tumor cell proliferation. However, the clinical applicability thereof has not been clarified as yet.

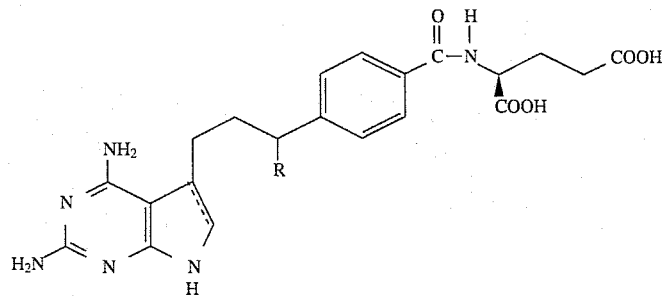

wherein R represents a hydrogen atom or a methyl group; and the symbol ----- represents a single or double bond.

European Patent Publication No. 0438261-A2 (Jul. 24, 1991) discloses condensed heterocycles bonded to a glutamic acid derivative which are useful as an antitumor agent.

Notwithstanding the recent scientific progress made in this field as described above, no antifolate has yet been put into clinical practice, since MTX made its debut. Furher, as to the antifolates under investigation, it is difficult to attain a satisfactory level and they appear to be limited by their relatively narrow antitumor spectra, the development of drug resistance and their adverse reactions when treating cancer patients. Accordingly, it has been earnestly desired in the field of cancer chemotherapy To create and develop anticancer antifolates which are therapeutically much improved and can work through highly selective toxicity against tumor tisssues.

SUMMARY OF THE INVENTION

The present invention aims at providing a novel condensed pyrimidine derivative exhibiting an excellent antitumor activity. Further, it also aims at providing a process for the preparation of the same and a drug composition containing the same as an active ingredient.

The present inventors have extensively studied to solve the above problems and have found that condensed pyrimidine derivatives are novel and useful as an antitumor drug. The present invention has been accomplished on the basis of this finding.

The present invention provides a pyrimidine derivative, i.e., a pyrimidine fused a five-membered ring, represented by the following general formula (I) or a pharmacologically acceptable salt thereof:

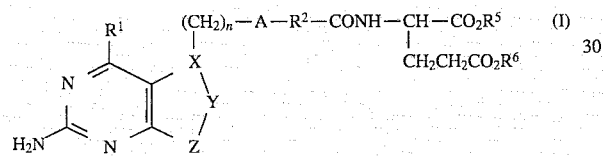

wherein $R^1$ represents a hydroxyl or amino group; $R^2$ represents a phenylene, pyridinediyl, thiendiyl, furandiyl or thiazoldiyl group; $—CO_2R^5$ and $—CO_2R^5$ may be the same or different from each other and each represents a carboxyl group or carboxylic acid ester; the part

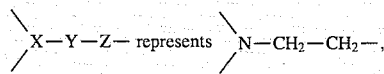 represents 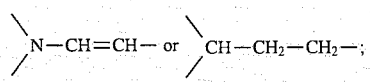, $$\diagdown_{N—CH=CH—} \text{ or } \diagdown_{CH—CH_2—CH_2—};$$

A represents an oxygen atom, a group represented by the formula:

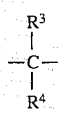

(wherein $R^3$ and $R^4$ may be the same or different from each other and each represent a hydrogen or halogen atom or a hydrocarbon group which may be substituted, or alternatively $R^3$ and $R^4$ may be united to form an alkylidene group which may be substituted) or a group represented by the formula:

(wherein $R^{70}$ represents a hydrogen atom or a hydrocarbon group); and n is an integer of 1 to 3, provided that the compound in which $R^1$ represents oxygen, and hydrogen is attached to nitrogen at 3-position is included in the definition shown above based on keto-enol tautomerism.

The present invention includes the following pyrimidine derivatives and pharmacologically acceptable salts thereof:

(1) one which $R^1$ in the general formula (I) is an amino group.

(2) one which $R^1$ in the general formula (I) is a hydroxyl group.

(3) one which $R^2$ in the general formula (I) is a phenylene group.

(4) one which $R^2$ in the general formula (I) is a pyridinediyl group.

(5) one which $R^2$ in the general formula (I) is a thiendiyl group.

(6) one which $R^2$ in the general formula (I) is a furandiyl group.

(7) one which $R^2$ in the general formula (I) is a thiazoldiyl group.

(8) one which the part

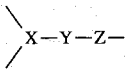

in the general formula (I) is

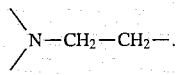

(9) one which the part

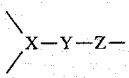

in the general formula (I) is

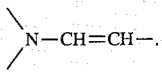

(10) one which the part

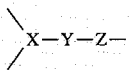

in the general formula (I) is

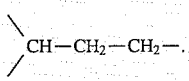

(11) one which A in the general formula (I) is a group represented by the formula:

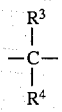

(wherein $R^3$ and $R^4$ may be the same or different from each other and each represents a hydrogen or halogen atom or a lower alkyl, lower alkenyl or lower alkynyl group, or alternatively $R^3$ and $R^4$ may be united to form an alkylidene group which may be substituted).

(12) one which A in the general formula (I) is a group represented by the formula:

(wherein $R^{70}$ represents a hydrogen atom or a hydrocarbon group).

(13) one which in the general formula (I), $R^1$ is an amino group and $R^2$ is a phenylene group.

(14) one which in the general formula (I), $R^1$ is an amino group and $R^2$ is a thiendiyl group.

(15) one which in the general formula (I), $R^1$ is a hydroxyl group and $R^2$ is a phenylene group.

(16) one which in the general formula (I), $R^1$ is a hydroxyl group and $R^2$ is a thiendiyl group.

(17) one which in the general formula (I), $R^1$ is an amino group, A is a methylene group and n is 1.

(18) one which in the general formula (I), $R^1$ is a hydroxyl group, A is a methylene group and n is 1.

(19) one which in the general formula (I), the part

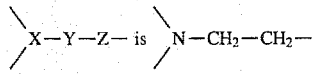

and $R^2$ is a phenylene group.

(20) one which in the general formula (I), the part

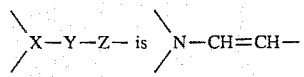

and $R^2$ is a phenylene group.

(21) one which in the general formula (I), the part

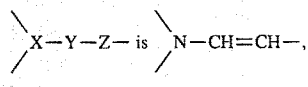

$R^1$ is an amino group and $R^2$ is a phenylene group.

(22) one which in the general formula (I), the part

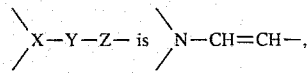

$R^2$ is a phenylene group and A is

(23) one which in the general formula (I), the part

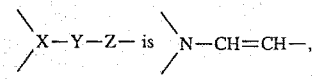

$R^2$ is a phenylene group and A is

(24) one which in the general formula (I), the part

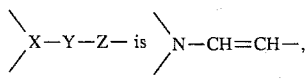

$R^1$ is an amino group, $R^2$ is a phenylene group, $R^5$ and $R^6$ are each a hydrogen atom, n is 1, and A is

(25) one which in the general formula (I), $R^2$ represents a phenylene, pyridinediyl, thiendiyl or furandiyl group, $R^5$ and $R^6$ are each a hydrogen atom, the part

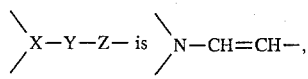

and A is a group represented by the formula:

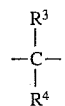

(wherein $R^3$ and $R^4$ may be the same or different from each other and each represent a hydrogen or halogen atom or a hydrocarbon group, or alternatively $R^3$ and $R^4$ may be united to form an alkylidene group which may be substituted).

(26) one which in the general formula (I), $R^2$ represents a phenylene, pyridinediyl, thiendiyl or furandiyl group, $R^5$ and $R^6$ are each a hydrogen atom, the part

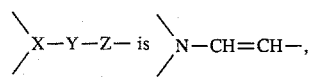

A is a group represented by the formula:

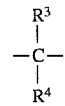

(wherein $R^3$ and $R^4$ may be the same or different from each other and each represent a hydrogen or halogen atom or a hydrocarbon group, or alternatively $R^3$ and $R^4$ may be united to form an alkylidene group which may be substituted), and $R^1$ is an amino group.

(27) one which in the general formula (I), $R^2$ represents a phenylene, pyridinediyl, thiendiyl or furandiyl group, $R^5$ and $R^6$ are each a hydrogen atom, the part

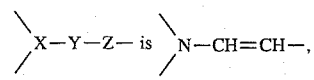

A is a group represented by the formula:

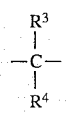

(wherein $R^3$ and $R^4$ may be the same or different from each other and each represent a hydrogen or halogen atom or a hydrocarbon group, or alternatively $R^3$ and $R^4$ may be united to form an alkylidene group which may be substituted), and $R^1$ is a hydroxyl group.

(28) one which in the general formula (I), $R^2$ is a phenylene group, $R^5$ and $R^6$ are each a hydrogen atom, the part

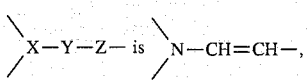

and A is a group represented by the formula:

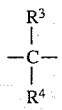

(wherein $R^3$ and $R^4$ may be the same or different from each other and each represent a hydrogen or halogen atom or a hydrocarbon group, or alternatively $R^3$ and $R^4$ may be united to form an alkylidene group which may be substituted).

(29) one which in the general formula (I), $R^2$ is a thiendiyl group, $R^5$ and $R^6$ are each a hydrogen atom, the part

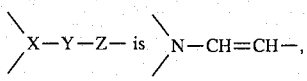

and A is a group represented by the formula:

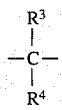

(wherein $R^3$ and $R^4$ may be the same or different from each other and each represent a hydrogen or halogen atom or a hydrocarbon group, or alternatively $R^3$ and $R^4$ may be united to form an alkylidene group which may be substituted).

(30) one which in the general formula (I), $R^2$ represents a phenylene, pyridinediyl, thiendiyl or furandiyl group, $R^5$ and $R^6$ are each a hydrogen atom, the part

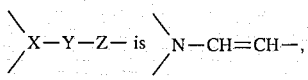

and A is a group represented by the formula:

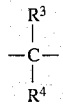

(wherein $R^3$ and $R^4$ may be the same or different from each other and each represent a hydrogen or halogen atom or a lower alkyl, lower alkenyl or lower alkynyl group).

(31) one which in the general formula (I), $R^2$ represents a phenylene, pyridinediyl, thiendiyl or furandiyl group, $R^5$ and $R^6$ are each a hydrogen atom, the part

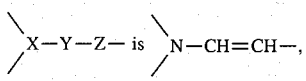

A is a group represented by the formula:

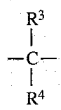

(wherein $R^3$ and $R^4$ may be the same or different from each other and each represent a hydrogen or halogen atom or a hydrocarbon group, or alternatively $R^3$ and $R^4$ may be united to form an alkylidene group which may be substituted), and n is 1.

(32) one which in the general formula (I), $R^2$ represents a phenylene, pyridinediyl, thiendiyl or furandiyl group, $R^5$ and $R^6$ are each a hydrogen atom, the part

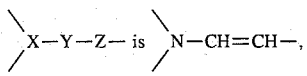

A is a group represented by the formula:

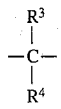

(wherein $R^3$ and $R^4$ may be the same or different from each other and each represent a hydrogen or halogen atom or a hydrocarbon group, or alternatively $R^3$ and $R^4$ may be united to form an alkylidene group which may be substituted), and n is 2.

(33) one which in the general formula (I), the part

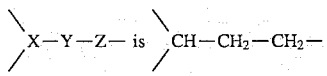

and $R^1$ is an amino group.

(34) one which in the general formula (I), the part

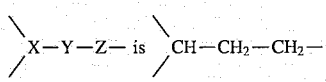

$R^1$ is an amino group, and $R^2$ is a phenylene group.

(35) one which in the general formula (I), the part

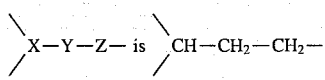

$R^1$ is an amino group, and $R^2$ is a thiendiyl group.

(36) one which in the general formula (I), the part

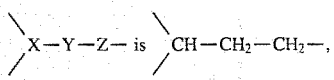

$R^2$ is a phenylene group, and A is —NH—.

(37) one which in the general formula (I), the part

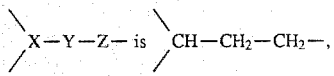

$R^2$ is a phenylene group, and A is

(38) one which in the general formula (I), the part

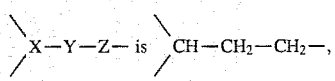

$R^5$ and $R^6$ are each a hydrogen atom, and A is a group represented by the formula:

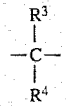

(wherein $R^3$ and $R^4$ may be the same or different from each other and each represent a hydrogen or halogen atom or a hydrocarbon group which may be substituted).

(39) one which in the general formula (I), the part

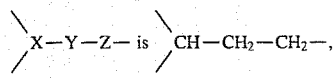

$R^1$ is an amino group, $R^2$ is a phenylene group, $R^5$ and $R^6$ are each a hydrogen atom, A is a methylene group and n is 2.

(40) one which in the general formula (I), the part

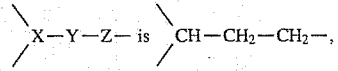

$R^1$ is an amino group, $R^2$ is a thiendiyl group, $R^5$ and $R^6$ are each a hydrogen atom, A is a methylene group, and n is 2.

(41) one which in the general formula (I), the part

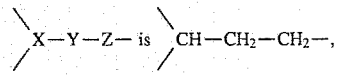

$R^1$ is an amino group, $R^2$ is a phenylene group, $R^5$ and $R^6$ are each a hydrogen atom, A is

and n is 2.

(42) one which in the general formula (I), the part

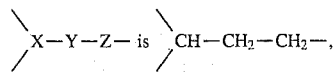

$R^1$ is an amino group, $R^2$ is a phenylene group; $R^5$ and $R^6$ are each a hydrogen atom, A is

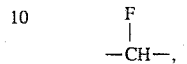

and n is 2.

(43) A pyrrolo[3,2-d]pyrimidine derivative represented by the following general formula (1) or a pharmacologically acceptable salt thereof:

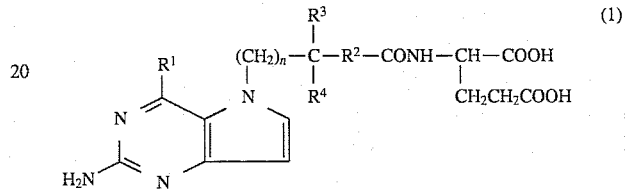

wherein $R^1$ represents a hydroxyl or amino group, preferably an amino group; $R^2$ represents a phenylene group or a group represented by the formula:

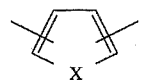

(wherein X represents a sulfur or oxygen atom), preferably a phenylene or thiendiyl group; $R^3$ and $R^4$ may be the same or different from each other and each represent a hydrogen atom or a hydrocarbon group, or alternatively they may be united to form an alkylidene group, preferably each a hydrogen atom or a lower alkyl, lower alkenyl or lower alkynyl group; and n is an integer of 1 to 3, preferably 1 or 2, still preferably 2.

(44) A 6,7-dihydro-5H-cyclopenta[d]pyrimidine derivative represented by the following general formula (101) or a pharmaceutically acceptable salt thereof:

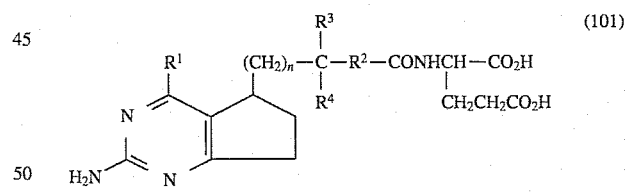

wherein $R^1$ represents a hydroxyl or amino group, $R^2$ represents a phenylene, thiendiyl, furandiyl or thiazoldiyl group, $R^3$ and $R^4$ may be the same or different from each other and each represent a hydrogen atom or a hydrocarbon group which may be substituted, and n is an integer of 1 to 3.

The present invention also provides a compound represented by the following general formula (II) or a salt thereof:

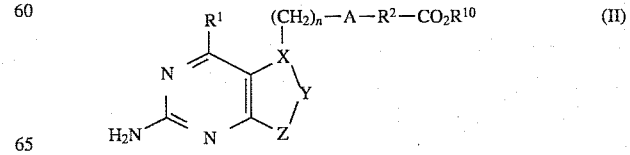

wherein $R^1$ represents a hydroxyl or amino group, $R^2$ represents a phenylene, pyridinediyl, thiendiyl, furandiyl or thiazoldiyl group, —$CO_2R^{10}$ represents a carboxyl group or a carboxylic acid ester, the part

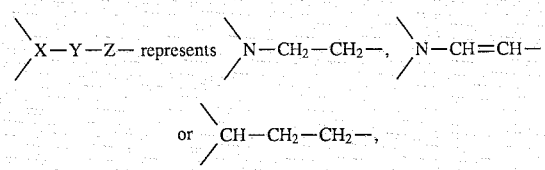

A represents an oxygen atom, a group represented by the formula:

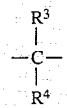

(wherein $R^3$ and $R^4$ may be the same or different from each other and each represent a hydrogen or halogen atom or a hydrocarbon group which may be substituted, or alternatively $R^3$ and $R^4$ may be united to form an alkylidene group which may be substituted) or a group represented by the formula:

(wherein $R^{70}$ represents a hydrogen atom or a hydrocarbon group), and n is an integer of 1 to 3, provided that the compound in which $R^1$ represents oxygen, and hydrogen is attached to nitrogen at 3-position is included in the above shown definition.

The present invention includes the following compounds and salts thereof:

(1) one which in the general formula (II), the part

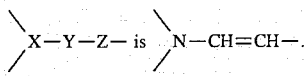

(2) one which in the general formula (II), the part

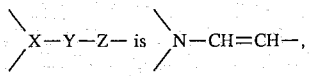

$R^2$ represents a phenylene, pyridinediyl, thiendiyl or furandiyl group, and A is a a group represented by the formula:

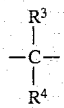

(wherein $R^3$ and $R^4$ may be the same or different from each other and each represent a hydrogen or halogen atom or a hydrocarbon group, or alternatively $R^3$ and $R^4$ may be united to form an alkylidene group).

(3) one which in the general formula (II), the part

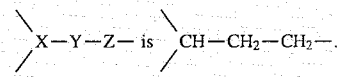

(4) one which in the general formula (II), the part

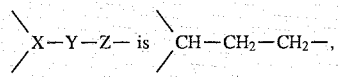

A is a group represented by the formula:

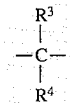

(wherein $R^3$ and $R^4$ may be the same or different from each other and each represent a hydrogen or halogen atom or a hydrocarbon group which may be substituted).

(5) one represented by the following general formula (4) or a salt thereof:

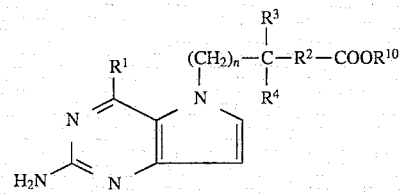

wherein $R^1$ represents a hydroxyl or amino group, $R^2$ represents a phenylene group or a group represented by the formula:

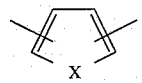

(wherein X represents a sulfur or oxygen atom), $R^3$ and $R^4$ may be the same or different from each other and each represent a hydrogen atom or a hydrocarbon group, or alternatively they may be united to form an alkylidene group, n is an integer of 1 to 3, and —$COOR^{10}$ represents a carboxyl group or a carboxylic acid ester.

(6) one represented by the following general formula (105) or a salt thereof:

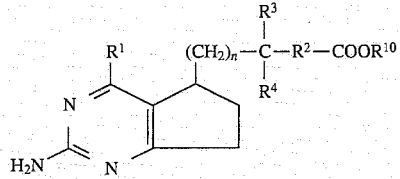

wherein $R^1$ represents a hydroxyl or amino group, $R^2$ represents a phenylene, thiendiyl, furandiyl or thiazoldiyl group, $R^3$ and $R^4$ may be the same or different from each other and each represent a hydrogen atom or a hydrocarbon group which may be substituted, n is an integer of 1 to 3, and —$COON^{10}$ represents a carboxyl group or a carboxylic acid ester.

The present invention provides a process for the preparation of a pyrimidine derivative represented by the above general formula (I) or a pharmacologically acceptable salt thereof, which comprises reacting a compound represented by the following general formula (III):

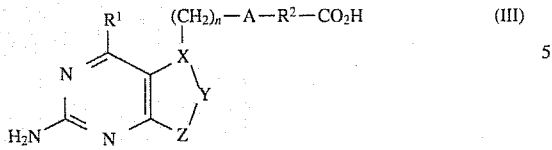 (III)

wherein $R^1$ represents a hydroxyl or amino group, $R^2$ represents a phenylene, pyridinediyl, thiendiyl, furandiyl or thiazoldiyl group, the part

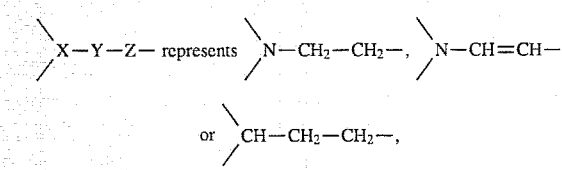

A represents an oxygen atom, a group represented by the formula:

(wherein $R^3$ and $R^4$ may be the same or different from each other and each represent a hydrogen or halogen atom or a hydrocarbon group which may be substituted, or alternatively $R^3$ and $R^4$ may be united to form an alkylidene group which may be substituted) or a group represented by the formula:

(wherein $R^{70}$ represents a hydrogen atom or a hydrocarbon group), and n is an integer of 1 to 3, provided that the compound in which $R^1$ represents oxygen, and hydrogen is attached to nitrogen at 3-position is included in the above shown definition, or a reactive derivative thereof wherein the carboxyl group is modified to a reactive form, with a compound represented by the following general formula (IV):

 (IV)

wherein $—CO_2R^5$ and $—CO_2R^6$ may be the same or different from each other and each represent a carboxyl group or a carboxylic acid ester.

The present invention includes the following processes:

(1) A process which in the above-described process, the compound represented by the general formula (III) is a compound selected from the group consisting of those which are represented by the general formula (III) provided that the part

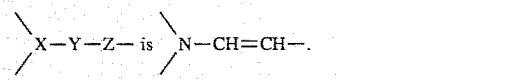

(2) A process which in the above-described process, the compound represented by the general formula (III) is a compound selected from the group consisting of those which are represented by the general formula (III) provided that $R^2$ represents a phenylene, pyridinediyl, thiendiyl or furandiyl group, the part

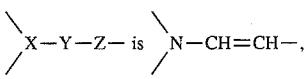

A is a group represented by the formula:

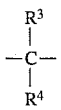

(wherein $R^3$ and $R^4$ may be the same or different from each other and each represent a hydrogen or halogen atom or a hydrocarbon group, or alternatively $R^3$ and $R^4$ may be united to form an alkylidene group).

(3) A process which in the above-described process, the compound represented by the general formula (III) is a compound selected from the group consisting of those which are represented by the general formula (III) provided that the part

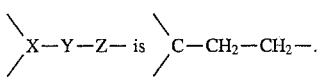

(4) A process for the preparation of a pyrimidine derivative or a pharmacologically acceptable salt thereof, which comprises reacting a compound represented by the following general formula (V):

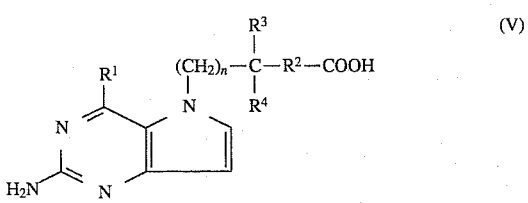 (V)

wherein $R^1$ represents a hydroxyl or amino group, $R^2$ represents a phenylene, pyridinediyl, thiendiyl. furandiyl or thiazoldiyl group, $R^3$ and $R^4$ may be the same or different from each other and each represent a hydrogen or halogen atom or a hydrocarbon group which may be substituted, and n is an integer of 1 to 3, provided that the compound in which $R^1$ represents oxygen, and hydrogen is attached to nitrogen at 3-position is included in the above shown definition, or a reactive derivative thereof wherein the carboxyl group is modified to a reactive form, with a compound represented by the following general formula (IV):

 (IV)

wherein $—CO_2R^5$ and $—CO_2R^6$ may be the same or different from each other and each represent a carboxyl group or a carboxylic acid ester, provided that one or both of $—CO_2R^5$ and $—CO_2R^6$ represent a carboxyl group which is esterified, to form a carboxylic ester represented by the following general formula (VI):

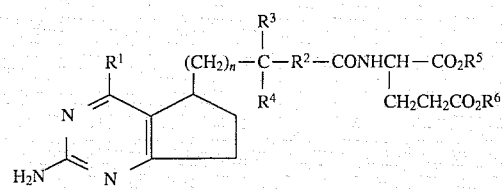

(VI)

wherein R¹ represents a hydroxyl or amino group, R² represents a phenylene, pyridinediyl, thiendiyl, furandiyl or thiazoldiyl group, R³ and R⁴ may be the same or different from each other and each represent a hydrogen or halogen atom or a hydrocarbon group which may be substituted, —CO₂R⁵ and —CO₂R⁶ may be the same or different from each other and each represents a carboxyl group or a carboxylic acid ester provided that one or both of —CO₂R⁵ and —CO₂R⁶ represent a carboxylic acid ester, and n is an integer of 1 to 3, provided that the compound in which R¹ represents oxygen, and hydrogen is attached to nitrogen at 3-position is included in the above shown definition, and converting the ester into a free carboxylic acid derivative through acidic or alkaline hydrolysis or hydrogenolysis including catalytic reduction.

(5) A process for the preparation of the pyrrolo[3,2-d]pyrimidine derivative represented by the general formula (1) or pharmacologically acceptable salt thereof, which comprises reacting a compound represented by the following general formula (2):

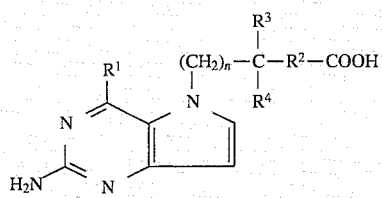

(2)

wherein R¹ represents a hydroxyl or amino group, R² represents a phenylene group or a group represented by the formula:

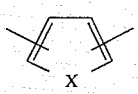

(wherein X represents a sulfur or oxygen atom), R³ and R⁴ may be the same or different from each other and each represent a hydrogen atom or a hydrocarbon group, or alternatively they may be united to form an alkylidene group, and n is an integer of 1 to 3, or a reactive derivative thereof wherein the carboxyl group is modified to a reactive form, with a compound represented by the following general formula (3):

(3)

wherein R⁵ and R⁶ may be the same or different from each other and each represent a carboxyl-protective group.

(6) A process for the preparation of a 6,7-dihydro-5H-penta[d]pyrimidine derivative represented by the general formula (101) or a pharmacologically acceptable salt thereof, which comprises condensing a compound represented by the following general formula (102):

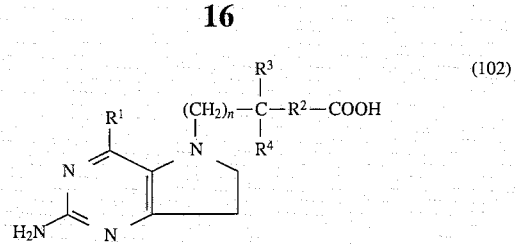

(102)

wherein R¹ represents a hydroxyl or amino group, R² represents a phenylene, thiendiyl, furandiyl or thiazoldiyl group, R³ and R⁴ may be the same or different from each other and each represent a hydrogen atom or a hydrocarbon group which may be substituted, and n is an integer of 1 to 3, or a reactive derivative thereof wherein the carboxyl group is modified to a reactive form, with a compound represented by the following general formula (103):

(103)

wherein R⁵ and R⁶ may be the same or different from each other and each represent a carboxyl-protective group, to form a carboxylic ester represented by the following general formula (104):

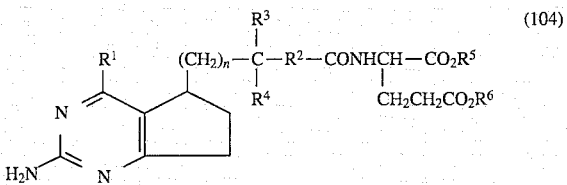

(104)

wherein R¹, R², R³, R⁴, R⁵, R⁶ and n are each as defined in the above general formulas 102 and 103, and converting the ester into a corresponding free carboxylic acid through acidic or alkaline hydrolysis or hydrogenolysis including catalytic reduction.

Furthermore, the present invention provides an antitumor drug containing the pyrimidine derivative represented by the above general formula (I) or pharmacologically acceptable salt thereof as an active ingredient, preferably one containing the pyrrolo[3,2-d]pyrimidine derivative represented by the above general formula (1) or pharmacologically acceptable salt thereof, or one containing the 6,7-dihydro-5H-cylopenta[d]pyrimidine derivative represented by the above general formula (101) or a pharmacologically acceptable salt thereof as an active ingredient.

Moreover, the present invention provides a drug composition comprising an effective amount of the pyrimidine derivative represented by the above general formula (I) or pharmacologically acceptable salt thereof and a filler, a use of the pyrimidine derivative represented by the above general formula (I) or pharmacologically acceptable salt thereof in the preparation of a drug which is effective in treating a disease for which the administration of an antitumor drug is efficacious, and a method for treating a patient with a disease for which the administration of an antitumor drug is efficacious, which comprises administering an effective amount of the pyrimidine derivative represented by the above general formula (I) or pharmacologically acceptable salt thereof to the patient.

The compounds represented by the above formulas (1), (2), (4), (101), (102), (104) and (105) wherein R¹ is a hydroxyl group are each present in a state wherein keto and enol tautomers coexist in equilibrium. Although the compounds are, for convenience, represented as their enol tautomers (i.e., hydroxyl compounds) and named accordingly in this specification, the present invention includes the keto tautomers (i.e., oxo or amide compounds) as well as the enol tautomers in any case.

Further, although the compound represented by the above formula (I) of the present invention may have an asymmetric center at the 5-position carbon atom of the heterocycle moiety or at the carbon atom to which $R^3$ and $R^4$ are bonded in the case that A represented by the formula:

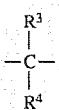

(wherein $R^3$ and $R^4$ may be the same or different from each other and each represent a hydrogen or halogen atom or a hydrocarbon group which may be substituted) in addition to that of the L-glutamic acid moiety, each asymmetric center may take either S- or R-configuration or a mixture of them, with the proviso that the asymmetric carbon atom of the glutamic acid moiety must take S- (L-) absolute configuration. In such a case, the compound represented by the above formula (I) is prepared as a diastereomer or as a diastereomer mixture, which can be easily separated and purified by the conventional process such as fractional crystallization or chromatography at need. The diastereomers thus separated all fall within the scope of the present invention.

The compound represented by the above formula (I) of the present invention is generally prepared as a powder, crystalline solid or crystal.

DETAILED DESCRIPTION OF THE INVENTION

The present invention will now be described in detail.

In the above definition, the phenylene group defined with respect to $R^2$ may be a 1,4- or 1,3-phenylene group and the thiendiyl and furandiyl groups with respect to $R^2$ may each have free valencies at 2,5 (or 5,2)- or 3,5 (or 5,3)-positions. The pyridinediyl group with respect to $R^2$ may have free valencies at 2,5- or 5,2-positions. The thiazoldiyl groups with respect to $R^2$ may have free valencies at 1,3- or 1,4-positions.

In the above definition, the hydrocarbon group defined with respect to $R^3$, $R^4$ and $R^{70}$ includes lower alkyl, lower alkenyl and lower alkynyl groups. The lower alkyl group may be a straight-chain or branched one having 1 to 6 carbon atoms and examples thereof include methyl, ethyl, n-propyl, isopropyl, n-butyl, isobutyl, sec-butyl, tert-butyl, n-pentyl(amyl), isopentyl, 1-methylbutyl, 1,2-dimethylpropyl, n-hexyl, isohexyl, 1-methylpentyl, 3-methylpentyl, 1,2-dimethylbutyl, 2,3-dimethylbutyl, 1-ethylbutyl, 1,1,2-trimethylpropyl, 1-ethyl-1-methylpropyl and 1-ethyl-2-methylpropyl groups. Among these groups, methyl, ethyl, propyl and isopropyl groups are desirable and methyl and ethyl groups are most desirable.

The lower alkenyl group may be a straight-chain or branched one having 2 to 6 carbon atoms and examples thereof include ethenyl(vinyl), 1-propenyl, 2-propenyl, 1-butenyl, 2-butenyl, 2-methylpropenyl, 3,3-dimethyl-1-butenyl and 4-methyl-2-pentenyl groups, among which 1-propenyl and 2-propenyl groups are preferable.

Further, the lower alkynyl group includes ethynyl, 1-propynyl, 2-propynyl(propargyl), butynyl, hexynyl and pentynyl groups, among which propargyl group is preferable.

In the above definition, the hydrocarbon group which may be substituted defined with respect to $R^3$ and $R^4$ includes halogenated hydrocarbon groups such as a halogenated lower alkyl, alkenyl and alkynyl groups.

The alkylidene group formed by the union of $R^3$ and $R^4$ includes methylene, ethylidene and isopropylidene groups.

The halogen atom defined with respect to $R^3$ and $R^4$ includes chlorine atom, bromine atom, iodine atom and fluorine atom.

The carboxyl-protective group defined with respect to $R^5$, $R^6$ and $R^{10}$ includes alkyl groups having 1 to 5 carbon atoms, benzyl groups which may be substituted, phenyl groups which may be substituted and trisubstituted silyl groups. Examples of the alkyl groups include methyl, ethyl, propyl, isopropyl, butyl, isobutyl, t-butyl and pentyl groups; those of the benzyl groups which may be substituted include benzyl, nitrobenzyl and methoxybenzyl groups; those of the phenyl groups which may be substituted include phenyl, methoxyphenyl and nitrophenyl groups; and those of the trisubstituted silyl groups include t-butyldimethylsilyl and t-butyldiphenylsilyl groups.

Although the objective compound described above and the intermediates obtained in the course of the preparation thereof may be each present as an optical isomer and/or a geometrical isomer owing to the presence of an asymmetric carbon atom and/or a double bond, such isomers also fall within the scope of the present invention. Although the objective compound or the intermediates are each prepared as an isomer mixture when some preparation process is employed, the mixture may be separated and purified by the conventional process such as fractional crystallization or chromatography prior to the use.

The compound of the present invention can form a pharmacologically acceptable salt together with an organic or inorganic acid. Preferred examples of the acid include hydrochloric, sulfuric, phosphoric, acetic, citric, malonic, salicylic, malic, fumaric, maleic, succinic, ascorbic and methanesulfonic acids. The pharmacologically acceptable salt can be prepared by adding such an organic or inorganic acid in a necessary amount to the compound of the present invention in a free base form according to the conventional process. The salt thus prepared can be converted again into the free base by treatment with a base. The base to be preferably used for this purpose includes aqueous solutions of sodium hydroxide, potassium carbonate, ammonia and sodium hydrogencarbonate.

Further, the compound of the present invention can be converted into a pharmacologically acceptable carboxylate salt by reacting the free carboxyl groups of the compound with a suitable base. Preferred examples of the base include hydroxides and carbonates of alkali metals and alkaline earth metals, such as sodium hydroxide and potassium hydroxide, and carbonates corresponding to them, and nitrogenous bases such as ammonia and alkylamines represented by triethylamine.

The preparation of the compound represented by the formula (I) according to the present invention will now be described.

The compound represented by the formula (I) can be prepared as represented by the following reaction scheme 1, i.e., by condensing a carboxylic acid represented by the formula (III) or a reactive derivative thereof with a glutamic acid derivative represented by the formula (IV) to form an intermediate represented by the formula (I') and by deprotecting the intermediate of the carboxyl-protective groups through hydrolysis or hydrogenolysis.

Reaction Scheme 1:

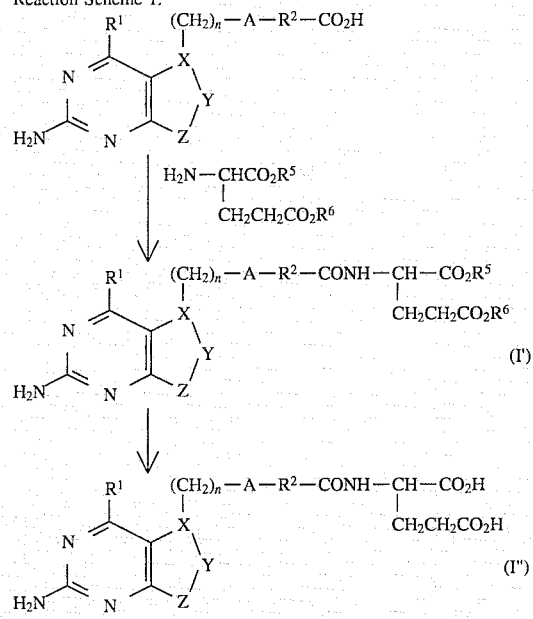

(I')

(I")

wherein $R^1$, $R^2$, $R^5$, $R^6$, A the part

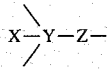

and n are each as defined according to the formulas (I), (III) and (IV).

Although such a series of reactions beginning with the condensation of a compound represented by the formula (III) with a compound represented by the formula (IV) and ending in the deprotectiving of various functional groups is well known and is therefore ought to be easily conducted by any person skilled in the art, a specific example of the process for preparing a compound represented by the general formula (I) will now be described, though it is a matter of course that the present invention is not limited thereto.

A specific example of the process for preparing a compound represented by the general formula (101), i.e., 6,7-dihydro-5H-cyclopenta[d]pyrimidine derivative will now be described.

The compound represented by the formula (101) can be prepared as represented by the following reaction scheme 2, i.e., by condensing a carboxylic acid represented by the formula (102) or a reactive derivative thereof with a glutamic acid derivative represented by the formula (103) to form an intermediate represented by the formula (104) and freeing the intermediate of the carboxyl-protective groups through hydrolysis or hydrogenolysis.

Reaction Scheme 2:

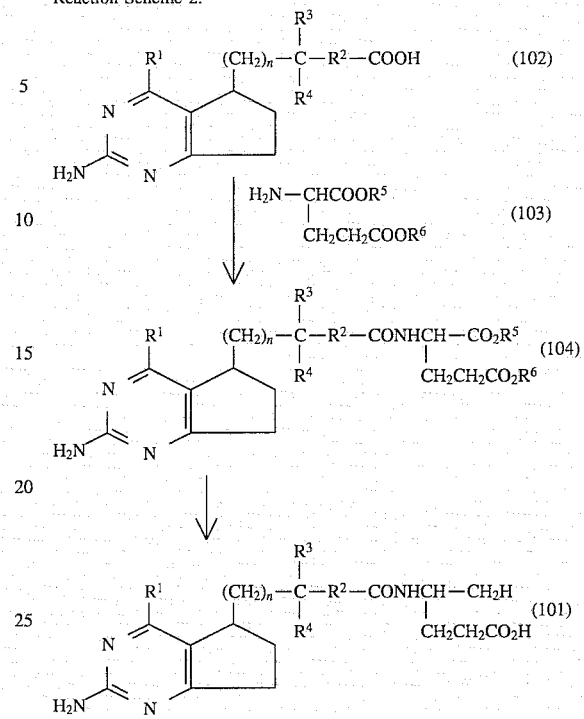

wherein $R^1$, $R^2$, $R^3$, $R^4$, $R^5$, $R^6$ and n are each as defined according to the formulas (101), (102), (103) and (104).

Any conventional process for peptide synthesis can be applied to the above condensation. For example, the intermediate (104) can be prepared by reacting the compound (102) with a carboxylic acid-activating reagent such as chlorocarbonic acid ester, organic acid anhydride, diphenylphosphoryl azide, diethyl phosphorocyanidate carbonyldiimidazole, chlorophosphoric acid ester or carbodiimide in the presence or absence of a base and reacting the obtained compound with the compound (103).

The amount of the activating reagent to be used is 1 to 25 equivalents by mole, preferably 1 to 5 equivalents by mole based on the compound (102). The chlorocarbonic acid ester to be used as the activating agent includes methyl chlorocarbonate and ethyl chlorocarbonate; the organic acid anhydride includes acetic anhydride, chloroacetic anhydride and mixed acid anhydride; and the chlorophosphoric acid ester includes diphenyl chlorophosphate and diethyl chlorophosphate. The carbodiimide is preferably dicyclohexylcarbodiimide from the standpoint of practical use, but may be suitably selected from among diphenylcarbodiimide, 1,3-di-p-tolylcarbodiimide, 1-cyclohexyl-3-(2-morpholinoethyl) carbodiimide and so forth.

The above reaction is preferably conducted in the presence of a solvent and the solvent may be selected from among water, alcohols (such as methanol, ethanol and propanol), ethers (such as diethyl ether, tetrahydrofuran and dioxane), nitriles (such as acetonitrile), aromatic hydrocarbons (such as benzene and toluene), halogenated hydrocarbons (such as dichloromethane, chloroform and carbon tetrachloride), acetone, pyridine, dimethylformamide, dimethyl sulfoxide and so forth. Alternatively, a mixture of two or more members suitably selected from among them may be used as the solvent.

The reaction is conducted in the presence or absence of a base. The base to be used is suitably selected from among inorganic bases such as sodium methylate, sodium ethylate, sodium hydroxide, potassium hydroxide, sodium carbonate, potassium carbonate and sodium hydrogencarbonate; and organic bases such as triethylamine, trimethylamine, pyridine and triethanolamine.

Then, the ester intermediate (104) prepared in the above condensation step can be converted into a corresponding free carboxylic acid through hydrolysis or hydrogenolysis, thus giving the compound (101).

The hydrolysis may be conducted in water or, if necessary, in a hydrophilic organic solvent such as methanol, ethanol, tetrahydrofuran, dioxane, dimethylformamide or dimethyl sulfoxide by the use of an aqueous inorganic acid such as hydrochloric, sulfuric, nitric or phosphoric acid, an organic acid such as trifluoroacetic, trichloroacetic, p-toluenesulfonic, benzenesulfonic or methanesulfonic acid, an aqueous caustic alkali such as sodium hydroxide or potassium hydroxide, an alkali carbonate such as sodium carbonate or potassium carbonate, a metal alkoxide such as sodium methoxide or sodium ethoxide or an amine such as triethylamine or pyridine. The reaction temperature ranges from the temperature attained under cooling with ice to the boiling point of the solvent used, preferably from 10° to 70° C. and the reaction time is from one hour to about two days. When an alkali or organic base is used, the glutamic acid moiety of the product is in the form of an acidic or neutral salt thereof.

Hydrogenolysis is a suitable means when $R^5$ and $R^6$ are each a benzyl or phenyl group which may be substituted. The hydrogenolysis of such a compound is conducted as follows. That is, the compound (104) is catalytically reduced by treating it with hydrogen in a suitable solvent at a temperature ranging from –20° C. to the boiling point of the solvent, preferably from 0° to 50° C. in the presence of a reduction catalyst under normal or elevated pressure.

The solvent to be used therein includes water, methanol, ethanol, propanol, ethyl acetate, diethyl ether, tetrahydrofuran, dioxane, benzene, toluene, dimethylformamide, pyridine and so forth, while palladium, platinum or rhodium is used as the reduction catalyst either alone or in a state supported on a carrier and Raney nickel can be also used as the catalyst.

Then, the preparation of the starting material (102) will now be described.

A compound represented by the formula (102) wherein $R^1$ is an amino group can be prepared through, e.g., the following reaction route shown in the reaction scheme 3:

Reaction Scheme 3:

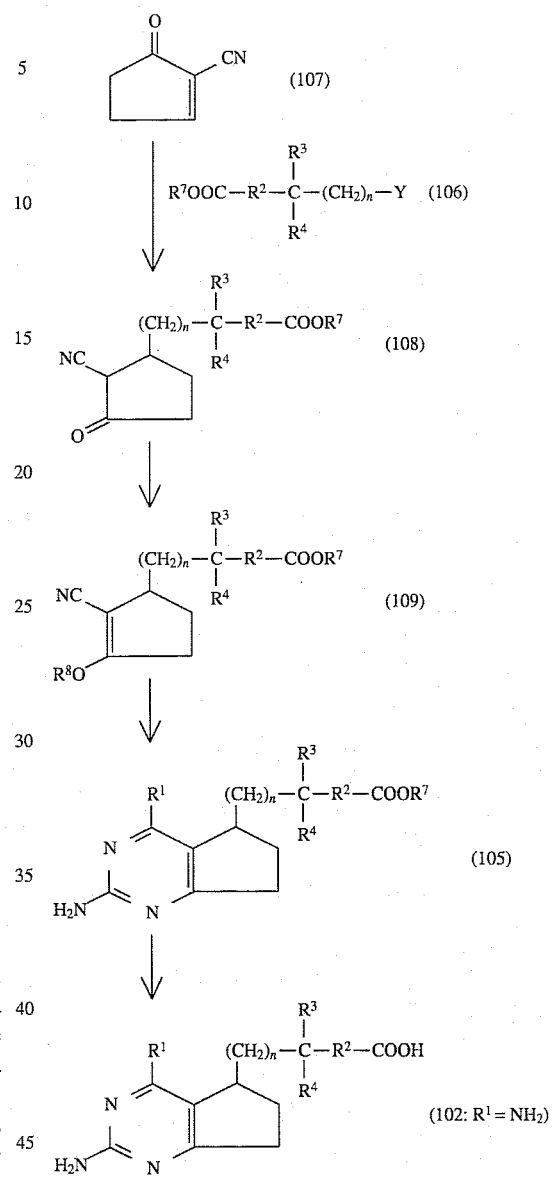

wherein $R^1$ represents an amino group; $R^2$, $R^3$, $R^4$ and n are each as defined according to the formulas (102) and (105); Y represents a halogen atom such as a chlorine, bromine or iodine atom; $R^7$ represents a carboxyl-protective group; and $R^8$ represents a conventional enol-protective group such as an methyl, ethyl, benzyl or tetrahydropyranyl group.

The above reaction steps will now be described.

2-Cyano-2-cyclopenten-1-one (107) can be smoothly prepared in a high yield by reacting cyclopentenone with a tri(lower alkyl)aluminum and an aromatic thiol such as thiophenol or a bulky aliphatic thiol such as isopropylthiol, and then with tosyl cyanide and reacting the product thus prepared with a Lewis acid such as silica gel or boron trifluoride-ether. In this case, 2-cyano-2-cyclopenten-1-one (107) is formed through 3-alkylthio-2-cyanocyclopentane as an intermediate.

A compound (108) can be prepared by reacting a cyclic carboxylic ester (106) having an ω-halogenoalkyl group with the 2-cyano-2-cyclopenten-1-one (107). This reaction is conducted in the presence of a tin hydride such as trialkyltin hydride or triphenyltin hydride or a trialkylgermanium hydride and a free radical initiator such as azobisisobutyronitrile.

Alternatively, the compound (108) can be also prepared by reacting an organocopper compound prepared from the iodoalkyl compound (106) with 2-cyano-2-cyclopenten-1-one (107). The organocopper compound to be used in this reaction can be prepared by adding a copper salt to an organozinc compound derived from the iodoalkyl compound (106).

The conversion of the 3-substituted alkyl-2-cyanocyclopentan-1-one (108) into a lower alkyl enol ether (109) can be conducted by reacting the compound (108) with a conventional hydroxyl-protecting reagent such as diazomethane or an analogue thereof, 2,2-dimethoxypropane/p-toluenesulfonic acid or orthoformic acid ester.

The 1-alkoxy-2-cyano-3-substituted alkyl-1-cyclopentene compound (109) can be converted into a 2,4-diamino-6,7-dihydro-5H-cyclopenta[d]pyrimidine compound represented by the formula (105) wherein $R^1$ is an amino group, which is one of the objective compounds, by reacting the compound (109) with guanidine or a salt thereof either under normal pressure or in a sealed tube under heating. In this reaction, guanidine is used in excess based on the enol ether (109) [e.g., in a molar amount which is 2 to 20 times, preferably 5 to 10 times that of the ether (109)], while the solvent to be used is preferably a protic solvent such as methanol, ethanol, methoxyethanol, propanol or 2-methyl-2-propanol. The reaction temperature is 50° to 200° C., preferably 12 to 185° C. and the reaction time is preferably 8 to 70 hours. When the reaction is conducted at a high temperature for a long time, a carboxylic acid represented by the formula (102) is formed directly in some case.

Generally, a carboxylic acid having a 6,7-dihydro-5H-cyclopenta[d]pyrimidine ring (102) can be prepared by subjecting a corresponding carboxylic ester represented by the formula (105) to acidic or alkaline hydrolysis or hydrogenolysis including catalytic reduction according to the same procedure as that of the conversion of the compound (104) into the compound (101).

A compound represented by the formula (105) wherein $R^1$ is a hydroxyl group can be prepared through the following reaction route shown in the reaction scheme 4:

Reaction Scheme 4:

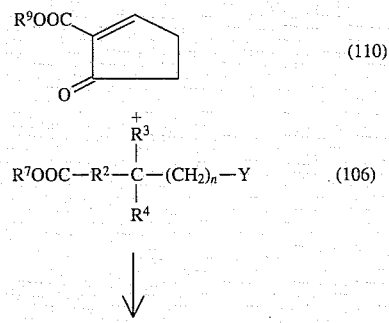

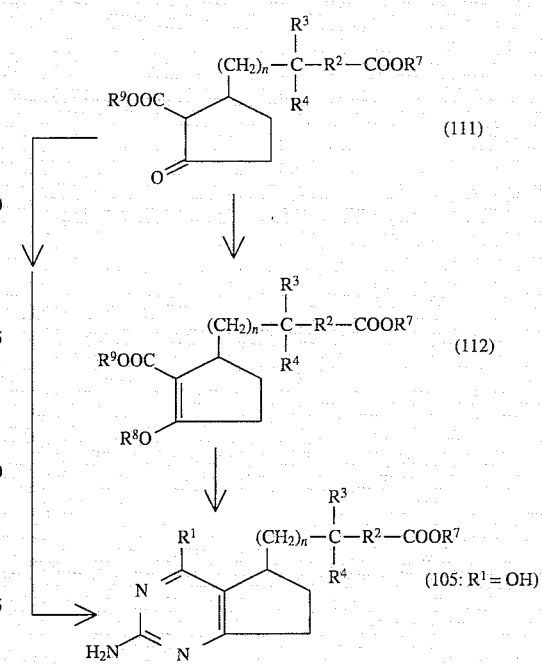

wherein $R^1$ represents a hydroxyl group; $R^2$, $R^3$, $R^4$, $R^7$, $R^8$, n and Y are each as defined according to the reaction scheme 3; and $R^9$ represents a lower alkyl group having 1 to 4 carbon atoms.

A 2-carboalkoxy-2-cyclopenten-1-one (110) can be prepared by a known process. That is, it can be prepared from 2-cyclopenten-1-one according to the process disclosed by M. A. Guaciaro et al. in Tetrahedron, 47, 4661 (1978) or from 2-carboethoxycyclopentanone according to the process disclosed by H. J. Reich et al. in J. Am. Chem. Soc., 97, 5434 (1975) and the product obtained by either of the processes can be used for attaining the object of the present invention.

A keto compound (111) can be prepared by reacting a cyclic carboxylic ester having an ω-halogenoalkyl group (106) with the 2-carboalkoxy-2-cyclopenten-1-one (110) in the presence of tin hydride and azobisisobutyronitrile.

Alternatively, the keto compound (111) can be also prepared by reacting an organocopper compound prepared from the iodoalkyl compound (106) with 2-carboalkoxy-2-cyclopenten-1-one (110). The organocopper compound to be used in this reaction can be prepared by adding a copper salt to an organozinc compound derived from the iodoalkyl compound (106).

The conversion of the keto compound, i.e., cyclopentanone ring-containing carboxylic ester (111) into an enol ether (112) can be smoothly conducted by reacting the ester (111) with a conventional hydroxyl-protecting reagent such as diazomethane or an analogue thereof, 2,2-dimethoxypropane/p-toluenesulfonic acid or orthoformic ester.

The 3-substituted alkyl-2-carboalkoxy-1-cyclopentanone compound (111) or 1-alkoxy-3-substituted alkyl-2-carboalkoxy-1-cyclopentene compound (112) can be converted into a 2-aminohydroxypyrimidine ring-containing alkanecarboxylic ester represented by the formula (105) wherein $R^1$ is a hydroxyl group by reacting the compound (111) or the compound (112) with guanidine or a salt thereof in a solvent. The solvent to be used in the conversion and the reaction temperature and reaction time to be employed therein may be nearly the same as those described in the above-mentioned case wherein $R^1$ is an amino group.

Meanwhile, the cyclic carboxylic ester having a halogenoalkyl group (106) to be used in the above process as an intermediate can be prepared by the processes which will be described in the reaction schemes 5 and 6.

The first process for preparing the cyclic ester (106) is as follows:

Reaction Scheme 5:

First process

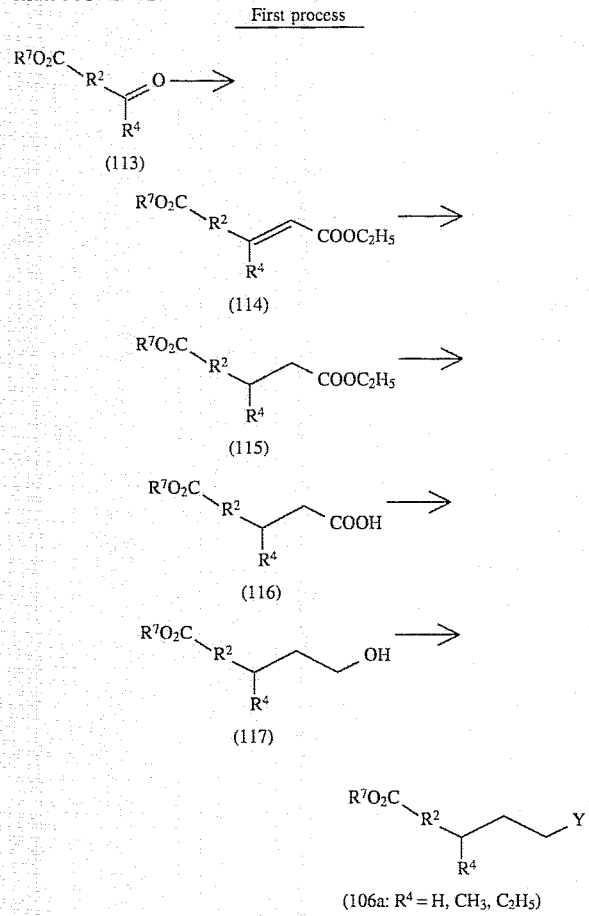

(106a: $R^4$ = H, $CH_3$, $C_2H_5$)

wherein $R^2$, $R^3$, $R^4$, $R^7$, n and Y are each as defined according to the reaction scheme 3.

An α,β-unsaturated carboxylic ester represented by the formula (114) wherein $R^4$ is a hydrogen atom or a hydrocarbon group and $R^2$ and $R^7$ are each as defined above can be prepared by gradually adding a 5- or 6-membered ring aldehyde having a protected carboxyl group [which is represented by the formula (113) wherein $R^4$ is a hydrogen atom and $R^2$ and $R^7$ are each as defined above and examples of which include t-butoxycarbonyl-substituted benzaldehyde, t-butoxycarbonyl-substituted thienylaldehyde and t-butoxycarbonyl-substituted furanylaldehyde, each substituent being present at any of positions 2,3,4 and 5] or a 5- or 6-membered ring ketone having a protected carboxyl group [which is represented by the formula (113) wherein $R^4$ is a hydrocarbon group such as an alkyl, propargyl or propenyl group and examples of which include alkyl t-butoxycarbonylphenyl ketone, alkyl t-butoxycarbonylphenyl ketone, alkyl t-butoxycarbonylfuranyl ketone and propargyl t-butoxycarbonylphenyl ketone] to a mixture prepared by adding a trialkyl phosphonoacetate (such as trimethyl phosphonoacetate or triethyl phosphonoacetate) to an organic solvent (i.e., an aprotic solvent such as dimethylformamide, ether, tetrahydrofuran, hydrocarbon such as hexane or a mixture of two or more of them) containing a base (such as potassium t-butoxide/tetrahydrofuran, sodium hydride, lithium hydride or 1,5-diazacyclo[4.3.0]non- 5-ene (DBN)) and reacting the obtained mixture at room temperature or under heating. The unsaturated ester (114) thus prepared is catalytically reduced under normal or elevated pressure into a corresponding saturated ester (115), which is further converted into a 5- or 6-membered ring compound having a carboxyl group [which is represented by the formula (116) wherein $R^4$ is a hydrogen atom or a hydrocarbon group and $R^2$ and $R^4$ are each as defined above and examples of which include ω-(4-(t-butoxycarbonyl)phenyl) propionic, ω-(5-(t-butoxycarbonyl)-2-thienyl)propionic and ω-(5-(t-butoxycarbonyl)-2-furanyl)propionic acids, which may be substituted with an alkyl group at the benzyl position]. The compound (116) thus prepared is converted into a corresponding alcohol (117) by reducing the carboxyl group into a hydroxyl group. The reducing agent to be used in the reduction includes borane and borane analogues (such as borane-dimethyl sulfide, borane-tetrahydrofuran and 9-boracyclo[3.3.1]nonane), while the solvent to be used therein includes tetrahydrofuran and ether. Then, the alcohol (117) is esterified (e.g., mesylated or tosylated) with a sulfonic acid in the presence of a base and the obtained ester is further halogenated with an alkali halite in an aprotic solvent under heating to give a cyclic carboxylic ester having an ω-halogenoalkyl group (106a) [corresponding to a compound represented by the formula (106) wherein $R^3$ is a hydrogen atom; $R^4$ is a hydrogen atom or a methyl or ethyl group; n is 2; and $R^2$, $R^7$ and Y are each as defined according to the formula (106)]. For example, ω-(4-(t-butoxymarbonyl)phenyl)propyl halide, ω-(5-(t-butoxycarbonyl)-2-thienyl) propyl halide and ω-(5-(t-butoxycarbonyl)-2-furanyl)propyl halide can be prepared by this process.

A cyclic carboxylic ester represented by the formula (106) wherein $R^3$ is a hydrogen atom, $R^4$ is a hydrogen atom or a lower alkyl group, n is 1 and $R^2$ and $R^7$ are each as defined according to the formula (106) can be prepared by the second process, which will now be described in the reation scheme 6.

Reaction Scheme 6:

First process

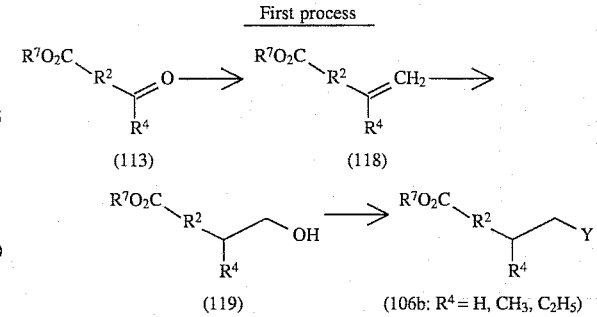

(106b: $R^4$ = H, $CH_3$, $C_2H_5$)

The carbonyl group of a compound represented by the formula (113) wherein $R^2$ and $R^7$ are each as defined according to the formula (106) and $R^4$ is a hydrogen atom or a lower alkyl group can be converted into an exo methylene group through the Wittig reaction and the exo methylene group can be further converted into a hydroxymethyl group through hydroboration. The hydroxymethyl compound thus prepared can be further converted into a halogenide (106b). More specifically, an exo methylene compound (118) can be prepared by adding, under cooling, a compound (113) to a solution which has been preliminarily prepared by adding butyllithium to a solution of methyltriphenylphosphonium bromide in tetrahydrofuran under cooling to conduct a reaction. The compound (118) is hydroborated with a boron hydride compound such as 9-borabicyclo[3.3.1]nonane, borane, dicyclohexylborane, disiamylborane or thexylborane and then reacted with an alkaline solution of hydrogen peroxide to give a primary alcohol (119), which can be converted into an ω-halogenoalkyl compound (106b) [corresponding to a compound represented by the formula (106) wherein $R^3$ is a hydrogen atom, $R^4$ is a hydrogen atom or a methyl or ethyl group, n is 1 and $R^2$, $R^7$ and Y are each as defined according to the formula (106)] according to the same procedure as that of the above conversion of (117) into (106a).

The compound (106) thus prepared is used in the preparation of the compounds (108) and (111) which are important intermediates in the present invention.

Among the compounds (113) to be used in the above processes, a compound represented by the formula (113) wherein $R^2$ is a thiendiyl group and $R^4$ is a hydrogen atom can be prepared as follows: First, a 2-thiophenecarboxylic ester is prepared by reacting commercially available 2-thiophenecarbonyl chloride with an alkoxide either under cooling or at room temperature. Then, the 2-thiophenecarboxylic ester is converted into a 2-formyl-5-thiophenecarboxylic ester (113) by reacting the 2-thiophenecarboxylic ester with butyllithium in the presence of N,N,N',N'-tetramethylethylenediamine under cooling and adding anhydrous dimethylformamide to the obtained reaction mixture to conduct a reaction. Further, a compound represented by the formula (113) wherein $R^2$ is a thiendiyl group and $R^4$ is a methyl or ethyl group can be also prepared in a similar manner to that described above. That is, corresponding methyl thienyl ketone and ethyl thienyl ketone can be prepared by the same procedure as that described above except that the dimethylformamide is replaced by dimethylacetamide or dimethylpropioiamide. Furthermore, a compound represented by the formula (113) wherein $R^2$ is a phenylene group and $R^4$ is a hydrogen atom can be prepared by converting p-formylbenzoic acid into a corresponding acid chloride and subjecting the acid chloride to esterification, while a compound represented by the formula (113) wherein $R^2$ is a phenylene group and $R^4$ is a methyl or ethyl group can be prepared by the method of R. Joyeau et al. (see J. Chem. Soc., Perkin Trans. I, 1899 to 1907 (1987)).

Specific examples of the compound represented by the formula (101) according to the present invention include N-{4-[2-(2,4-diamino-6,7-dihydro-5H-cyclopenta[d]pyrimidin-5-yl)ethyl]benzoyl}-L-glutamic acid, N-{5-[3-(2,4-diamino-6,7-dihydro-5H-cyclopenta[d]pyrimidin-5-yl)propyl]-2-thenoyl}-L-glutamic acid, N-{4-[3-(2,4-diamino-6,7-dihydro-5H-cyclopenta[d]pyrimidin-5-yl)propyl]benzoyl}-L-glutamic acid, N-{5-[2-(2,4-d.amino-6,7-dihydro-5H-cyclopenta[d]pyrimidin-5-yl)ethyl]-2-thenoyl}-L-glutamic acid, N-{5-[2-(2,4-diamino-6,7-dihydro-5H-cyclopenta[d]pyrimidin-5-yl)ethyl]-2-furoyl}-L-glutamic acid, N-{5-[3-(2,4-diamino-6,7-dihydro-5H-cyclopenta[d]pyrimidin-5-yl)propyl]-2-furoyl}-L-glutamic acid, N-{5-[2-(2,4-d-amino-6,7-dihydro-5H-cyclopenta[d]pyrimidin-5-yl)-1-ethylethyl]-2-thenoyl}-L-glutamic acid, N-{4-[2-(2,4-diamino-6,7-dihydro-5H-cyclopenta[d]pyrimidin-5-yl)-1-ethylethyl]benzoyl}-L-glutamic acid, N-{5-[2-(2,4-diamino-6,7-dihydro-5H-cyclopenta[ d]pyrimidin-5-yl)-1-methylethyl]-2-thenoyl}-L-glutamic acid, N-{4-[2-(2,4-diamino-6,7-dihydro-5H-cyclopenta[d]pyrimidin-5-yl)-1-methylethyl]benzoyl}-L-glutamic acid, N-[5-[3-(2,4-diamino-6,7-dihydro-5H-cyclopenta[d]pyrimidin-5-yl)-1-methylpropyl]-2-thenoyl}-L-glutamic acid, N-{4-[3-(2,4-d-amino-6,7-dihydro-5H-cyclopenta[d]pyrimidin-5-yl)-1-methylpropyl]benzoyl}-L-glutamic acid, N-{4-[2-(2-amino-4-hydroxy-6,7-dihydro-5 H-cyclopenta [d]pyrimidin-5-yl)ethyl]benzoyl}-L-glutamic acid, N-{5-[2-(2-amino-4-hydroxy-6,7-dihydro-5 H-cyclopenta [d]pyrimidin-5-yl)ethyl]-2-thenoyl}-L-glutamic acid, N-{5-[2-(2-amino-4-hydroxy-6,7-dihydro-5 H-cyclopenta [d]pyrimidin-5-yl)ethyl]-2-furoyl}-L-glutamic acid, N-{4-[3-(2-amino-4-hydroxy-6,7-dihydro-5 H-cyclopenta [d]pyrimidin-5-yl)propyl]benzoyl}-L-glutamic acid, N-{5-[3-(2-amino-4-hydroxy-6,7-dihydro-5 H-cyclopenta [d]pyrimidin-5-yl)propyl]-2-thenoyl}-L-glutamic acid, N-{5-[3-(2-amino-4-hydroxy-6,7-dihydro-5 H-cyclopenta [d]pyrimidin-5-yl)propyl]-2-furoyl}-L-glutamic acid, N-{5-[2-(2-amino-4-hydroxy-6,7-dihydro-5 H-cyclopenta [d]pyrimidin-5-yl)-1-ethylethyl]-2-thenoyl}-L-glutamic acid, N-{4-[2-(2-amino-4-hydroxy-6,7-dihydro-5 H-cyclopenta [d]pyrimidin-5-yl)-1-ethylethyl]benzoyl}-L-glutamic acid, N-{5-[2-(2-amino-4-hydroxy-6,7-dihydro-5 H-cyclopenta [d]pyrimidin-5-yl]-1-methylethyl]-2-thenoyl]-L-glutamic acid and N-{4-[2-(2-amino-4-hydroxy-6,7-dihydro-5 H-cyclopenta [d]pyrimidin-5-yl)-1-methylethyl]benzoyl}-L-glutamic acid.

A compound represented by the general formula (1), i.e., a pyrrolo[3,2-d]pyrimidine derivative will now be described.

The pyrrolo[3,2-d]pyrimidine derivative represented by the general formula (1) and pharmacologically acceptable salts thereof (hereinafter abbreviated to "compound (1)") which are the objective compounds of the present invention and the intermediates for the preparation thereof can be prepared by the processes represented by the reaction schemes which will be described below. In the reaction schemes, Me represents a methyl group, Et an ethyl group, Bu a butyl group, Ac an acetyl group and Ph a phenyl group.

Reaction Scheme 7:

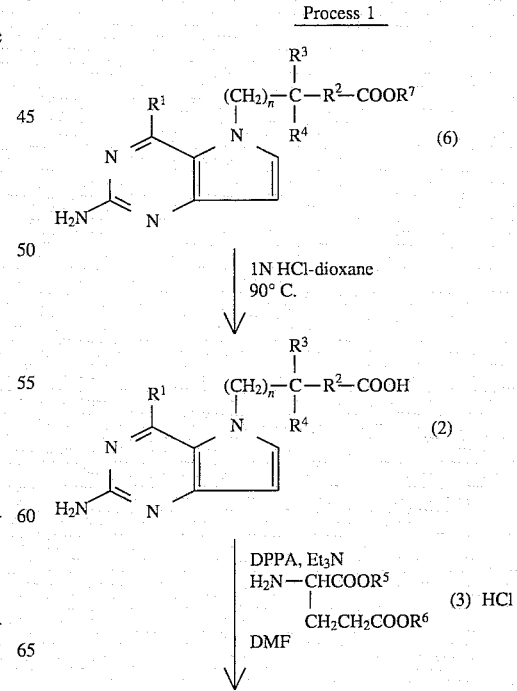

Reaction Scheme 7:

Process 1

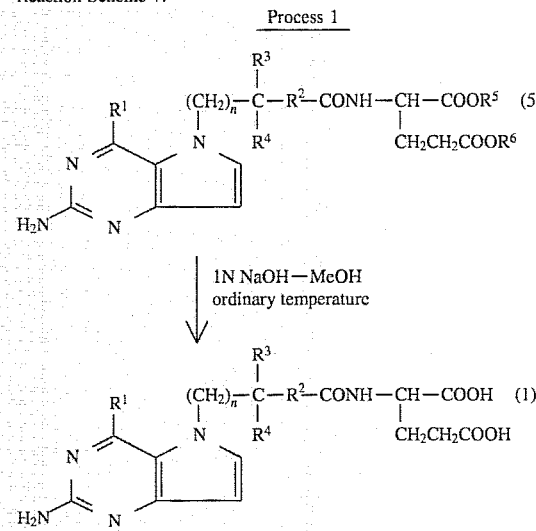

wherein $R^1$, $R^2$, $R^3$, $R^4$ and n are each as defined according to the formula (1.); and $R^5$, $R^6$ and $R^7$ may be the same or different from each other and each represent a carboxyl-protective group, while the carboxyl-protective group includes t-butyl, t-butyldimethylsilyl, t-butyldiphenylsilyl, alkyl ($C_{1-4}$), benzyl, substituted benzyl and phenyl groups.

The compound (1) of the present invention or a salt thereof can be prepared by the hydrolysis or hydrogenolysis of the compound (5). The hydrolysis may be conducted by the use of an aqueous inorganic acid, an organic acid such as trifluoroacetic acid, an aqueous alkali hydroxide or alkali carbonate or an organic base in an aqueous solution, or if necessary, in the presence of a hydrophilic organic solvent such as methanol, ethanol, tetrahydrofuran, dioxane or dimethylformamide at ordinary temperatures. When an alkali or an organic base is used, the glutamic acid moiety of the product is in the form of an acidic or neutral salt thereof. Hydrogenolysis is a suitable means when $R^5$ and $R^6$ are each a benzyl, substituted benzyl or phenyl group. The hydrogenolysis of the compound (5) may be conducted in the presence of a suitable catalyst such as palladium, either alone or in a state supported on a carrier under normal or elevated pressure. The compound (1) prepared by the above process is generally in the form of powder, crystalline solid or crystal.

The ester compound (5) which is an intermediate for the preparation of the compound (1) can be prepared by the conventional process for peptide synthesis, i.e. by reacting a compound (2) having a pyrrolo[3,2-d]pyrimidine ring with a carboxylic acid-activating reagent such as chlorocarbonate ester, organic acid anhydride, DPPA. CDI, chlorophosphate ester or DCC in the presence or absence of a base to convert the compound (2) into an active derivative such as a mixed acid anhydride or active ester and reacting the active derivative with a glutamic acid derivative (3) in which the carboxyl groups are protected.

The compound (2) can be prepared from a compound (6) through hydrolysis with an acid or alkali or hydrogenolysis including catalytic reduction.

The compound (6) to be used in the Process 1 can be prepared by, e.g., the following process 2 shown in the reaction scheme 8:

Reaction Scheme 8:

Process 2

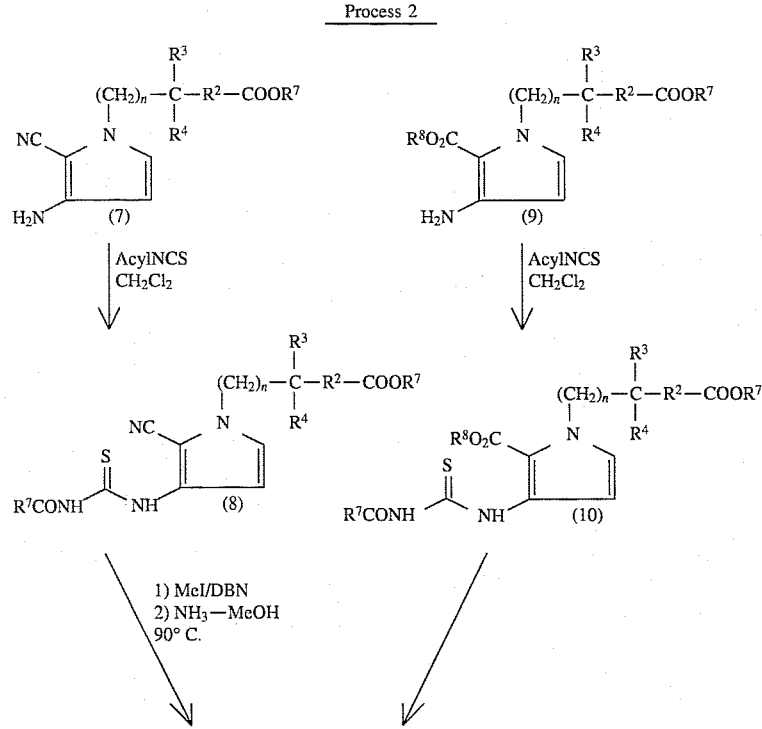

Reaction Scheme 8:

-continued

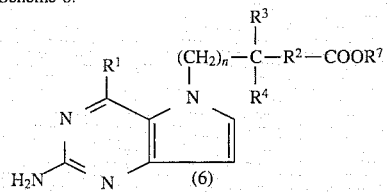

wherein $R^1$, $R^2$, $R^3$, $R^4$, $R^7$ and n are each as defined according to the reaction scheme 7; $R^8$ represents a carboxyl-protective group; and $R^9$ represents an alkyl or phenyl group.

When the objective compound is a 2,4-diaminopyrimidine compound corresponding to the one represented by the formula (6) wherein $R^1$ is an amino group, it can be prepared by reacting a compound (7) with an N-acylisothiocyanate (AcylNCS wherein the Acyl group corresponding to the $R^9CO$ group is an aliphatic or aromatic one such as an acetyl or benzoyl group in an aprotic solvent to thereby convert the compound (7) into a compound (8) smoothly, subjecting the compound (8) to S-lower-alkylation (such as methylation) according to the conventional process, and reacting the obtained S-alkylate with $NH_3$ either under normal pressure or in a sealed tube under heating.

When the objective compound is a 2-amino-4-hydroxylpyrimidine compound corresponding to the one represented by the formula (6) wherein $R^1$ is a hydroxyl group, it can be prepared by reacting a compound (9) with an N-acylisothiocyanate (AcylNCS) in a solvent either at room temperature or under cooling to thereby convert the compound (9) into a compound (10), subjecting the compound (10) to S-lower-alkylation and treating the obtained alkylate with $NH_3$ under heating to convert the alkylate into the objective compound through ring closure.

The compound (7) to be used in the Process (2) can be prepared by the following process 3 shown in the reaction scheme 9.

Reaction Scheme 9:

Process 3

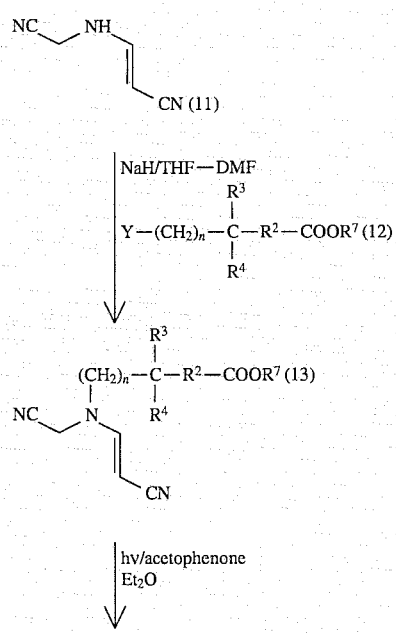

Reaction Scheme 9:
-continued

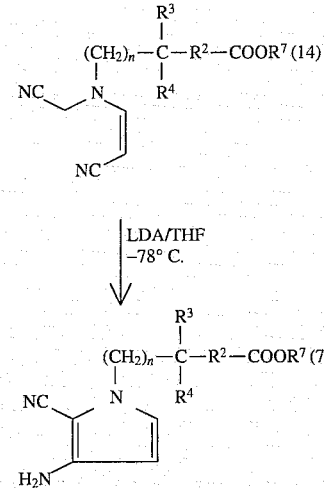

wherein $R^2$, $R^3$, $R^4$, $R^7$ and n are each as defined according to the reaction scheme 7; and Y represents a halogen atom.

The compound (11) can be prepared by reacting 3-dimethylaminoacrylonitrile with aminoacetonitrile.

The compound (11) can be converted into a compound (13) by reacting it with a compound (12) in the presence of a base [for example, an alkali metal halide or an organic base such as DBU (1,8-diazabicyclo[5,4,0]undec-7-ene), DBN (1,5-diadabicyclo[4,3,0]non-5-ene) or DMAP (4-dimethylaminopyridine)] at room temperature or under heating. The compound (13) can be further converted into a compound (14) by irradiating it with ultraviolet light in the presence of a photosensitizer (such as methyl naphthyl ketone or acetophenone) in a suitable solvent to isomerize it. The compound (14) can be easily converted into the compound (7) in the presence of a proton-abstracting reagent such as sodium alkoxide, LDA (lithium diisopropylamide) or lithium hexamethylenedisilazane through ring closure.

The compound (9) to be used in the Process 2 as a raw material for the preparation of a compound represented by the formula (6) wherein $R^1$ is a hydroxyl group can be prepared by, e.g., the following process 4 shown in the reaction scheme 10:

Reaction Scheme 10:

Process 4

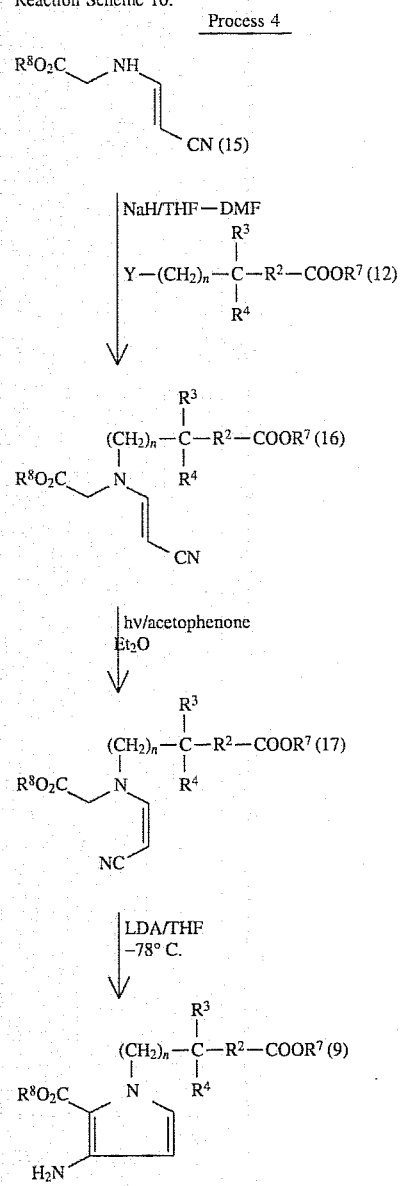

wherein $R^2$, $R^3$, $R^4$, $R^7$, $R^8$, n and Y are each as defined according to the reaction schemes 7 to 9.

A compound (15) can be prepared by reacting 3-dimethylaminoacrylonitrile with aminoacetic acid. The compound (15) can be converted into the compound (9) through Compounds (16) and (17) in a similar manner to that of the Process 3.

Among the compounds (12) which are used as the other raw material for the preparation of the compounds (7) and (9), a compound (12a) represented by the formula (12) wherein $R^3$ is a hydrogen atom and n is can be prepared by the following process 5 shown in the reaction scheme 11:

Reaction Scheme 11:

Process 5

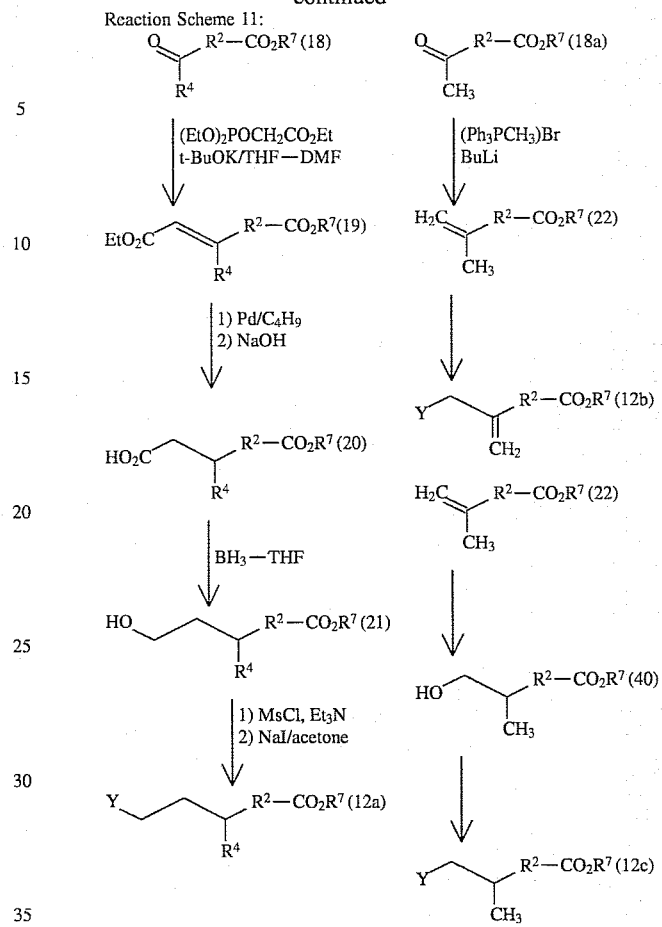

wherein $R^2$, $R^4$, $R^7$ and Y are each as defined according to the reaction schemes 7 to 9.

A compound (19) can be prepared by dropping a trialkyl phosphonoacetate (such as trimethyl phosphonoacetate or triethyl phosphonoacetate) into an organic solvent (aprotic solvent such as dimethylformamide, ether, tetrahydrofuran or a mixture of them) containing a base (such as t-butoxypotassium/tetrahydrofuran, sodium hydride or DBN), gradually adding a compound (18) having a protected carboxyl group [including t-butoxycarbonyl-substituted benzaldehyde, t-butoxycarbonyl-substituted thienylaldehyde and t-butoxycarbonyl-substituted furanylaldehyde which correspond to the compounds represented by the formula (18) wherein $R^4$ is a hydrogen atom, and among which the last two compounds may each have the substituent at any of positions 2, 3, 4 and 5, and alkyl t-butoxycarbonylphenyl ketone, alkyl t-butoxycarbonylthienyl ketone, alkyl t-butoxycarbonylfuranyl ketone and propargyl t-butoxycarbonylphenyl ketone which correspond to the compounds represented by the formula (18) wherein $R^4$ is a hydrocarbon group)] to the resulting mixture and reacting the obtained mixture at room temperature or under heating. The compound (19) thus prepared is catalytically reduced under normal or elevated pressure into a corresponding saturated ester, which is further converted into a compound (20) having both a carboxylic acid group and a protected carboxyl group (i.e., an ester group) [for example, ω-(4-(t-butoxycarbonylphenyl)alkanoic acid, ω-(5-(t-butoxycarbonylthien- 2-yl)alkanoic acid or ω-(5-(t-butoxycarbonylfuran- 2-yl)alkanoic acid wherein the alkanoic acid moiety may be either straight-chain or branched] through alkaline hydrolysis. Then, the compound (20) is converted into a corresponding compound (21) through the reduction of the carboxyl group. The reducing agent to be used in the reduction includes borane and borane analogues (such as borane-dimethyl sulfide, boranetetrahydrofuran and 9-boracyclo[3,3,1]nonane), while the solvent to be used therein includes tetrahydrofuran and ether. The compound (21) is sulfonated (e.g., mesylated) in the presence of a base and the obtained sulfonate ester is further halogenated with an alkali halide (in an aprotic solvent under heating) to give a compound represented by the formula (12a) wherein Y is chlorine, bromine or iodine [for example, ω-(4-(t-butoxycarbonylphenyl)propyl halide, ω-(5-(t-butoxycarbonylthienyl)propyl halide or ω-(5-(t-butoxycarbonylfuranyl)propyl halide].

Further, a compound represented by the formula (18) wherein $R^4$ is a methyl group, i.e., a compound (18a) can be converted into an isopropenyl halide compound (12b) by subjecting the compound (18a) to the Wittig reaction with methyltriphenylphosphonium bromide to form an isopropenyl compound (22) and halogenating the compound (22) with NBS or NCS.

Furthermore, the compound (22) can be converted into an ω-halogenoalkyl compound (12c) by reacting the compound (22) with a boron hydride compound such as 9-borabicyclo[3,3,1]nonane, borane, dicyclohexylborane, disiamylborane or thexylborane to conduct hydroboration, treating the product with an alkaline solution of hydrogen peroxide to form a primary alcohol (40) and treating the alcohol (40) in a similar manner to that of the above conversion of (21) into (12a).

A compound represented by the formula (26) is prepared through the process 6 shown in the reaction scheme 12.

Reaction Scheme 12:
Process 6

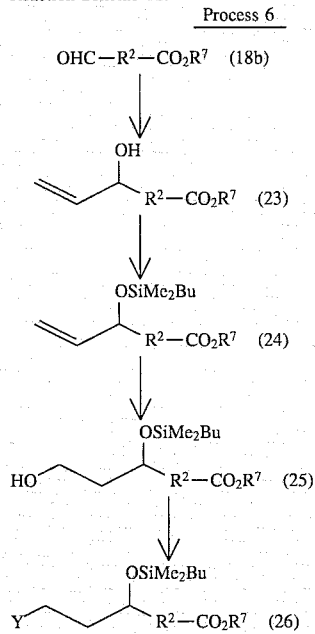

wherein $R^2$, $R^7$ and Y are each as defined according to the reaction schemes 7 to 9.

A compound represented by the formula (18) wherein $R^4$ is a hydrogen atom, i.e., a compound (18b) such as t-butoxycarbonylbenzaldehyde, t-butoxycarbonylfuranaldehyde or t-butoxycarbonylthiophenaldehyde is reacted with a vinylmagnesium halide to give an allyl alcohol (23) and this alcohol (23) is protected with, e.g., silyl ether and thereafter subjected to hydroboration to give a primary alcohol (25), which can be converted into a halide (26) in a similar manner to that described above.

The compound prepared by the reaction of the compound (11) with this halide (26) corresponds to a compound represented by the formula (13) wherein a secondary hydroxyl group is bonded to the γ-carbon atom relative to the nitrogen atom constituting the tertiary amine. This hydroxyl group can be reduced into a hydrogen atom by a known process to form a compound represented by the formula (13) wherein $R^3$ and $R^4$ are hydrogen atoms and n is 2. Further, the hydroxyl group can be also converted into an exo methylene group by oxidizing the hydroxyl group into a carbonyl group and subjecting the carbonyl group to the Wittig reaction.

A compound represented by the formula (32) is prepared through the process 7 shown in the reaction scheme 13.

Reaction Scheme 13:
Process 7

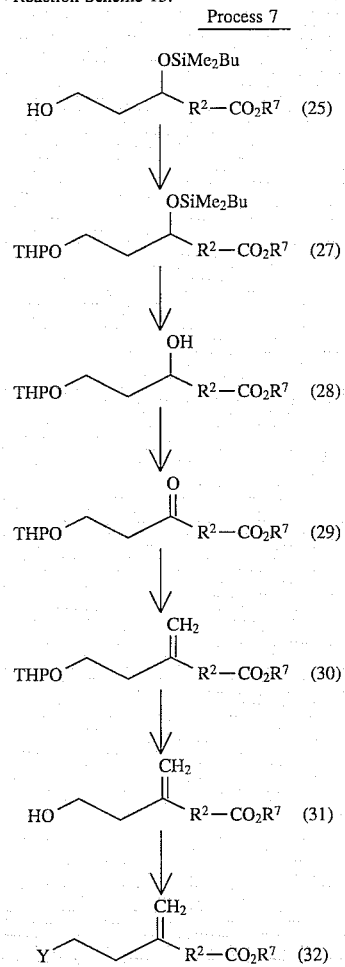

wherein $R^2$, $R^7$ and Y are each as defined according to the reaction schemes 7 to 9.

A primary alcohol (25) can be converted into a ketone (29) by reacting the alcohol (25) with 2,3-dihydrofuran or 3,4-dihydro-2H-pyran to thereby protect the primary hydroxyl group with a tetrahydrofuran-2-yl or tetrahydropyran-2-yl group, reacting the obtained protected alcohol with tetrabutylammonium bromide to deblock the secondary alcohol group and subjecting the secondary alcohol to the Swern oxidation. This ketone (29) can be further converted into a compound (32) by subjecting the ketone (29) to the Wittig reaction (with Ph₃P⁺MeBr⁻, BuLi and THF) to convert it into an exo methylene compound (30), deprotectiving the primary alcohol group of the compound (30) and treating the obtained alcohol (31) in a similar manner to that described above.

The second process for preparing a compound represented by the formula (13) wherein $R^3$ is a hydrogen atom and n is 1, which will be referred to as "compound (13a)", is described in the following process 8 shown in the reaction scheme 14:

Reaction Scheme 14:

Process 8

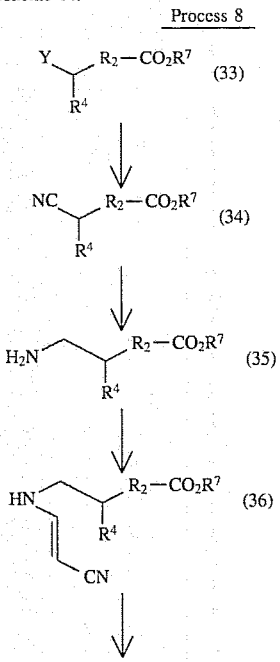

-continued
Reaction Scheme 14:
Process 8

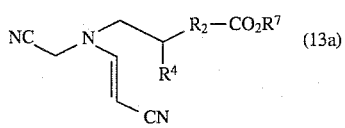

wherein $R^2$, $R^4$, $R^7$ and Y are each as defined according to the reaction schemes 7 to 9.

A compound (36) can be prepared by cyanidating a compound (33) having a halogenoalkyl group, a lower alkyl group and a protected carboxyl group (with KCN in DMSO), reducing the obtained nitrile (34) into a primary amine (35) (with BH₃ in THF) and subjecting the amine (35) to the replacement with dimethylaminoacrylonitrile (in the presence or absence of AcONa in an alcohlic solvent). The compound (36) can be converted into the compound (13a) through cyanomethylation. The compound (33) can be prepared by the bromination of a corresponding alkylate with NBS or the halogenation of a corresponding methylol-substituted derivative. The cyanomethylation of the compound (36) can be conducted by reacting it with an alkali cyanide and paraformaldehyde in acetic acid.

The third process for preparing a compound represented by the formula (13) wherein $R^3$ and $R^4$ are united to form an exo methylene group and n is 1, which will be referred to as "compound (13c)", is described in the following process 9 shown in the reaction scheme 15:

Reaction Scheme 15:

Process 9

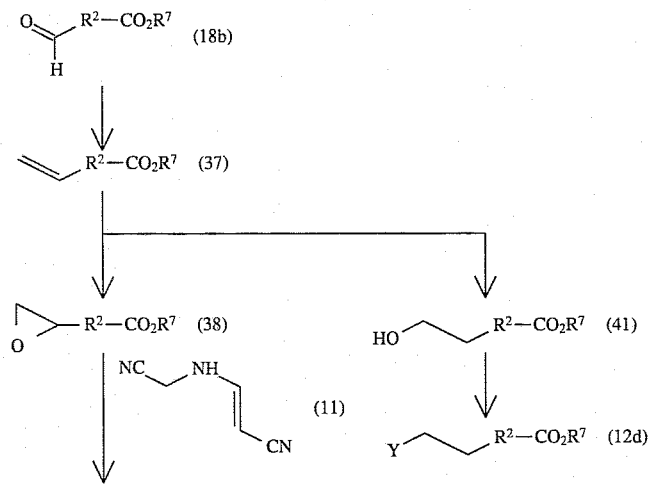

Reaction Scheme 15:

Process 9

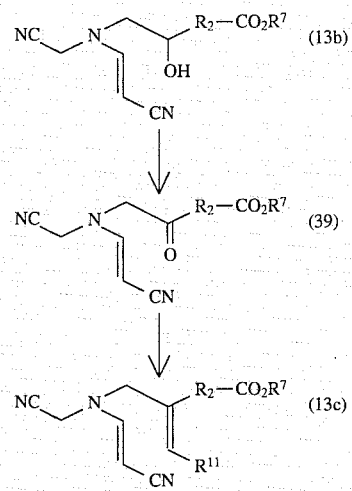

wherein $R^2$ and $R^7$ are each as defined according to the reaction schemes 7 to 9; and $R^{11}$ represents a hydrogen atom or a lower alkyl group.

This process is characterized by using an epoxy compound (38) instead of the alkyl halide (12). The carbonyl group of a compound represented by the formula (18b) (wherein $R^2$ and $R^7$ are each as defined above) can be converted into an exo methylene group through the Wittig reaction; and the exo methylene group can be converted into a hydroxyl group through hydroboration as described above; and the resulting compound can be further converted into a halogenide (12d). More specifically, the exo methylene compound (37) can be prepared through the Wittig reaction by adding the compound (18b) to a solution prepared by adding butyllithium to a suspension of methyltriphenylphosphonium bromide in tetrahydrofuran under cooling. The exo methylene compound (37) thus prepared can be converted into an ω-halogenoalkyl compound (12d) in a similar manner to that described above, i.e., by hydroborating the compound (37) with a boron hydride compound such as borane, reacting the obtained product with an alkaline solution of hydrogen peroxide to form a primary alcohol (41) and treating the alcohol (41) in a similar manner to that described above with respect to the convention of (21) into (12a). The dinitrile intermediate (13b) prepared in this case has a secondary hydroxyl group bonded to the ω-carbon atom relative to the nitrogen atom constituting the tertiary amine. The secondary hydroxyl group can be converted into a hydrogen atom by a known process. Further, the intermediate (13b) can be also converted into a compound (13c) having an alkylene side chain by oxidizing the compound (13b) into a compound (39) and subjecting the compound (39) to, e.g., the Wittig reaction.

Specific examples of the compound represented by the formula (1) according to the present invention include
N-[4-[3-(2,4-diaminopyrrolo[3,2-d]pyrimidin-5-yl)propyl]benzoyl]-L-glutamate,
N-[5-[3-(2,4-diaminopyrrolo[3,2-d]pyrimidin-5-yl)propyl]-2-thenoyl]-L-glutamate,
N-[5-[3-(2,4-diaminopyrrolo[3,2-d]pyrimidin-5-yl)propyl)-2-furoyl]-L-glutamate,
N-[4-[3-(2-amino-4-oxopyrrolo[3,2-d]pyrimidin-5-yl)propyl]benzoyl]-L-glutamate,
N-[5-[3-(2-amino-4-oxopyrrolo[3,2-d]pyrimidin-5 -yl)propyl]-2-thenoyl]-L-glutamate,
N-[5-[3-(2-amino-4-oxopyrrolo[3,2-d]pyrimidin-5-yl)propyl]-2-furoyl]-L-glutamate,
N-[4-[3-(2,4-diaminopyrrolo[3,2-d]pyrimidin-5-yl)- 1-methylpropyl]benzoyl]-L-glutamate,
N-[5-[3-(2,4-diaminopyrrolo[3,2-d]pyrimidin-5-yl)- 1-methylpropyl]-2-thenoyl]-L-glutamate,
N-[5-[3-(2,4-diaminopyrrolo[3,2-d]pyrimidin-5-yl)- 1-methylpropyl]-2-furoyl]-L-glutamate,
N-[4-[3-(2-amino-4-oxopyrrolo[3,2-d]pyrimidin- 5-yl)-1-methylpropyl]benzoyl]-L-glutamate,
N-[5-[3-(2-amino-4-oxopyrrolo[3,2-d]pyrimidin- 5-yl)-1-methylpropyl]-2-thenoyl]-L-glutamate,
N-[5-[3-(2-amino-4-oxopyrrolo[3,2-d]pyrimidin- 5-yl)-1-methylpropyl]-2-furoyl]-L-glutamate,
N-[4-[3-(2,4-diaminopyrrolo[3,2-d]pyrimidin-5-yl)- 1-methylenepropyl]benzoyl]-L-glutamate,
N-[5-[3-(2,4-diaminopyrrolo[3,2-d]pyrimidin-5-yl)- 1-methylenepropyl]-2-thenoyl]-L-glutamate,
N-[5-[3-(2,4-diaminopyrrolo[3,2-d]pyrimidin-5-yl)- 1-methylenepropyl]-2-furoyl]-L-glutamate,
N-[4-[3-(2-amino-4-oxopyrrolo[3,2-d]pyrimidin-5-yl)-1-methylenepropyl]benzoyl]-L-glutamate,
N-[5-[3-(2-amino-4-oxopyrrolo[3,2-d]pyrimidin-5-yl)-1-methylenepropyl]-2-thenoyl]-L-glutamate,
N-[5-[3-(2-amino-4-hydroxypyrrolo[3,2-d]pyrimidin- 5-yl)-1-methylenepropyl]-2-furoyl]-L-glutamate,
N-[4-[3-(2,4-diaminopyrrolo[3,2-d]pyrimidin-5-yl)- 1-ethylpropyl]benzoyl]-L-glutamate,
N-[5-[3-(2,4-diaminopyrrolo[3,2-d]pyrimidin-5-yl)- 1-ethylpropyl]-2-thenoyl]-L-glutamate,
N-[5-[3-(2,4-diaminopyrrolo[3,2-d]pyrimidin-5-yl)- 1-ethylpropyl]-2-furoyl]-L-glutamate,
N-[4-[3-(2-amino-4-oxopyrrolo[3,2-d]pyrimidin-5-yl)-1-ethylpropyl]benzoyl]-L-glutamate,
N-[5-[3-(2-amino-4-oxopyrrolo[3,2-d]pyrimidin- 5-yl)-1-ethylpropyl]-2-thenoyl]-L-glutamate,
N-[5-[3-(2-amino-4-oxopyrrolo[3,2-d]pyrimidin- 5-yl)-1-ethylpropyl]-2-furoyl]-L-glutamate,
N-[4-[2-(2,4-diaminopyrrolo[3,2-d]pyrimidin-5-yl)ethyl]benzoyl]-L-glutamate,
N-[5-[2-(2,4-diaminopyrrolo[3,2-d]pyrimidin-5-yl)ethyl]-2-thenoyl]-L-glutamate,
N-[5-[2-(2,4-diaminopyrrolo[3,2-d]pyrimidin-5-yl)ethyl]-2-furoyl]-L-glutamate, N-[4-[2-(2-amino-4-oxopyrrolo[3,2-d]pyrimidin-5-yl)ethyl]benzoyl]-L-glutamate.
N-[5-[2-(2-amino-4-oxopyrrolo[3,2-d]pyrimidin-5 -yl)ethyl]-2-thenoyl]-1-glutamate,
N-[5-[2-(2-amino-4-oxopyrrolo[3,2-d]pyrimidin-5 -yl)ethyl]-2-furoyl]-L-glutamate,
N-[4-[2-(2,4-diaminopyrrolo[3,2-d]pyrimidin-5-yl)- 1-ethylethyl]benzoyl]-L-glutamate,
N-[5-[2-(2,4-diaminopyrrolo[3,2-d]pyrimidin-5-yl)- 1-ethylethyl]-2-thenoyl]-L-glutamate,
N-[5-[2-(2,4-diaminopyrrolo[3,2-d]pyrimidin-5-yl)- 1-ethylethyl]-2-furoyl]-L-glutamate,
N-[4-[2-(2-amino-4-oxopyrrolo[3,2-d]pyrimidin-5 -yl)-1-ethylethyl]benzoyl]-L-glutamate,
N-[5-[2-(2-amino-4-oxopyrrolo[3,2-d]pyrimidin-5 -yl)-1-ethylethyl]-2-thenoyl]-L-glutamate,
N-[5-[2-(2-amino-4-oxopyrrolo[3,2-d]pyrimidin-5 -yl)-1-ethylethyl]-2-furoyl]-L-glutamate,
N-[4-[2-(2,4-diaminopyrrolo[3,2-d]pyrimidin-5-yl)-1 -methylethyl]benzoyl]-L-glutamate,
N-[5-[2-(2,4-diaminopyrrolo[3,2-d]pyrimidin-5-yl)- 1-methylethyl]-2-thenoyl]-L-glutamate,
N-[5-[2-(2,4-diaminopyrrolo[3,2-d]pyrimidin-5-yl)- 1-methylethyl]-2-furoyl]-L-glutamate,
N-[4-[2-(2-amino-4-oxopyrrolo[3,2-d]pyrimidin-5-yl)-1-methylethyl]benzoyl]-L-glutamate,
N-[5-[2-(2-amino-4-oxopyrrolo[3,2-d]pyrimidin-5 -yl)-1-methylethyl]-2-thenoyl]-L-glutamate,
N-[5-[2-(2-amino-4-oxopyrrolo[3,2-d]pyrimidin-5 -yl)-1-methylethyl]-2-furoyl]-L-glutamate,
N-[4-[2-(2,4-diaminopyrrolo[3,2-d]pyrimidin-5-yl)-1 -methyleneethyl]benzoyl]-L-glutamate,
N-[5-[2-(2,4-diaminopyrrolo[3,2-d]pyrimidin-5-yl)-1 -methyleneethyl]-2-thenoyl]-L-glutamate,
N-[5-[2-(2,4-diaminopyrrolo[3,2-d]pyrimidin-5-yl)-1 -methyleneethyl]-2-furoyl]-L-glutamate,
N-[4-[2-(2-amino-4-oxopyrrolo[3,2-d]pyrimidin-5-yl)-1 -methyleneethyl]benzoyl]-L-glutamate,
N-[5-[2-(2-amino-4-oxopyrrolo[3,2-d]pyrimidin-5-yl)-1 -methyleneethyl]-2-thenoyl]-L-glutamate and
N-[5-[2-(2-amino-4-oxopyrrolo[3,2-d]pyrimidin-5 -yl)-1-methyleneethyl]-2-furoyl]-L-glutamate.

Pharmacological Experimental Examples will now be described in order to illustrate the effects of the present invention.

EXPERIMENTAL EXAMPLE 1

Inhibitory Activity Against Dihydrofolate Reductase (DHFR)

The measurement was conducted fundamentally according to the method of D. K. Mists et al. [see Nature, 189, 39 to 42 (1961)].

DHFR was prepared from mouse leukemic cell P388 according to the method of J. M. Whiteley et al. [see Arch. Biochem. Biophys., 150, 15 to 22 (1972)].

A solution of purified DHFR was added to a solution comprising a potassium phosphate buffer solution (pH: 7.5, 75 mM), mercaptoethanol (7.5 mM) and NADPH (0.25 mM) to make up to a total amount of 0.57 ml. Each of the serial dilutions of the compound according to the present invention in an amount of 0.015 ml was added to the mixture prepared above. The mixtures thus prepared were preliminarily heated at 37° C. for 5 minutes, followed by the addition of 0.015 ml of a 25 µM solution of dihydrofolic acid. The obtained mixtures were kept at 37° C. for 5 minutes to conduct a reaction. The resulting mixtures were each examined for the decrease in the absorbency at 339 nm per minute. The amount of tetrahydrofolic acid formed was determined on the basis of the decrease and compared with that of a control solution (containing none of the compounds according to the present invention) to calculate the 50% DHFR-inhibitory concentration ($IC_{50}$). The results are given in Tables 1-A and 1-B.

TABLE 1-A

| Compound | $IC_{50} \times 10^8 M$ |
|---|---|
| Ex. 2 | 9.7 |
| Ex. 4 | 9.0 |
| Ex. 6 | 100 |
| Ex. 9 | 3.0 |

TABLE 1-B

| Compound | DHFR-inhibitory activity $IC_{50} \times 10^9 M$ |
|---|---|
| Ex. 103 | 72 |
| Ex. 105 | 4.0 |
| Ex. 108 | 7.6 |

EXPERIMENTAL EXAMPLE 2

Inhibitory Activity Against the Proliferation of Oncocyte

Mouse leukemic cell P388, mouse colonic cancer cell Colon 38, human rhinopharyngeal cancer cell KB and human lung cancer cell A549 were used as the oncocytes. The suspension of the above cancerous cells prepared with RPM1-1640 medium (10% fetal bovine serum) were each pipetted into a 96-well microplate in a predetermined amount. The microplate was placed in a carbon dioxide incubator containing 5% of $CO_2$ and incubated at 37° C. for one day. The DMSO solution of the compound according to the present invention was diluted with the culture medium to prepare the serial dilutions of the compound. These dilutions were added to the above wells in a predetermined amount. The resulting plate was cultured at 37° C. for 3 days. The number of viable cells was determined by the MTT method to determine the 50% cell proliferation-inhibitory concentration ($IC_{50}$). The number of viable cells was determined according to the method of M. C. Alley et al. [see Cancer Research, 48, 589 to 601 (1988)]. The results are given in Tables 2-A and 2-B. MTX was also tested similarly as a control compound.

TABLE 2-A

| | ($IC_{50} \times 10^8 M$) | | | | |
|---|---|---|---|---|---|
| Compound | MTX | Ex. 2 | Ex. 4 | Ex. 6 | Ex. 9 |
| P388 | 1.6 | 1.2 | 1.6 | 1.2 | 1.7 |
| A549 | 8 | 1.9 | 6.3 | 94 | 10 |
| KB | 2 | 0.98 | 3.1 | 3.0 | 3.2 |
| Colon 38 | 6 | 4.0 | 12.9 | 34 | 3.9 |

TABLE 2-B

| Compound | Proliferation-inhibitory activity $IC_{50} \times 10^9 M$ | | | |
|---|---|---|---|---|
| | MTX | Ex. 103 | Ex. 105 | Ex. 108 |
| P388 | 22 | 7.7 | 1.8 | 2.7 |
| A549 | 88 | 9.8 | 2.4 | 9.3 |
| LX-1 | — | — | 0.67 | — |
| KB | 11 | 3.8 | 0.92 | 1.6 |
| Colon 38 | 28 | 8.9 | 0.87 | 4.1 |

EXPERIMENTAL EXAMPLE 3

Test on the Activity Against Experimental Tumor Transplanted to Mouse

Mouse P388 leukemia

P388 cells ($1 \times 10^6$) were inoculated into the abdominal cavity of a female CDF1 mouse of 7 weeks of age and a test drug was administered to the mouse once a day for four days from the next day.

Each test drug was administered intraperitoneally in a state dissolved or suspended in a 4% solution of $NaHCO_3$ in physiological saline, while only a 4% solution of $NaHCO_3$ in physiological saline was administered to a control group. Each control group was composed of ten mice, while each medicated group was composed of six mice. The antitumor activity was evaluated based on the T/C value calculated according to the following formula:

T/C (%) = average survival time (day) of medicated mice ×

100/average survival time (day) of control mice

The measurement was conducted according to the method of R. I. Geran et al. (see Cancer Chemotherapy Reports (Part 3), 31 (1972)). MTX was also tested similarly as a control compound. The results are given in Tables 3-A and 3-B.

TABLE 3-A

| Compound | Dose (mg/kg) | MST | T/C (%) |
|---|---|---|---|
| Ex. 2 | 3.13 | 13.3 ± 0.47 | 148 |
| | 6.25 | 13.5 ± 0.50 | 150 |
| | 12.5 | 14.0 ± 0.71 | 156 |
| | 25.0 | 14.0 ± 0.71 | 156 |
| | 50.0 | 14.8 ± 0.83 | 164 |
| | 100.0 | 14.8 ± 0.83 | 164 |
| | 200.0 | 16.0 ± 0.82 | 178 |
| Ex. 4 | 12.5 | 13.5 ± 0.87 | 135 |
| | 50.0 | 18.5 ± 1.12 | 185 |
| Ex. 9 | 0.78 | 16.3 ± 1.02 | 181 |
| | 3.13 | 14.8 ± 0.83 | 164 |
| | 12.5 | 14.0 ± 0.71 | 156 |
| | 50.0 | 15.0 ± 0.71 | 167 |
| MTX | 0.78 | 12.5 ± 1.12 | 139 |
| | 1.56 | 13.8 ± 0.83 | 153 |
| | 3.13 | 15.5 ± 0.50 | 172 |
| | 6.25 | 15.5 ± 1.20 | 172 |
| | 12.5 | 9.3 ± 2.9 | 103 |

TABLE 3-B

| Compound | Dose (mg/kg) | T/C (%) |
|---|---|---|
| Ex. 103 | 0.78 | 129 |
| | 3.13 | 135 |
| | 12.5 | 147 |
| | 50 | 148 |

TABLE 3-B-continued

| Compound | Dose (mg/kg) | T/C (%) |
|---|---|---|
| Ex. 105 | 0.05 | 126 |
| | 0.20 | 151 |
| | 0.78 | 176 |
| | 3.13 | 151 |
| Ex. 108 | 0.20 | 133 |
| | 0.78 | 150 |
| | 3.13 | 170 |
| | 12.5 | 143 |
| MTX | 0.78 | 121 |
| | 1.56 | 137 |
| | 3.13 | 151 |
| | 6.25 | 162 |
| | 12.5 | 162 |

It can be understood from the results of the above Experimental Examples that the compound of the present invention exhibits an inhibitory activity against dihydrofolate reductase (DHFR) to remarkably inhibit the proliferation of mouse leukemic cell P388, mouse colonic cancer cell Colon 38, human nonparvicellular lung cancer cell A549 and human epidermal carcinoma cell KB.

Further, it can be also understood that the compound of the present invention has a life-prolonging effect or a therapeutic effect of inhibiting the proliferation of tumoral tissues on a mouse to which leukemic cells or certain solid tumor cells have been transplanted, so that the compound of the present invention is expected to be effectively utilized in the treatment or maintenance therapy of human tumors. Specifically, the compound of the present invention can be used either alone or together with other antitumor drug in the treatment or maintenance therapy of various tumors, the treatment of which has been conducted with MTX, for example, choriocarcinoma, leukemia, adenocarcinoma of female chest, epidermal carcinoma of head or neck, squamocellular or parvicellular lung cancer or various lymphosarcomas.

One of the characteristics of the compound according to the present invention is that it is less toxic than MTX, exhibits a remarkable effect as a drug in the antitumor activity test and the range of its effective dose is wide. Further, the compound of the present invention is generally also less toxic than the above-mentioned pyrrolo[3,2-d] pyrimidine compound reported by Miwa et al. The minimum effective dose of the compound of the present invention against MTX-sensitive tumor and that of MTX are nearly of the same order. However, the ratio of the maximum effective dose to the minimum one in the application of the compound of the present invention to a tumor bearing mouse (CDF1) is higher than that in the application of MTX thereto. Precisely, the ratios with respect to the compounds of Examples 2 and 9 were both several tens (about 60), though that with respect to MTX was a little under 10.

When the compounds of the present invention are used as drugs, they may be each administered orally or parenterally either as such or as a pharmacologically acceptable carboxylic salt or acid-addition salt. The dose thereof varies depending upon the symptom; the weight, age, sex and sensitivity of a patient; the method (route) and interval (schedule) of administration; the kind of an active ingredient; the kind and properties of preparation and so forth and is not particularly limited. Generally, the dose thereof per subject (60 kg, 1.62 $m^2$/man) a day is 1 to 2000 mg, preferably 10 to 1000 mg or 1 to 300 mg, particularly perferably 10 to 150 mg, which may be administered once a day continuously or 1 to 3 times a week intermittently.

A preparation for oral administration according to the present invention is prepared by adding a filler and, if necessary, a binder, disintegrator, lubricant, color and/or corrigent to an active ingredient and formulating the obtained mixture into a tablet, buccal, troche, granule, powder, capsule, suspension or syrup. It is convenient that the active ingredient to filler ratio (%) of each administration unit lies within a range of about 0.5 to 50% by weight and when the ratio lies within this range, a favorable dose can be attained.

Examples of the filler include lactose, corn starch, sucrose, glucose, sorbitol, crystalline cellulose and silicon dioxide; those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant include magnesium stearate, talc, polyethylene glycol, silica and hardened vegetable oil; those of the color include those authorized as pharmaceutical additives; and those of the corrigent include cocoa powder, mentha herb, aromatic powder, mentha oil, borneol and powdered cinnamon bark. Of course, the tablet and granule may be suitably coated with sugar, gelatin or the like, if necessary.

The preparation for parenteral administration includes injection, dispersion and emulsion. An injection according to the present invention is prepared by adding a pH modifier, buffer, suspending agent, solubilizing agent, stabilizer, tonicity agent and/or preservative to an active ingredient at need and formulating the mixture into an injection for intravenous, subcutaneous or intramuscular administration by the conventional process.

The injection includes sterile aqueous solution and dispersion and sterile powder for injection preparation before use. The carrier may be a solvent containing water, ethanol, glycerol, polyol, a mixture of two or more of them or a vegetable oil. The dispersion can be prepared by dispersing the compound in an aqueous or oily medium containing glycerol, liquid polyethylene glycol or a mixture of them. The sterile powder for injection preparation before use is preferably prepared by subjecting a sterile filtrate containing the compound to vacuum concentration/drying or freeze drying.

Examples of the suspending agent include methylcellulose, Polysorbate 80, hydroxyethylcellulose, acacia, tragacanth powder, carboxymethylcellulose sodium and polyoxyethylene sorbitan monolaurate.

Examples of the solubilizing agent include polyoxyethylene hardened castor oil, Polysorbate 80, nicotinamide, polyoxyethylene sorbitan monolaurate, Macrogol and ethyl ester of castor oil fatty acid.

Examples of the stabilizer include sodium sulfite, sodium metasulfite and ether and those of the preservative include methyl p-hydroxybenzoate, ethyl p-hydroxybenzoate, sorbic acid, phenol, cresol and chlorocresol.

EXAMPLE

The present invention will now be described more specifically by referring to the following Preparative Examples and Examples, though the present invention is not limited by them.

PREPARATIVE EXAMPLE 1

3-(N-Cyanomethyl)aminoacrylonitrile

[compound (11)]

Aminoacetonitrile hydrochloride (26.5 g, 0.28 mol), sodium acetate (34.8 g, 0.42 mol) and 3-dimethylaminoacrylonitrile (13.8 g, 0.1 mol) were added to a mixture comprising methanol (300 ml) and water (20 ml). The obtained mixture was stirred at room temperature for 24 hours, followed by the addition of water. The resulting mixture was extracted with ethyl acetate. The organic layer was distilled to remove the solvent. The obtained residue was subjected to silica gel column chromatography and eluted with a solvent (ethyl acetate/hexane=1:1) to give 9.3 g of the title compound (63%).

NMR (CDCl$_3$) δ(ppm): 4.0 (2H×⅔, d, J=7Hz, N—CH$_2$—CN, E isomer), 4.14 (2H×⅓+1H×⅓, m, N—CH$_2$—CN, olefinic proton, Z isomer), 4.3 (1H×⅔, d, J=17 Hz, olefinic proton, E isomer), 6.6 (1H×⅓, dd, J=11 Hz, 2 Hz, olefinic proton, Z isomer), 7.5 (1H×⅔, dd, J=17 Hz, 8 Hz, olefinic proton, E isomer).

PREPARATIVE EXAMPLE 2 t-Butyl 4-(3-iodopropyl)benzoate

[a compound represented by the formula (12) wherein n is 2, $R^2$ is a phenylene group, $R^3$ is H, $R^4$ is H, $R^7$ is t-Bu and Y is I]

Potassium t-butoxide (8.4 g, 0.075 mol) was added to a solution of ethyl diethylphosphonoacetate (19 ml, 0.075 mol) in THF (200 ml) and the obtained mixture was stirred at room temperature for 30 minutes, followed by the addition of a solution of t-butyl p-formylbenzoate (10.3 g, 50 mmol) in THF (20 ml). The obtained mixture was stirred at room temperature for 30 minutes and poured into a saturated aqueous solution of ammonium chloride. The obtained mixture was extracted with ether. The organic layer was distilled to remove the solvent and the residue was subjected to silica gel column chromatography and eluted with a solvent (ethyl acetate/hexane=1:10) to give ethyl 4-(t-butoxycarbonyl)phenylacrylate. This product was catalytically reduced with 10% palladium-carbon (0.5 g) in methanol (200 ml) and thereafter added to a mixture comprising a 1N aqueous solution of sodium hydroxide (100 ml) and methanol (100 ml). The obtained mixture was stirred at room temperature for 2 hours. After the completion of the reaction, the reaction mixture was made weakly acidic with 1N aqueous hydrochloric acid and extracted with ethyl acetate. The organic layer was distilled to remove the solvent and the residue was purified by short silica gel column chromatography to give 4-(t-butoxycarbonyl)phenylpropionic acid. This acid was dissolved in THF (100 ml), followed by the dropwise addition of a 1M solution of BH$_3$ in THF (100 ml) under cooling with ice. The obtained mixture was stirred at room temperature for one hour. After the completion of the reaction, the reaction mixture was poured into a saturated aqueous solution of ammonium chloride and the obtained mixture was extracted with ethyl acetate. The organic layer was distilled to remove the solvent and the residue was subjected to silica gel column chromatography and eluted with a solvent (ethyl acetate/hexane=1:1) to give 4-(t-butoxycarbonyl)phenylpropanol. This product was dissolved in ether (300 ml), followed by the addition of triethylamine (21 ml) and methanesulfonyl chloride (5.8 ml) under cooling with ice. The obtained mixture was stirred for 30 minutes. After the completion of the reaction, the reaction mixture was poured into a saturated aqueous solution of ammonium chloride and the obtained mixture was extracted with ether. The organic layer was distilled to remove the solvent, giving 4-(t-butoxycarbonyl)phenylpropyl mesylate. This product was dissolved in acetone (300 ml), followed by the addition of sodium iodide (30 g). The obtained mixture was heated under reflux for one hour. After the completion of the reaction, the reaction mixture was poured into a saturated aqueous solution of ammonium chloride and the obtained mixture was extracted with ether. The organic layer was distilled to remove the solvent. The residue was subjected to silica gel column chromatography and eluted with a solvent (ether/hexane=1:10) to give 14.5 g of the title compound as a colorless oil (84%).

NMR (CDCl$_3$) δ(ppm): 2.06–2.15 (2H, m, I—CH$_2$—CH$_2$—CH$_2$—Ar), 2.76 (2H, t, J=7.2Hz, I—CH$_2$—CH$_2$—CH$_2$—Ar), 3.14 (2H, t, J=7.2Hz, I—CH$_2$—CH$_2$—CH$_2$—Ar), 7.24 (2H, d, J=8.4Hz, ArH), 7.92 (2H, d, J=8.4Hz, ArH).

PREPARATIVE EXAMPLE 3 t-Butyl 4-[3-(3-amino-2-cyanopyrrol-1-yl)propyl]benzoate

[a compound represented by the formula (7) wherein n is 2, $R^2$ is a phenylene group, $R^3$ is H, $R^4$ is H and $R^7$ is t-Bu]

The 3-(N-cyanomethyl)aminoacrylonitrile (1 g, 9.3 mmol) prepared in the Preparative Example 1 was dissolved in a mixture comprising THF (20 ml) and DMF (4 ml), followed by the addition of 60% sodium hydride (0.45 g) under cooling with ice. The obtained mixture was stirred, followed by the dropwise addition of a solution of the t-butyl 4-(3-iodopropyl)benzoate (3.2 g) prepared in the Preparative Example 2 in THF (10 ml). The obtained mixture was stirred at room temperature for one hour to complete a reaction. The reaction mixture was poured into a saturated aqueous solution of ammonium chloride. The obtained mixture was extracted with ethyl acetate. The organic layer was distilled to remove the solvent. The residue was subjected to silica gel column chromatography and eluted with a solvent (ethyl acetate/hexane=1:2) to give 2.5 g of (E)-t-butyl 4-[3-(N-cyanomethyl-N-p-cyanovinylamino)propyl]benzoate.

NMR (CDCl$_3$) δ(ppm) 1.56 (9H, s, t-Bu), 1.87–1.97 (2H, m, N—CH$_2$—CH$_2$—CH$_2$—Ar), 2.64 (2H, t, J=7.2Hz, N—CH$_2$—CH$_2$—CH$_2$—Ar), 3.17 (2H, t, J=7.2Hz, N—CH$_2$—CH$_2$—CH$_2$—Ar), 3.94 (2H, s, N—CH$_2$—CN), 4.0 (1H, d, J=18Hz, NC—CH=CH—N), 6.85 (1H, d, J=18Hz, NC—CH=CH—N), 7.21 (2H, d, J=8Hz, ArH), 7.92 (2H, d, J=8Hz, ArH).

Then, the E isomer was dissolved in ether. The obtained solution was irradiated with light (from a high-pressure mercury lamp) in the presence of acetophenone (2.0 ml) for 4 hours. The reaction mixture was distilled to remove the solvent. The residue was subjected to silica gel column chromatography and eluted with a solvent (ether/hexane= 2:1) to thereby isolate (Z)-t-butyl 4-[3-(N-cyanomethyl-N-p-cyanovinylamino)propyl]benzoate (1.0 g).

NMR (CDCl$_3$) δ(ppm): 1.57 (9H, s, t-Bu), 1.97–2.05 (2H, m, N—CH$_2$—CH$_2$—CH$_2$—Ar), 2.71 (2H, t, J=7.2Hz, N—CH$_2$CH$_2$—CH$_2$—Ar), 3.39 (2H, t, J=7.2Hz, N—CH$_2$—CH$_2$—CH$_2$—Ar), 3.93 (1H, d, J=10Hz, NC—CH=CH—N), 4.25 (2H, s, N—CH$_2$—CN), 6.23 (1H, d, J=10Hz, NC—CH=CH—N), 7.24 (2H, d, J=8Hz, ArH), 7.91 (2H, d, J=8Hz, ArH).

This Z isomer (1.0 g) was dissolved in THF (50 ml), followed by the dropwise addition of a solution of LDA (3.75 mmol) in THF at −78° C. The obtained mixture was stirred to complete a reaction. A saturated aqueous solution of ammonium chloride was added to the reaction mixture. The obtained mixture was extracted with ether and the organic layer was distilled to remove the solvent. The residue was subjected to silica gel column chromatography and eluted with a solvent (ether/hexane=1:1) to give the title compound (1 g, 33%).

NMR (CDCl$_3$) δ(ppm): 1.6 (9H, s, t-Bu), 2.08–2.17 (2H, m, N—CH$_2$—CH$_2$—CH$_2$—Ar), 2.64 (2H, t, J=7.2Hz, N—CH$_2$CH$_2$CH$_2$—Ar), 3.86 (2H, t, J=7.2Hz, N—CH$_2$—CH$_2$—CH$_2$—Ar), 5.64 (1H, d, J=3Hz, pyrrole 4-H), 6.51 (1H, d, J=3Hz, pyrrole 5-H), 7.21 (2H, d, J=8Hz, ArH), 7.91 (2H, d, J=8Hz, ArH)

MS: FAB-MS m/z: 325(M$^+$).

EXAMPLE 1 t-Butyl 4-[3-(2,4-diaminopyrrolo[3,2-d]pyrimidin-5-yl)propyl]benzoate

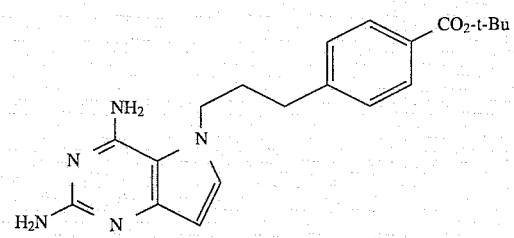

[a compound represented by the formula (6) wherein n is 2, $R^1$ is NH$_2$, $R^2$ is a phenylene group, $R^3$ is H, $R^4$ is H and $R^7$ is t-Bu]

The t-butyl 4-[3-(3-amino-2-cyanopyrrol-1 -yl)propyl]benzoate (2.35 g, 7.2 mmol) prepared in the Preparative Example 3 was dissolved in methylene dichloride (30 ml), followed by the dropwise addition of benzoyl isothiocyanate (1.14 ml, 8.6 mmol) under cooling with ice. The obtained mixture was stirred under cooling with ice for one hour and distilled to remove the solvent. The residue was subjected to silica gel column chromatography and eluted with a solvent (ether/hexane=1:1) to give a thiourea. This thiourea was dissolved in methylene dichloride (70 ml), followed by the addition of DBN (1.07 ml, 8.6 mmol) and methyl iodide (1.34 ml, 21.6 mmol). The obtained mixture was stirred at room temperature for one hour to complete a reaction. The reaction mixture was poured into water and the obtained mixture was extracted with methylene dichloride. The organic layer was distilled to remove the solvent and the residue was subjected to silica gel column chromatography and eluted with a solvent (ether/hexane=1:1) to give an S-methylthiourea compound. This compound was dissolved in 50 ml of a methanolic solution of ammonia (prepared by saturating methanol with ammonia under cooling with ice) and the obtained solution was heated at 90° C. in an autoclave for 24 hours. After the completion of the reaction, the reaction mixture was concentrated and the obtained residue was subjected to silica gel column chromatography and eluted with a solvent (ethyl acetate/hexane=1:1) to give t-butyl 4-[3-(4-amino- 2-methylthiopyrrolo[3,2-d]pyrimidin-5-yl)propyl]-benzoate. Further, the elution with another solvent (ethyl acetate/methanol/acetic acid=8:1:1) gave the title compound (1.32 g, 50%).

NMR (CD$_3$OD+CDCl$_3$) δ(ppm): 1.58 (9H, s, t-Bu), 2.07–2.17 (2H, m, N—CH$_2$—CH$_2$—CH$_2$—Ar), 2.62 (2H, t, J=7.2Hz, N—CH$_2$CH$_2$—CH$_2$—Ar), 4.25 (2H, t, J=7.2Hz, N—CH$_2$—CH$_2$—CH$_2$—Ar), 6.08 (1H, d, J=3Hz, 7-H), 7.18 (1H, d, J=3Hz, 6-H), 7.23 (2H, d, J=8Hz, ArH), 7.88 (2H, d, J=8Hz, ArH)

MS: FAB-MS m/z: 368 (M+H$^+$).

EXAMPLE 2

N-[4-[3-(2,4-Diaminopyrrolo[3,2-d]pyrimidin-5-yl) propyl]benzoyl]-L-glutamate

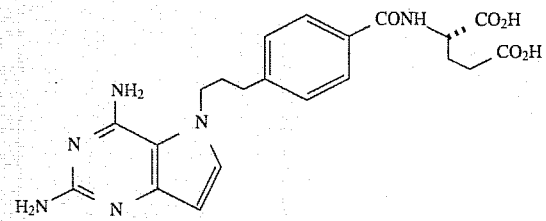

[a compound represented by the formula (1) wherein n is 2, R$^1$ is NH$_2$, R$^2$ is a phenylene group, R$^3$ is H and R$^4$ is H]

The t-butyl 4-[3-(2,4-diaminopyrrolo[3,2-d]pyrimidin-5-yl)propyl]benzoate (1 g, 2.7 mmol) prepared in the Example 1 was added to a mixture comprising dioxane (50 ml) and 1N aqueous hydrochloric acid (50 ml). The obtained mixture was stirred at 90° C. for one hour. After the completion of the reaction, the reaction mixture was concentrated, subjected to silica gel column chromatography and eluted with a solvent (ethyl acetate/methanol/acetic acid=7:1:1) to give 0.81 g of 4-[3-(2,4 -diaminopyrrolo[3,2-d]pyrimidin-5-yl) propyl]benzoic acid. This acid, diethyl L-glutamate hydrochloride (1.61 g) and diphenylphosphoryl azide (DPPA) (1.65 ml) were added to DMF (35 ml), followed by the dropwise addition of triethylamine (2.2 ml) under cooling with ice. The obtained mixture was stirred under cooling with ice and thereafter at room temperature for 4 hours. After the completion of the reaction, the reaction mixture was concentrated, subjected to silica gel column chromatography and eluted with a solvent (ethyl acetate/methanol/ acetic acid=8:1:1) to give an amide compound. This amide compound was dissolved in methanol (15 ml), followed by the dropwise addition of 1N aqueous sodium hydroxide (30 ml). The obtained mixture was stirred at room temperature for 5 hours and neutralized with 1N aqueous hydrochloric acid. The resulting reaction mixture was concentrated, subjected to silica gel column chromatography and eluted with a solvent (ethyl acetate/methanol/acetic acid=5:1:1). The obtained solid was washed with ethanol and a small amount of methanol to give a pale-yellow crystalline product (0.72 g). This product was recrystallized to give 0.35 g of the title compound (28%).
m.p. 189°–193° C.
mol. form. C$_{21}$H$_{24}$N$_6$O$_5$.5/4H$_2$O

| elem. anal. | |
|---|---|
| calculated (%) | found (%) |
| C 54.48 | C 54.64 |
| H 5.77 | H 5.55 |
| N 18.15 | N 17.87 |

MS: FAB-MS m/z: 441 (M+H$^+$)
NMR (DMSO-d$_6$+CDCl$_3$) δ(ppm): 1.9–2.07 (4H, m, 9-CH$_2$, 21-CH$_2$), 2.25 (2H, t, J=7.2Hz, 22-CH$_2$), 4.2–4.4 (3H, m, 8-CH$_2$, 19-CH), 6.01 (1H, d, J=3Hz, 7-CH), 7.20 (2H, d, J=8Hz, 12-CH, 16-CH), 7.32 (1H, d, J=3Hz, 6-H), 7.78 (2H, d, J=8Hz, 13-CH, 15-CH).

PREPARATIVE EXAMPLE 4 t-Butyl 4-(3-iodo-1-methylpropyl)benzoate

[a compound represented by the formula (12) wherein n is 2, R$^2$ is a phenylene group, R$^3$ is H, R$^4$ is Me, R$^7$ is t-Bu and Y is I]

The same procedure as that of the Preparative Example 2 was repeated except that t-buyl p-acetylbenzoate (10 g, 48 mmol) was used as the starting material. 8.5 g of the title compound was obtained (49%).

NMR (CDCl$_3$) δ(ppm): 1.28 (3H, d, J=7.2Hz, —Me), 1.58 (9H, s, t-Bu), 2.06–2.13 (2H, m, I—CH$_2$—CH$_2$—CH—Ar), 2.87–2.98 (2H, m, I—CH$_2$—CH$_2$—CH—Ar), 3.05–3.12 (1H, m, I—CH$_2$—CH$_2$—CH—Ar), 7.25 (2H, d, J=8Hz, ArH), 7.93 (2H, d, J=8Hz, ArH).

PREPARATIVE EXAMPLE 5

(E)-t-Butyl 4-[4-(N-cyanomethyl)-N-β-cyanovinylamino] butan-2-yl]benzoate

[a compound represented by the formula (13) wherein n is 2, R$^2$ is a phenylene group, R$^3$ is H, R$^4$ is Me and R$^7$ is t-Bu]

The N-alkylation of 3-(N-cyanomethyl)aminoacrylonitrile (2.57 g, 24 mmol) with the t-butyl 4-(3-iodo- 1-methylpropyl)benzoate (8.5 g, 24 mmol) prepared in the Preparative Example 4 was conducted in a similar manner to that of the Preparative Example 3. 6.5 g of the title compound was obtained (81%).

NMR (CDCl$_3$) δ(ppm): 1.31 (3H, d, J=7.2Hz, Me), 1.60 (9H, s t-Bu), 1.87–2.04 (2H, m, N—CH$_2$—CH$_2$—CH—Ar), 2.73–2.82 (1H, m, N—CH$_2$—CH$_2$—CH—Ar), 3.01–3,14 (2H, m, N—CH$_2$=CH$_2$—CH—Ar), 3.87 (2H, s, N—CH$_2$—CN)., 3.95 (1H, d, J=14Hz, N—CH=CH—CN), 6.73 (1H, d, J=14Hz, N—CH=CH—CN), 7.22 (2H, d, J=8Hz, ArH), 7.97 (2H, d, J=8Hz, ArH).

PREPARATIVE EXAMPLE 6 t-Butyl 4-[3-(3-amino-2-cyanopyrrol-1-yl)-1-methylpropyl] benzoate

[a compound represented by the formula (7) wherein n is 2, R$^2$ is a phenylene group, R$^3$ is H, R$^4$ is Me and R$^7$ is t-Bu]

The (E)-t-butyl 4-[4-(N-cyanomethyl)-N-β-cyanovinylamino]butan-2-yl]benzoate (4.5 g) prepared in the Preparative Example 5 was converted into (Z)-t-butyl 4-[4-(N-cyanomethyl)-N-β-cyanovinylamino]butan-2-yl]benzoate through photoisomerization according to the same procedure as that of the Preparative Example 3.

NMR (CDCl$_3$) δ(ppm): 1.31 (3H, d, J=7.2Hz, Me), 1.58 (9H, s, t-Bu), 1.92–2.09 (2H, m N—CH$_2$—CH$_2$—CH—Ar), 2.81–3.37 (3H, m, N—CH$_2$—CH$_2$—CH—Ar), 3.94 (1H, d, J=10Hz, N—CH=CH—CN), 4.19 (2H, q, N—CH$_2$CN), 6.07 (1H, d, J=10Hz, N—CH=CH—CN), 7.24 (2H, d, J=8Hz, ArH), 7.94 (2H, d, J=8Hz, ArH).

The obtained Z isomer was treated in a similar manner to that of the Preparative Example 3 to give 1.5 g of the title compound through ring closure (33%).

NMR (CDCl$_3$) δ(ppm): 1.26 (3H, d, J=7.2Hz, Me), 1.58 (9H, s t-Bu). 2.01–2.19 (2H, m, N—CH$_2$—CH$_2$—CH—Ar), 2.64–2.74 (1H, m, N—CH$_2$—CH$_2$—CH—Ar), 3.57–3.78 (4H, m, N—CH$_2$—CH$_2$—CH—Ar, NH$_2$), 5.58 (1H, d, J=3Hz, pyrrole 4-H), 6.37 (1H, d, J=3Hz, pyrrole 5-H), 7.21 (2H, d, J=8Hz, ArH), 7.94 (2H, d, J=8Hz, ArH).

EXAMPLE 3 t-Butyl 4-[2-(2,4-diaminopyrrolo[3,2-d]pyrimidin-5-yl)-1-methylpropyl]benzoate

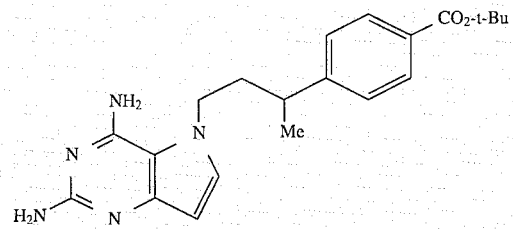

[a compound represented by the formula (6) wherein n is 2, $R^1$ is $NH_2$, $R^2$ is a phenylene group, $R^3$ is H, $R^4$ is Me and $R^7$ is t-Bu]

The t-butyl 4-[3-(3-amino-2-cyanopyrrol-1-yl)-1-methylpropyl]benzoate (1.5 g, 4.4 mmol) prepared in the Preparative Example 6 was treated according to the same procedure as that of the Example 1. 0.85 g of the title compound was obtained through ring closure (52%).

NMR (CD$_3$OD+CDCl$_3$) δ(ppm): 1.33 (3H, d, J=7.2Hz, Me), 1.64 (9H, s, t-Bu), 2.13–2.27 (2H, m, N—CH$_2$—CH$_2$—CH—Ar), 2.73–2.82 (1H, m, N—CH$_2$—CH$_2$—CH—Ar), 4.21–4.32 (2H, m, N—CH$_2$—CH$_2$—CH—Ar), 6.17 (1H, d, J=3Hz, 7-H), 7.25 (1H, d, J=3Hz, 6-H), 7.32 (2H, d, J=8Hz, ArH), 7.93 (2H, d, J=8Hz, ArH).

EXAMPLE 4

N-[4-[3-(2,4-Diaminopyrrolo[3,2-d]pyrimidin-5-yl)-1-methylpropyl]benzoyl]-L-glutamate

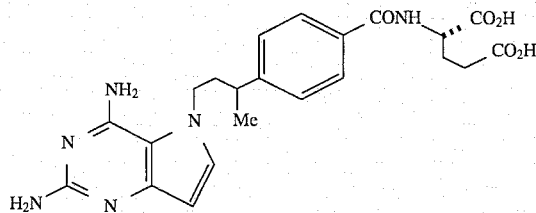

[a compound represented by the formula (1) wherein n is 2, $R^1$ is $NH_2$, $R^2$ is a phenylene group, $R^3$ is H and $R^4$ is Me]

The t-butyl 4-[2-(2,4-diaminopyrrolo[3,2-d]pyrimidin-5-yl)-1-methylpropyl]benzoate (0.85 g, 2.3 mmol) prepared in the Example 3 was converted into the title compound (0.5 g, 48%) by the same procedure as that of the Example 2, i.e., by hydrolyzing the ester with acid, condensing the obtained free acid with diethyl L-glutamate hydrochloride into an amide compound and hydrolyzing the ethyl ester moieties of the amide compound.

mol. form. $C_{22}H_{26}N_6O_5 \cdot 5/2H_2O$

NMR (CD$_3$OD+CDCl$_3$) δ(ppm): 1.32 (3H, d, J=7.2Hz, Me), 2.02–2.57 (6H, m, —CH$_2$—CH$_2$—CO$_2$H, N—CH$_2$CH$_2$CH—Ar), 4.21–4.39 (2H, m, N—CH$_2$=CH$_2$—CH—Ar), 4.63–4.67 (1H, m, CONHCH—CO$_2$H), 6.13 (1H, d, J=3Hz, 7-H), 7.24 (1H, d, J=3Hz, 6-H), 7.26–7.31 (2H, m, ArH), 7.78–7.83 (2H, m, ArH).

MS: FAB-MS m/z: 455(M+H)$^+$.

PREPARATIVE EXAMPLE 7 t-Butyl 4-(3-iodo-1-ethylpropyl)benzoate

[a compound represented by the formula (12) wherein n is 2, $R^2$ is a phenylene group, $R^3$ is H, $R^4$ is Et, $R^7$ is t-Bu and Y is I]

t-Butyl p-formylbenzoate (20 g, 97 mmol) was dissolved in ether (300 ml), followed by the dropwise addition of ethylmagnesium bromide.(3M ethereal solution, 33 ml) under cooling with ice. The obtained mixture was stirred. After the completion of the reaction, the reaction mixture was poured into a saturated aqueous solution of ammonium chloride and the obtained mixture was extracted with ether. The organic layer was distilled to remove the solvent. The residue was subjected to silica gel column chromatography and eluted with a solvent (ethyl acetate/hexane=1:4) to give 22.3 g of t-butyl 4-(1-hydroxypropyl)benzoate. This product was dissolved in petroleum ether (500 ml), followed by the addition of active manganese dioxide (165 g). The obtained mixture was heated under reflux for 30 hours. After the completion of the reaction, the reaction mixture was filtered and the filtrate was concentrated to give 21.1 g of a propiophenone compound (corresponding to a compound represented by the formula (18) wherein $R^4$ is Et and $R^7$ is t-Bu). Then, this compound was subjected to the Horner-Emmons reaction. That is, potassium t-butoxide (19 g) was added to a solution of ethyl diethylphosphonoacetate (36 ml) in THF (400 ml). The obtained mixture was stirred at room temperature for 30 minutes, followed by the addition of a solution of the propiophenone compound (21.1 g) in THF (40 ml). The obtained mixture was stirred at 55 to 65° C. for 1.5 hours. After the completion of the reaction, the reaction mixture was poured into a saturated aqueous solution of ammonium chloride to give 22.7 g of an α,β-unsaturated ester compound (corresponding to a compound represented by the formula (19) wherein $R^4$ is Et and $R^7$ is t-Bu). This ester compound was catalytically reduced with 10% palladium-carbon (0.5 g) in methanol (300 ml) and added to a mixture comprising 1N aqueous sodium hydroxide (150 ml) and methanol (150 ml). The obtained mixture was stirred at room temperature for 2 hours. After the completion of the reaction, the reaction mixture was made weakly acidic with 1N aqueous hydrochloric acid and extracted with ethyl acetate. The organic layer was distilled to remove the solvent and the residue was purified by short silica gel column chromatography to give 17.7 g of 3-[p-(t-butoxycarbonyl)phenyl]-3-ethylpropionic acid. This acid was dissolved in THF (200 ml), followed by the dropwise addition of a 1M solution of BH$_3$ in THF (80 ml) under cooling with ice. The obtained mixture was stirred at room temperature for one hour. After the completion of the reaction, the reaction mixture was poured into a saturated aqueous solution of ammonium chloride and the obtained mixture was extracted with ethyl acetate. The organic layer was distilled to remove the solvent and the residue was subjected to silica gel column chromatography and eluted with a solvent (ethyl acetate/hexane=1:1) to give 16.7 g of t-butyl 4-(3-hydroxy-1-ethylpropyl)benzoate. This product was dissolved in ether (400 ml), followed by the addition of triethylamine (44 ml) and methanesulfonyl chloride (9.8 ml) under cooling with ice. The obtained mixture was stirred to complete a reaction. The reaction mixture was poured into a saturated aqueous solution of ammonium chloride and the obtained mixture was extracted with ether. The organic layer was distilled to remove the solvent, by which a mesylate was obtained. This mesylate was dissolved in acetone (400 ml), followed by the addition of sodium iodide (40 g). The obtained mixture was heated under reflux. After the completion of the reaction, the reaction mixture was poured into a saturated aqueous solution of ammonium chloride and the obtained mixture was extracted with ether. The organic layer was distilled to remove the solvent and the residue was subjected to silica gel column chromatography and eluted with a solvent (ether/ hexane=1:15) to give 20 g of the title compound as a colorless oil (55%).

NMR (CDCl₃) δ(ppm): 0.77 (3H, t, J=7.2Hz, —CH₂CH₃), 1.58 (9H, s, t-Bu), 1.57–1.76 (2H, m, N—CH₂CH₃), 2.01–2.24 (2H, m, I—CH₂—CH₂=CH—Ar), 2.63–3.09 (3H, m, I—CH₂—CH₂—CH—Ar), 7.22 (2H, d, J=8.4Hz, ArH), 7.94 (2H, d, J=8.4Hz, ArH).

PREPARATIVE EXAMPLE 8

(E)-t-Butyl 4-[5-[N-cyanomethyl-N-β-cyanovinylamino]pentan-3-yl]benzoate

[a compound represented by the formula (13) wherein n is 2, R² is a phenylene group, R³ is H, R⁴ is Et and R⁷ is t-Bu]

The N-alkylation of 3-(N-cyanomethyl)aminoacrylonitrile (7.2 g) with the t-butyl 4-(3-iodo-1-ethylpropyl)benzoate (24.4 g) prepared in the Preparative Example 7 was conducted by the same procedure as that of the Preparative Example 3. 17 g of the title compound was obtained (74%).

NMR (CDCl₃) δ(ppm): 0.78 (3H, t, J=7.2Hz, —CH₂CH₃), 1.52–1.77 (2H, m, —CH₂CH₃), 1.59 (9H, s, t-Bu), 1.82–2.09 (2H, m N—CH₂—CH₂—CH—Ar), 2.42–2.54 (1H, m, N—CH₂—CH₂—CH—Ar), 2.91–3.08 (2H, m, N—CH₂=CH₂—CH—Ar), 3.83 (2H, s, N—CH₂—CN), 3.93 (1H, d, J=14Hz, N—CH=CH—CN), 6.7 (1H, d, J=14Hz, N—CH=CH—CN), 7.18 (2H, d, J=8.4Hz, ArH), 7.97 (2H, d, J=8.4Hz, ArH).

PREPARATIVE EXAMPLE 9 t-Butyl 4-[3-(3-amino-2-cyanopyrrol-1-yl)-1-ethylpropyl]benzoate

[a compound represented by the formula (7) wherein n is 2, R² is a phenylene group, R³ is H, R⁴ is Et and R⁷ is t-Bu]

The (E)-t-butyl 4-[5-[N-cyanomethyl-N-β-cyanovinylamino]pentan-3-yl]benzoate (10 g) prepared in the Preparative Example 8 was converted into (Z)-t-butyl 4-[5-[N-cyanomethyl-N-β-cyanovinylamino]pentan-3-yl]benzoate through photoisomerization according to the same procedure as that of the Preparative Example 3.

NMR (CDCl₃) δ(ppm): 0.78 (3H, t, J=7.2Hz, —CH₂CH₃), 1.58 (9H, s, t-Bu), 1.51–1.68 (2H, m, —CH₂CH₃), 1.86–2.19 (2H, m, N—CH₂—CH₂—CH—Ar), 2.53–2.62 (1H, m, N—CH₂—CH₂—CH—Ar), 3.01–3.33 (2H, m, N—CH₂—CH₂—CH—Ar), 3.94 (1H, d, J=10Hz, N—CH=CH—CN), 4.19 (2H, q, 18Hz, N—CH₂—CN), 6.06 (1H, d, J=10Hz, N—CH=CH—CN), 7.21 (2H, d, J=8.4Hz, ArH), 7.94 (2H, d, J=8.4Hz, ArH).

The obtained Z isomer was converted into the title compound (4.8 g, 48%) through ring closure.

NMR (CDCl₃) δ(ppm): 0.74 (3H, t, J=7.2Hz, —CH₂CH₃), 1.59 (9H, s, t-Bu), 1.56–1.77 (2H, m, —CH₂CH₃), 1.98–2.47 (3H, m, N—CH₂—CH₂—CH—Ar), 3.56–3.74 (4H, m, NH₂, N—CH₂—CH₂—CH—Ar), 5.58 (1H, d, J=3Hz, pyrrole 4-H), 6.34 (1H, d, J=3Hz, pyrrole 5-H), 7.19 (2H, d, J=8.4Hz, ArH), 7.95 (2H, d, J=8.4Hz, ArH).

MS: FAB-MS m/z: 325 (M⁺).

EXAMPLE 5

4-[2-(2,4-Diaminopyrrolo[3,2-d]pyrimidin-5-yl)-1-ethyl propyl]benzoic acid

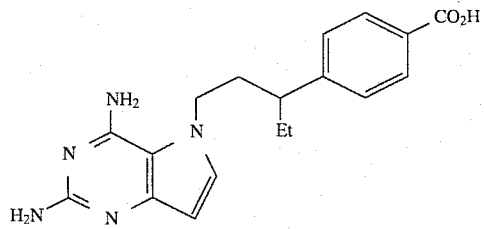

[a compound represented by the formula (2) wherein n is 2, R¹ is NH₂, R² is a phenylene group, R³ is H and R⁴ is Et]

The t-butyl 4-[3-(3-amino-2-cyanopyrrol-1-yl)-1-ethylpropyl]benzoate (3.4 g, 9.6 mmol) prepared in the Preparative Example 9 was converted into t-butyl 4-[2-(2,4-diaminopyrrolo[3,2-d]pyrimidin-5-yl)-1-ethylpropyl]benzoate through ring closure according to the same procedure as that of the Example 1. This product was hydrolyzed with acid in a similar manner to that of the Example 2 to give 1.53 g of the title compound (47%).

NMR (CD₃OD+CDCl₃) δ(ppm): 0.76 (3H, t, J=7.2Hz, —CH₂CH₃), 1.58–1.77 (2H, m, —CH₂CH₃), 2.09–2.48 (3H, m, N—CH₂—CH₂—CH—Ar), 4.14 (2H, t, J=7Hz, N—CH₂—CH₂—CH—Ar), 6.09 (1H, d, J=2Hz, 7-H), 7.04 (1H, d, J=2Hz, 6-H), 7.21–7.28 (2H, m, ArH), 7.95–7.99 (2H, m, ArH).

EXAMPLE 6

N-[4-[3-(2,4-Diaminopyrrolo[3,2-d]pyrimidin-5-yl)-1-ethylpropyl]benzoyl]-L-glutamate

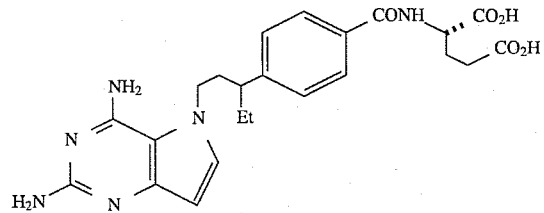

[a compound represented by the formula (1) wherein n is 2, R¹ is NH₂, R² is a phenylene group, R³ is H and R⁴ is Et]

The 4-[2-(2,4-diaminopyrrolo[3,2-d]pyrimidin-5-yl)ethylpropyl]benzoic acid (1.53 g, 4.5 mmol) prepared in the Example 5 was condensed with diethyl L-glutamate hydrochloride in a similar manner to that of the Example 2 to give an amide compound. The ethyl ester moieties of the amide compound were hydrolyzed to give 1.02 g of the title compound (48%).

NMR (CD₃OD+CDCl₃) δ(ppm): 0.71 (3H, t, J=7.2Hz, —CH₂CH₃), 1.48–1.72 (2H, m, —CH₂CH₃), 2.08–2.52 (7H, m, N—CH₂—CH₂—CH—Ar, —CH₂—CH²—CO₂H), 4.11–4.28 (2H, m, N—CH₂—CH₂—CH—Ar), 4.51–4.56 (1H, m, —CONH—CH—), 6.01–6.03 (1H, m, 7-H), 7.11–7.16 (3H, m, 6-H, 12-CH, 16-CH), 7.68–7.73 (2H, m, 13-CH, 15-CH)

mol. form. $C_{23}H_{27}N_6O_5Na \cdot H_2O$

| elem. anal. | |
|---|---|
| calculated (%) | found (%) |
| C 54.33 | C 54.88 |
| H 5.75 | H 5.75 |
| N 16.52 | N 16.00 |

MS: FAB-MS m/z: 469 (M+H)$^+$.

PREPARATIVE EXAMPLE 10 t-Butyl 4-[1-methylene-3-iodopropyl]benzoate

[a compound represented by the formula (32) wherein $R^2$ is a phenylene group, $R^7$ is t-Bu and Y is I]

t-Butyl p-formylbenzoate (20 g, 97 mmol) was dissolved in ether (300 ml), followed by the dropwise addition of vinylmagnesium bromide (1M THF solution, 100 ml) under cooling with ice. The obtained mixture was stirred to complete a reaction. The reaction mixture was poured into water and the obtained mixture was extracted with ether. The organic layer was distilled to remove the solvent. The residue was subjected to silica gel column chromatography and eluted with a solvent (ethyl acetate/hexane=1:4) to give 22.4 g of an allyl alcohol (corresponding to a compound represented by the formula (23) wherein $R^2$ is phenylene and $R^7$ is t-Bu). This alcohol was dissolved in DMF (150 ml) to give a solution. Imidazole (16.3 g) and t-butyldimethylsilyl chloride (18 g) were dissolved in the solution completely. The obtained solution was allowed to stand at room temperature to complete a reaction. The reaction mixture was poured into water and the obtained mixture was extracted with ether. The organic layer was distilled to remove the solvent. The residue was subjected to silica gel column chromatography and eluted with a solvent (ether/hexane= 1:5) to give 32 g of an O-silylate (corresponding to a compound represented by the formula (24) wherein $R^2$ is phenylene and $R^7$ is t-Bu). This silylate was dissolved in THF (150 ml), followed by the dropwise addition of a 1M solution (185 ml) of $BH_3$ in THF under cooling with ice. Methanol (100 ml) was dropped into the mixture prepared above, while stirring the mixture under cooling with ice. Further, 1N aqueous sodium hydroxide (100 ml) and 30% hydrogen peroxide (150 ml) were added to the obtained mixture. The mixture thus prepared was stirred at room temperature to conduct a reaction. The reaction mixture was poured into a saturated aqueous solution of ammonium chloride. The obtained mixture was extracted with ethyl acetate. The organic layer was distilled to remove the solvent. The residue was subjected to silica gel column chromatography and eluted with a solvent (ethyl acetate/hexane=1:4) to give 25 g of t-butyl 4-[1-(butyldimethylsilyloxy)- 3-hydroxypropylbenzoate. This product was dissolved in 3,4-dihydro-2H-pyran (150 ml), followed by the addition of a catalytic amount of pyridinium p-toluenesulfonate. The obtained mixture was allowed to stand at room temperature to complete a reaction. The reaction mixture was poured into water and the obtained mixture was extracted with ether. The organic layer was distilled to remove the solvent and the residue was subjected to silica gel column chromatography and eluted with a solvent (ethyl/hexane=1:10) to give 30 g of a protected diol compound (corresponding to a compound represented by the formula (27) wherein $R^2$ is phenylene and $R^7$ is t-Bu). This diol compound was dissolved in THF (150 ml), followed by the addition of tetrabutylammonium fluoride (1M THF solution, 100 ml). The obtained mixture was stirred at room temperature to complete a reaction. The reaction mixture was poured into a saturated aqueous solution of ammonium chloride and the obtained mixture was extracted with ether. The organic layer was distilled to remove the solvent and the residue was subjected to silica gel column chromatography and eluted with a solvent (ethyl acetate/hexane=1:5) to give 21 g of t-butyl 4-[(1-hydroxy-3-tetrahydropyran-2-yloxy)propyl]benzoate.

Then, this product was subjected to the Swern oxidation. That is, DMSO (36 ml) was dropped into a solution of oxalyl dichloride (22 ml) in methylene dichloride (400 ml) at −78° C., followed by the dropwise addition of a solution of t-butyl 4-[(1-hydroxy-3 -tetrahydropyran-2-yloxy)propyl]benzoate (21 g) in methylene dichloride (40 ml) at −78° C. The obtained mixture was stirred for 30 minutes, followed by the dropwise addition of triethylamine (104 ml) at −78° C. The obtained mixture was stirred under cooling with ice to complete a reaction. The reaction mixture was poured into water and the obtained mixture was extracted with methylene dichloride. The organic layer was distilled to remove the solvent and the residue was subjected to silica gel column chromatography and eluted with a solvent (ethyl acetate/ hexane=1:5) to give 20 g of t-butyl 4-[(1-oxo-3-tetrahydropyran-2-yloxy)propyl]benzoate. This product was further subjected to the Wittig reaction. That is, n-butyllithium (2.5M hexane solution, 96 ml) was dropped into a suspension of methyltriphenylphosphonium bromide (86 g) in THF (500 ml) at −78° C. The obtained mixture was stirred under cooling with ice, followed by the dropwise addition of a solution of t-butyl 4-[(1-oxo-3-tetrahydropyran-2 -yloxy)propyl]benzoate (20 g) in TFH (40 ml). The obtained mixture was stirred at room temperature. The reaction mixture was poured into a saturated aqueous solution of ammonium chloride and the obtained mixture was extracted with ether. The organic layer was distilled to remove the solvent and the residue was subjected to silica gel column chromatography and eluted with a solvent (ethyl acetate/ hexane=1:5) to give an exo methylene compound (corresponding to a compound represented by the formula (30) wherein $R^2$ is phenylene and $R^7$ is t-Bu). This compound was treated with p-toluenesulfonic acid (in a catalytic amount) in methanol (200 ml) to remove the THP group. 8.5 g of a primary alcohol (corresponding to a compound represented by the formula (31) wherein $R^2$ is phenylene and $R^7$ is t-Bu) was obtained. This alcohol was dissolved in ether (200 ml), followed by the addition of triethylamine (24 ml) and methanesulfonyl chloride (5.3 ml) under cooling with ice. The obtained mixture was stirred to complete a reaction. The reaction mixture was poured into water and the obtained mixture was extracted with ether. The organic layer was distilled to remove the solvent. The residue was used as such in the subsequent reaction. That is, the obtained mesylate was dissolved in acetone (350 ml) followed by the addition of sodium iodide (16.9 g). The obtained mixture was heated under reflux to complete a reaction. The reaction mixture was poured into water and the obtained mixture was extracted with ether. The organic layer was distilled to remove the solvent. The residue was subjected to silica gel column chromatography and eluted with a solvent (ether/hexane=1:10) to give 11 g of the title compound as a colorless oil (31%).

NMR (CDCl$_3$) δ(ppm): 1.58 (9H, s, t-Bu), 3.08 (2H, t, J=7.2Hz, I—CH$_2$CH$_2$—), 3.19 (2H, t, J=7.2Hz, I—CH$_2$—CH$_2$—), 5.22 (1H, brs, olefinic proton), 5.47 (1H, brs, olefinic proton), 7.41 (2H, d, J=8.4Hz, ArH), 7.96 (2H, d, J=8.4Hz, ArH).

PREPARATIVE EXAMPLE 11 t-Butyl 4-[4-[N-cyanomethyl-N-β-cyanovinylamino]-2-buten-3-yl]benzoate

[a compound represented by the formula (13) wherein n is 1, $R^2$ is a phenylene group, $R^3$ and $R^4$ form a ethylidene group, and $R^7$ is t-Bu]

N-Cyanomethylaminoacrylonitrile (5 g, 47 mmol) was dissolved in a mixture comprising THF (150 ml) and DMF (30 ml), followed by the addition of 60% sodium hydride (1.9 g, 47 mmol) under cooling with ice. A solution of the t-butyl 4-[1-methylene-3-iodopropyl]benzoate (9 g, 25 mmol) prepared in the Preparative Example 10 in THF (20 ml) was dropped into the above-prepared mixture under cooling with ice. The obtained mixture was stirred at room temperature for one hour. The obtained reaction mixture was poured into a saturated aqueous solution of ammonium chloride and the obtained mixture was extracted with ethyl acetate. The organic layer was distilled to remove the solvent and the residue was subjected to silica gel column chromatography and eluted with a solvent (ethyl acetate/hexane= 1:3) to give 4 g of the title compound (47%), which was composed of two isomers, i.e., Z and E isomers. The spectral data of both isomers are given below.

NMR (CDCl₃) δ(ppm): 1.6 (9H, s, t-Bu), 1.67 (3H, d, J=8Hz, ethylidene-Me), 3.83 (2H, s, —N—CH₂—), 4.01 (1H, d, J=15Hz, —N—CH=CH—CN), 4.06 (2H, s, —N—CH₂—), 5.9 (1H, q, J=8Hz, ethylidene-H), 6.75 (1H, d, J=15Hz, —N—CH=CH—CN), 7.18 (2H, d, J=8.4Hz, ArH), 8.01 (2H, d, J=8.4Hz, ArH). 1.59 (9H, s, t-Bu), 1.99 (3H, d, J=9Hz, ethylidene-Me), 3.75 (2H, s, —N—CH₂—), 4.12 (1H, d, J=15Hz, N—CH=CH—CN), 4.28 (2H, s, N—CH₂—), 6.29 (1H, q, J=9Hz, ethylidene-H), 6.86 (1H, d, J=15Hz, —N—CH=CH—CN), 7.28 (2H, d, J=8.4Hz, ArH), 7.96 (2H, d, J=8.4Hz, ArH).

MS: FAB-MS m/z: 338(M+H)⁺.

PREPARATIVE EXAMPLE 12 t-Butyl 4-[2-(3-amino-2-cyanopyrrol-1-yl)-1-ethylideneethyl]benzoate

[a compound represented by the formula (7) wherein n is 1, $R^2$ is a phenylene group, $R^3$ and $R^4$ form a ethylidene group and $R^7$ is t-Bu]

The t-butyl 4-[4-[N-cyanomethyl-N-β-cyanovinylamino]-2-buten-3-yl]benzoate (4 g) prepared in the Preparative Example 11 was dissolved in ether (500 ml) and the obtained solution was irradiated with light (from a high-pressure mercury lamp) in the presence of acetophenone (2 ml) at room temperature. The reaction mixture was distilled to remove the solvent. The residue was subjected to silica gel column chromatography and eluted with a solvent (ether/hexane=2:1) to isolate a Z isomer. This isomer was treated with LDA in a similar manner to that of the Preparative Example 3 to give 1.2 g of the title compound through ring closure (30%).

NMR (CDCl₃) δ(ppm): 1.58 (9H, s, t-Bu), 1.58 (3H×⅔, d, J=9Hz, ethylidene-Me), 1.99 (3H×⅓, d, J=9Hz, ethylidene-Me), 4.63 (2H×⅔, s, >N—CH₂—), 4.91 (2H×⅓, s, >N—CH₂—), 5.49 (1H×⅓, d, J=3Hz, pyrrole 4-H), 5.53 (1H×⅔, d, J=3Hz, pyrrole 4-H), 5.78 (1H×⅓, q, J=9Hz, ethylidene-H), 6.19 (1H×⅔, q, J=9Hz, ethylidene-H), 6.35 (1H×⅔, d, J=3Hz, pyrrole 5-H), 6.38 (1H×⅓, d, J=3Hz, pyrrole 5-H), 7.08 (2H×⅔, d, J=8.4Hz, ArH), 7.87 (2H×⅓, d, J=8.4 Hz, ArH), 7.92 (2H×⅔, d, J=8.4Hz, ArH).

EXAMPLE 7 t-Butyl 4-[2-(2,4-diaminopyrrolo[3,2-d]pyrimidin-5-yl)-1-ethylideneethyl]benzoate

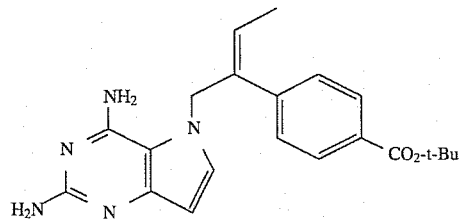

[a compound represented by the formula (6) wherein n is 1, $R^1$ is $NH_2$, $R^2$ is a phenylene group, $R^8$ and $R^4$ form a ethylidene group and $R^7$ is t-Bu]

The t-butyl 4-[2-(3-amino-2-cyanopyrrol-1-yl)-1-ethylideneethyl]benzoate (1.2 g, 3.6 mmol) prepared in the Preparative Example 12 was treated according to the same procedure as that of the Example 1 to give 0.71 g of the title compound through ring closure (52%).

EXAMPLE 8

4-[2-(2,4-Diaminopyrrolo[3,2-d]pyrimidin-5-yl)-1-ethyl-ethyl]benzoic acid

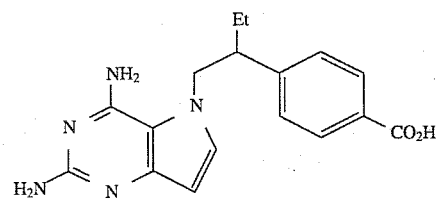

[a compound represented by the formula (2) wherein n is 1, $R^1$ is $NH_2$, $R^2$ is a phenylene group, $R^3$ is H and $R^4$ is Et]

The t-butyl 4-[2-(2,4-diaminopyrrolo[3,2-d] pyrimidin-5-yl)-1-ethylideneethyl]benzoate prepared in the Example 7 was catalytically reduced with 10% palladium-carbon (0.2 g) in a mixture comprising acetic acid (15 ml) and methanol (150 ml). The reduction product was added to a mixture comprising 1N aqueous hydrochloric acid (50 ml) and 1,4-dioxane (50 ml). The obtained mixture was stirred at 90° C. for one hour to complete a reaction. The reaction mixture was concentrated, subjected to silica gel column chromatography and eluted with a solvent (acetic acid/methanol/ethyl acetate=1:1:5) to give 0.5 g of the title compound (83%).

NMR (CD₃OD+CDCl₃) δ(ppm): 0.78 (8H, t, J=7.2Hz, —CH₂CH₃), 1.64–2.18 (2H, m, —CH₂—CH₈), 2.96–8.02 (1H, m, —N—CH₂CH—Ar), 4.81–4.72 (2H, m, —N—CH₂=CH—Ar), 5.98 (1H, d, J=8Hz, 7-H), 6.96 (1H, d, J=8Hz, 6-H), 7.02–7.18 (2H, m, ArH), 7.82–7.94 (2H, m, ArH).

EXAMPLE 9

N-[4-[2-(2,4-Diaminopyrrolo[3,2-d]pyrimidin-5-yl)-1-ethylethyl]benzoyl]-L-glutamate

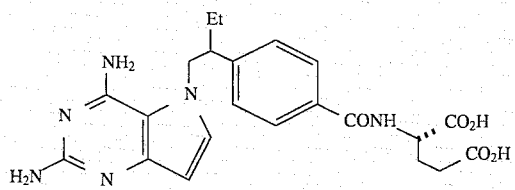

[a compound represented by the formula (1) wherein n is 1, $R^1$ is $NH^2$, $R^2$ is a phenylene group, $R^3$ is H and $R^4$ is Et]

The 4-[2-(2,4-diaminopyrrolo[3,2-d]pyrimidin-5 -yl)-1-ethylethyl]benzoic acid (0.5 g, 1.6 mmol) prepared in the Example 8 was condensed with diethyl L-glutamate hydrochloride in a similar manner to that of the Example 2. The ethyl ester moieties or the condensation product were hydrolyzed to give the title compound. The compound was purified by silica gel column chromatography and the obtained solid was washed with ethanol and a small amount of methanol to give 170 mg of a pure product as a pale-yellow powder (24%).

mol. form. $C_{22}H_{26}N_6O_5 \cdot 2H_2O$

NMR ($CD_3OD+CDCl_3$) δ(ppm): 0.71 (3H, t, J=7.2Hz, $CH_2CH_3$), 1.62–2.22 (6H, m, $CH_2$—$CH_3$, —$CH_2CH_2CO_2H$), 2.91–2.98 (1H, m, N—$CH_2$—CH—Ar), 4.19–4.45 (2H, m, N—$CH_2$—CH—Ar), 4.58–4.63 (1H, m, —CONHCH—), 5.91 (1H, d, J=3Hz, 7H), 6.96 (1H, d, J=3Hz, 6H), 7.23–7.27 (2H, m, ArH), 7.76–7.81 (2H, m, ArH).

MS: FAB-MS m/z: 499 $(C_{22}H_{24}N_6O_5Na_2+H)^+$.

PREPARATIVE EXAMPLE 13 t-Butyl 5-formyl-2-thiphenecarboxylate

[a compound represented by the formula (18) wherein $R^2$ is a thiendiyl group, $R^4$ is H and $R^7$ is t-Bu]

A 1.7M solution of t-butyllithium in pentane (8.0 ml, 13.6 mmol] was dropped into a solution of t-butyl 2-thiphenecarboxylate (1.84 g, 10 mmol) and N,N,N',N'-tetramethylethylenediamine (1.74 g, 15 mmol) in anhydrous tetrahydrofuran in a nitrogen atmosphere, while stirring the solution under cooling with dry ice-acetone. The obtained mixture was stirred for about 50 minutes. Anhydrous dimethylformamide (15 ml) was gradually dropped into the resulting mixture to conduct a reaction. The temperature of the obtained liquid mixture was raised to room one and the resulting mixture was stirred for 40 minutes and poured into 300 ml of a diethyl ether/0.3N hydrochloric acid (2:1) mixture. The obtained mixture was stirred. The organic layer was recovered, washed with a phosphate burger (pH: 7) and an aqueous solution of common salt, dehydrated and distilled to remove the solvent. The residue was purified by silica gel column chromatography (using an n-hexane/ethyl acetate (8:1) mixture as a developer) to give 1.7 g of the title compound.

NMR ($CDCl_3$) δ(ppm): 1.59 (9H, s), 7.70 (1H, d, J=4.0Hz), 7.75 (1H, d, J=4.0Hz), 9.95 (1H, s)

IR (neat) v: 2981, 1713, 1682 $cm^{-1}$.

PREPARATIVE EXAMPLE 14 t-Butyl 5-(2-ethoxycarbonyl-E-ethenyl)-2-thiophenecarboxylate

[a compound represented by the formula (19) wherein $R^2$ is a thiendiyl group, $R^4$ is H and $R^7$ is t-Bu]

Sodium hydride (min. 60% paraffin dispersion, 1.88 g, about 47 mmol) was washed with anhydrous hexane in a nitrogen stream and dispersed in anhydrous tetrahydrofuran. The obtained dispersion was stirred under cooling with ice, followed by the gradual dropwise addition of a solution of ethyl diethylphosphonoacetate (10.53 g, 47 mmol) in anhydrous tetrahydrofuran. The obtained mixture was stirred at room temperature for 15 minutes. A solution of the t-butyl 5-formyl-2-thiophenecarboxylate (6.65 g, 31.3 mmol) prepared in the Preparative Example 13 in anhydrous tetrahydrofuran was gradually dropped into the resulting mixture. The obtained mixture was stirred at room temperature for 30 minutes, diluted with diethyl ether, washed with a dilute alkali, dilute hydrochloric acid and an aqueous solution of common salt, dehydrated and evaporated to dryness in a vacuum. The residue was purified by silica gel column chromatography (using an n-hexane/ethyl acetate (8:1) mixture as a developer) to give 7.58 g of the title compound.

NMR ($CDCl_3$) δ(ppm): 1.33 (3H, t, J=7.2Hz), 1.57 (9H, s), 4.25 (2H, q, J=7.2Hz), 6.33 (1H, d, J=15.6Hz), 7.18 (1H, d, J=4.0Hz), 7.61 (1H, d, J=4.0Hz), 7.70 (1H, d, J=15.6Hz)

IR (neat) v: 2980, 1713, 1706, 1630, 969 $cm^{-1}$.

PREPARATIVE EXAMPLE 15 t-Butyl 5-(2-ethoxycarbonylethyl)-2-thiophenecarboxylate

The t-butyl 5-(2-ethoxycarbonyl-E-ethenyl)-2-thiophenecarboxylate (7.58 g, 26.8 mmol) prepared in the Preparative Example 14 was catalytically reduced with 10% palladium-carbon (1.05 g) in ethanol at room temperature. After the completion of the reaction, the catalyst was filtered out and the filtrate was concentrated and evaporated to dryness in a vacuum. 7.6 g of the title compound was obtained.

NMR (neat) δ(ppm): 1.26 (3H, t, J=7.2Hz), 1.56 (9H, s), 2.68 (2H, t, J=7.6Hz), 3.15 (2H, t, d, J=7Hz, 0.8Hz), 4.15 (2H, q, J=7.2Hz), 6.79 (1H, dt, J=3.6Hz, 0.8Hz), 7.54 (1H, d, J=3.6Hz).

PREPARATIVE EXAMPLE 16 t-Butyl 5-(3-hydroxypropyl)-2-thiophenecarboxylate

[a compound represented by the formula (21) wherein $R^2$ is a thiendiyl group, $R^4$ is H and $R^7$ is t-Bu]

The t-butyl 5-(2-ethoxycarbonylethyl)-2-thiophenecarboxylate (7.6 g, 26.8 mmol) prepared in the Preparative Example 15 was partially hydrolyzed in an ethanol/1N sodium hydroxide mixture at room temperature to give 6.1 g of 3-(5-t-butoxycarbonylthiophen- 2-yl)propionic acid. This acid was dissolved in anhydrous tetrahydrofuran and the obtained solution was dropped into a solution of borane in tetrahydrofuran, which had been preliminarily prepared from sodium borohydride (3.37 g, 89 ml) and trifluoroborane-diethyl ether complex (16.9 g, 119 mmol), under cooling with ice in about 30 minutes. The obtained mixture was stirred for 30 minutes, followed by the gradual dropwise addition of methanol. After the generation of hydrogen gas had discontinued, the reaction mixture was filtered and the filtrate was evaporated to dryness. Methanol was added to the residue to remove the boron compound by azeotropic distillation. The residue was dissolved in diethyl ether and the obtained solution was washed with a dilute hydrochloric acid and an aqueous solution of common salt, dehydrated and distilled to remove the solvent. The residue was evaporated to dryness in a vacuum to give 6.0 g of the compound.

NMR (CDCl₃) δ(ppm): 1.56 (9H, s), 1.94 (2H, tt, J=7.6Hz, 6.4Hz), 2.93 (2H, td, J=7.6Hz, 0.8Hz), 3.70 (2H, t, J=6.4Hz), 6.78 (1H, dr, J=3.6Hz, 0.8Hz), 7.54 (1H, d, J=3.6Hz)

IR (neat) v: 3200–3700, 2978, 2935, 1703 cm⁻¹.

PREPARATIVE EXAMPLE 17 t-Butyl 5-(3-bromopropyl)-2-thiophenecarboxylate

[a compound represented by the formula (12a) wherein $R^2$ is a thiendiyl group, $R^4$ is H, $R^7$ is t-Bu and Y is Br]

The t-butyl 5-(3-hydroxypropyl)-2-thiophenecarboxylate (6.0 g, 23.9 mmol) prepared in the Preparative Example 16 was treated in a similar manner to that of the Preparative Example 2. 6.2 g of the title compound was obtained.

NMR (CDCl₃) δ(ppm): 1.56 (9H, s), 2.21 (2H, tt, J=7.2Hz, 6.4Hz), 3.00 (2H, td, J=7.2Hz, 0.8Hz), 3.42 (2H, t, J=6.4Hz), 6.81 (1H, dr, J=3.6Hz, 0.8Hz), 7.55 (1H, d, J=3.6Hz).

PREPARATIVE EXAMPLE 18 t-Butyl 5-[3-(3-amino-2-cyanopyrrol-1-yl)propyl]-2-thiophenecarboxylate

[compound (7): n=2, $R^2$=a thiendiyl group, $R^3$=$R^4$=H, $R^7$=t-Bu]

The same procedure as that of the Preparative Example 3 was repeated except that 3-(N-cyanomethyl)aminoacrylonitrile (2.8 g) and the t-butyl 5-(3-bromopropyl)-2-thiophenecarboxylate [compound (12): n=2, $R^2$=a thiendiyl group, $R^3$=$R^4$=H, $R^7$=t-Bu group] were used as the starting materials to give 6 g (70%) of the objective t-butyl (E)-5-[3-(N-cyanomethyl-N-β-cyanovinylamino)-propyl]-2-thiophenecarboxylate.

NMR (CDCl₃) δ(ppm): 1.57(9H, s, t-Bu), 1.98–2.07(2H, m, N—CH₂—CH₂—CH₂—Ar), 2.88(2H, t, J=7.2Hz, N—CH₂—CH₂—CH₂—Ar), 3.27(2H, t, J=7.2Hz, N—CH₂—CH₂—CH₂—Ar), 3.96(2H, s, N—CH₂—CN), 4.06(1H, d, J=18Hz, N—CH=CH—CN), 6.79(1H, d, J=3.6Hz, ArH), 6.83(1H, d, J=18Hz, N—CH=CH—CN), 7.56(1H, d, J=3.6Hz, ArH).

The E isomer prepared above was irradiated with light in a similar manner to that of the Preparative Example 3 to give 2.8 g (47%) of t-butyl Z-5-[3-(N-cyanomethyl-N-β-cyanovinylamino)propyl]-2-thiophenecarboxylate [compound (14)].

NMR (CDCl₃) δ(ppm): 1.56(9H, s, t-Bu), 2.04–2.13(2H, m, N—CH₂—CH₂—CH₂—Ar), 2.92(2H, t, J=7.2Hz, N—CH₂—CH₂—CH₂—Ar), 3.44(2H, t, J=7.2Hz, N—CH₂—CH₂—CH₂—Ar), 4.01(1H, d, J=10Hz, N—CH=CH—CN), 4.28(2H, s, N—CH₂—CN), 6.22(1H, d, J=10Hz, N—CH=CH—CN), 6.79(1H, d, J=3.6Hz, ArH), 7.54(1H, d, J=3.6Hz, ArH).

The Z isomer (41) (2.8 g) was subjected to the same ring closure with LDA as that of the Preparative Example 3 to give 2.4 g (86%) of the objective title compound, i.e., t-butyl 5-[3-(3-amino-2-cyanopyrrol-1-yl)propyl]-2-thiophenecarboxylate [compound (7): n= $R^2$=a thiendiyl group, $R^3$=$R^4$=H, $R^7$=t-Bu].

NMR (CDCl₃) δ(ppm): 1.56 (9H, s, t-Bu), 2.16(2H, m, N—CH₂—CH₂—CH₂—Ar), 2.79(2H, t, J=7.2Hz, N—CH₂—CH₂—CH₂—Ar), 3.9(2H, t, J=7.2Hz, N—CH₂—CH₂—CH₂—Ar), 5.64(1H, d, J=2.8Hz, pyrrole 4-H), 6.52(1H, d, J=2.8Hz, pyrrole 5-H), 6.77 (2H, d, J=3.6Hz, ArH), 7.55(1H, d, J=8.6Hz, ArH).

EXAMPLE 10 t-Butyl 5-[3-(2,4-diaminopyrrolo[3,2-d]pyrimidin-5-yl)propyl]-2-thiophenecarboxylate

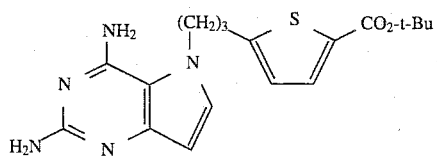

[compound (6): n=2, $R^1$=NH₂, $R^2$=a thiendiyl group, $R^3$=$R^4$=H, $R^7$=t-Bu]

t-Butyl 5-[3-(3-amino-2-cyanopyrrol-1-yl)propyl]-2-thiophenecarboxylate (7) (2.4 g) prepared in the Preparative Example 18 was subjected to the same ring closure as that of the Example 1 to give 2.1 g (78%) of the objective title compound through the formation of a pyrrolopyrimidine ring.

NMR (CD₃OD) δ(ppm): 1.54(9H, s, t-Bu), 2.13–2.21 (2H, m, N—CH₂—CH₂—CH₂—Ar), 2.81 (2H, t, J=7.2Hz, N—CH₂—CH₂—CH₂—Ar), 4.37(2H, t, J=7.2Hz, N—CH₂—CH₂—CH₂—Ar), 6.18(1H, d, J=3Hz, 7-H), 6.81 (1H, d, J=3.8Hz, ArH), 7.34(1H, d, J=3Hz, 6-H), 7.5(1H, d, J=3.8Hz, ArH).

EXAMPLE 11

N-[5-[3-(2,4-Diaminopyrrolo[3,2-d]pyrimidin-5-yl)propyl]thenoyl]-L-glutamate

[compound (7): n=2, $R^2$=a thiendiyl group, $R^3$=$R^4$=H]

In a similar manner to that of the Example 2, t-butyl 5-[3-(2,4-diaminopyrrolo[3,2-d]pyrimidin-5-yl)propyl]-2-thiophenecarboxylate [compound (6)] prepared in the Example 10 was hydrolyzed, condensed with diethyl glutamate by the use of DPPA, and hydrolyzed with an alkali to give 0.95 g (38%) of the title compound as a pale-yellow crystalline substance.

mol. form.: $C_{19}H_{22}N_6O_5S$

MS: FAB-MS m/z: 447 (M+H⁺)

NMR (DMSO) δ(ppm): 1.84–2.03(4H, m, N—CH₂—CH₂—CH₂—Ar, NHCH—CH₂—CH₂—CO₂H), 2.24–2.28(2H, m, NHCH—CH₂—CH₂-CO₂H), 2.68(2H, t, J=7.2Hz, N—CH₂—CH₂—CH₂—Ar), 4.21–4.33(3H, m, —CONHCH₂—, N—CH₂—CH₂—CH₂—Ar), 5.98(1H, d, J=3.2Hz, 7-H), 6.67–6.83(2H, brd, NH,), 6.81 (1H, d, J=3.8Hz, ArH), 7.07–7.15(2H, brd, NH,), 7.32((1H, dd, J=3, 2Hz, 1, 2Hz, 6-H), 7.61 (1H, d, J=3.8Hz, ArH), 8.27(1H, d, J=8Hz, —CONH—).

PREPARATIVE EXAMPLE 19

1-t-Butoxycarbonyl-3-amino-2-cyano-Δ²-pyrroline

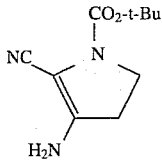

N—Cyanomethyl-β-alanine ethyl ester (36 g, 0.23 mol) was dissolved in CH$_2$Cl$_2$ (200 ml), followed by the addition of triethylamine (48 ml) and di-t-butyl dicarbonate (55 g). The obtained mixture was stirred at room temperature to complete a reaction. The reaction mixture was poured into water and the obtained mixture was extracted with ethyl acetate. The organic layer was distilled to remove the solvent. The residue was subjected to silica gel column chromatography and eluted with a solvent (ethyl acetate/hexane=1:3) to give 22.7 g of N-t-butoxy-carbonyl-N-cyanomethyl-β -alanine ethyl ester. Then, this ester was subjected to ring closure. A solution of N-t-butoxycarbonyl-N-cyanomethyl-β-alanine ethyl ester (22.7 g) in toluene (100 ml) was dropped into a t-BuOK (9.9 g)/toluene (400 ml) mixture under cooling with ice. The obtained mixture was stirred under cooling with ice to complete a reaction. The reaction mixture was poured into a phosphate buffer having a pH of 7.1. The obtained mixture was made weakly acidic and extracted with chloroform. The organic layer was distilled to remove the solvent. The residue was used in the subsequent step. The residue was dissolved in ethanol (300 ml), followed by the addition of HCO$_2$NH$_4$ (11.3 g). The obtained mixture was heated under reflux to complete a reaction. The reaction mixture was concentrated, followed by the addition of a saturated aqueous solution of ammonium chloride. The obtained mixture was extracted with ethyl acetate and the organic layer was distilled to remove the solvent. The residue was subjected to silica gel column chromatography and eluted with a solvent (ethyl acetate/hexane=1:2) to give 4.5 g (9.6%) of the objective title compound.

*ref.: Henry Rapoport et al., J. Am. Chem. Soc., 86, 5293 (1964)

NMR (CDCl$_3$) δ(ppm): 1.51 (9H, s, t-Bu), 2.73 (2H, t, J=7.4Hz, pyrroline 4-H), 3.77 (2H, t, J=7.4Hz, pyrroline 5-H), 4.28 (2H, brs, NH$_2$).

PREPARATIVE EXAMPLE 20

5-t-Butoxycarbonyl-2,4-diamino-6,7-dihydropyrrolo[3,2-d]pyrimidine

[5-t-Butoxycarbonyl-2,4-diamino-Δ$^2$-pyrrolino[3,2-d]pyrimidine]

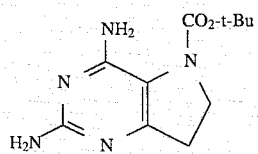

Then, ring closure was subjected. 1-t-Butoxycarbonyl-3-amino-2-cyano-Δ$^2$-pyrroline (2 g) prepared in the Preparative Example 19 was dissolved in t-butanol (30 ml), followed by the addition of guanidine carbonate (5.2 g). The obtained mixture was put in a stainless steel cylinder and heated at 145° C. for 24 hours in a hermetically sealed state. The resulting mixture was concentrated, subjected to silica gel column chromatography and eluted with a solvent (ethyl acetate/methanol/acetic acid=20:1:1) to give 1.2 g (50%) of the objective title compound as a crystalline substance.

NMR (CD$_3$OD) δ(ppm): 1.53(9H, s, t-Bu), 2.91 (2H, t, J=8.4Hz, 7-H). 3.94(2H, t, J=8.4Hz, 6-H).

EXAMPLE 12 t-Butyl N-[4-[3-(2,4-diamino-6,7-dihydropyrrolo[3,2 -d]pyrimidin-5-yl)propyl]benzoate

[t-Butyl N-[4-[3-(2,4-diamino-Δ$^2$-pyrrolino[3,2 -d]pyrimidin-5-yl)propyl]benzoate]

5-t-Butoxycarbonyl-2,4-diamino-6,7-dihydropyrrolo[3,2-d]pyrimidine (0.7 g) prepared in the Preparative Example 20 was treated with 1N HCl/AcOH (20 ml) and the obtained mixture was distilled to remove the solvent. The residue was fully dried and dissolved in DMF (15 ml), followed by the addition of sodium acetate (0.69 g) and t-butyl 4-(3-iodopropyl)benzoate (0.96 g) prepared in the Preparative Example 2. The obtained mixture was stirred at room temperature for 24 hours to complete a reaction. The reaction mixture was distilled to remove the solvent. The residue was subjected to silica gel column chromatography and eluted with a solvent (ethyl acetate/methanol/acetic acid=10:1:1) to give 0.83 g (79%) of the objective title compound.

NMR (DMSO) δ(ppm): 1.47(9H, s, t-Bu), 1.81–1.93(2H, m, N—CH$_2$—CH$_2$—CH$_2$—Ar), 2.62(2H, t, J=7.6Hz, N—CH$_2$—CH$_2$$_{-CH2}$—Ar), 2.67(2H, t, J=8.4Hz, 7-H), 2.77(2H, t, J=7.6Hz, N—CH$_2$—CH$_2$—CH$_2$—Ar), 3.17(2H, t, J=8.4Hz, 6-H), 7.27(2H, d, J=8Hz, ArH), 7.76(1H, d, J=8Hz, ArH).

EXAMPLE 13

N-[4-[3-(2,4-Diamino-6,7-dihydropyrrolo[3,2=d]-pyrimidin- 5-yl)propyl]-L-glutamate

[N-[4-[3-(2,4-Diamino-Δ$^2$-pyrrolino[3,2-d]pyrimidin-5-yl)propyl]-L-glutamate]

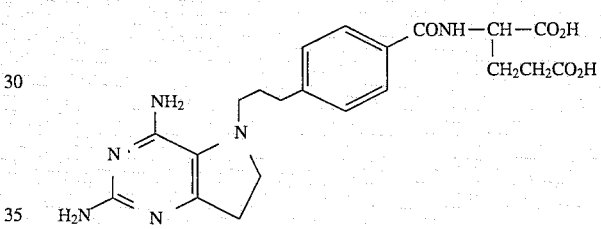

In a similar manner to that of the Example 2, t-butyl N-[4-[3-(2,4-diamino-6,7-dihydropyrrolo[3,2-d]pyrimidin-5-yl)propyl]benzoate (0.2 g) prepared in the Example 12 was hydrolyzed, condensed with diethyl L-glutamate by the use of DPPA, and hydrolyzed with an alkali to give 50 mg (22%) of the title compound as a crystalline substance.

mol. form.: C$_{21}$H$_{26}$N$_6$O$_5$

MS: FAB-MS m/z: 443 (M+H$^+$)

NMR (D$_2$O) δ(ppm): 1.74–1.88(2H, m), 2.62–2.68(2H, m). 2.78–2.93(4H, m). 3.31–3.47(2H, m), 4.24–4.29(1H, m). 7.26(2H, d. J=8Hz), 7.67(2H, d. J=8Hz).

PREPARATIVE EXAMPLE 21 t-Butyl 4-[2-bromo-1-methyleneethyl]benzoate

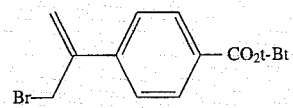

A 1.6M solution (136 ml) of n-BuLi in hexane was dropped into a suspension of methyltriphenylphosphonium bromide (78 g) in THF (400 ml) at −78° C. The obtained mixture was stirred under cooling with ice, followed by the dropwise addition of a solution of t-butyl p-formylbenzoate (30 g, 145 mmol) in THF (100 ml). The obtained mixture was stirred under cooling with ice and poured into a saturated aqueous solution of ammonium chloride. The obtained mixture was extracted with ether and the organic layer was distilled to remove the solvent. The residue was subjected to silica gel column chromatography and eluted with a solvent (ether/hexane=1:15) to give a styrene compound (23 g). This compound was dissolved in acetone (300 ml), followed by the addition of a solution (5 mg/ml, 30 ml) of OsO₄ in t-BuOH and 4-methylmorpholine N-oxide (504 aqueous solution, 75 ml) under stirring at room temperature. The obtained mixture was stirred at room temperature to complete a reaction. The reaction mixture was poured into water and the obtained mixture was extracted with ethyl acetate. The organic layer was distilled to remove the solvent and the residue was subjected to silica gel column chromatography and eluted with a solvent (ethyl acetate/hexane=1:2) to give 25 g of a diol compound. This diol compound was dissolved in methylene dichloride (500 ml), followed by the addition of trityl chloride (88 g), 4-dimethylaminopyridine (12.8 g) and triethylamine (44 ml). The obtained mixture was stirred at room temperature to complete a reaction. The reaction mixture was poured into a saturated aqueous solution of ammonium chloride and the obtained mixture was extracted with ether. The organic layer was distilled to remove the solvent. The residue was subjected to silica gel column chromatography and eluted with a solvent (ethyl acetate/hexane=1:10) to give 35 g of an objective compound wherein only the primary alcohol group was protected. This compound was subjected to the Swern oxidation. DMSO (40 ml) was dropped into a solution of oxalyl chloride (20 ml) in methylene dichloride (500 ml) at −78° C., followed by the dropwise addition of a solution of t-butyl 4-[(1-hydroxy-2-trityloxy)ethyl]benzoate (35 g) in methylene dichloride (50 ml) at −78° C. The obtained reaction mixture was stirred for 30 minutes, followed by the dropwise addition of triethylamine (94 ml) at −78° C. The obtained mixture was stirred under cooling with ice to complete a reaction. The reaction mixture was poured into water and the obtained mixture was extracted with methylene dichloride. The organic layer was distilled to remove the solvent and the residue was subjected to silica gel column chromatography and eluted with a solvent (ethyl acetate/hexane=1:12) to give an oxo compound (34 g). This compound was subjected to the Wittig reaction. A 2.5M solution (57 ml) of n-BuLi in hexane was dropped into a suspension of methyltriphenylphosphonium bromide (51 g) in THF (300 ml) at −78° C. The obtained mixture was stirred under cooling with ice, followed by the dropwise addition of a solution of t-butyl 4-[(1-oxo-2-trityloxy)ethyl]benzoate (34 g) in THF (100 ml). The obtained mixture was stirred at room temperature and the resulting reaction mixture was poured into a saturated aqueous solution of ammonium chloride. The obtained mixture was extracted with ether and the organic layer was distilled to remove the solvent. The residue was subjected to silica gel column chromatography and eluted with a solvent (ethyl acetate/hexane=1:15) to give an exo-methylene compound. This compound was treated with p-toluenesulfonic acid (in a catalytic amount) in a methanol (120 ml)/ethyl acetate (80 ml) mixture to remove the trityl group to thereby give 4-[(2-hydroxy- 1-methylene)ethyl]benzoate (7.5 g). This product was dissolved in ether (200 ml), followed by the addition of triethylamine (23 ml) and methanesulfonyl chloride (5.6 ml) under cooling with ice. The obtained mixture was stirred to complete a reaction. The reaction mixture was poured into water and the obtained mixture was extracted with ether. The organic layer was distilled to remove the solvent and the residue was used as such in the subsequent reaction. The obtained mesyl compound was dissolved in acetone (300 ml), followed by the addition of LiBr (14 g). The obtained mixture was heated under reflux to complete a reaction. The reaction mixture was poured into water and the obtained mixture was extracted with ether. The organic layer was distilled to remove the solvent. The residue was subjected to silica gel column chromatography and eluted with a solvent (ether/hexane=1:10) to give 8.8 g (20%) of the objective title compound as a pale-yellow oil.

¹H-NMR (CDCl₃) δ(ppm): 1.59 (9H, s, t-Bu), 4.19 (2H, s,

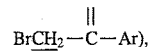

5.57 (1H, brs, olefinic proton), 5.63 (1H, brs, olefinic proton).

PREPARATIVE EXAMPLE 22 t-Butyl 4-[2-(3-amino-2-cyanopyrrol-1-yl)-1-methyleneethyl] benzoate

[compound (7): n=1, R²=a phenylene group, R³-R⁴=a methylene group, R⁷=t-Bu]

The same procedure as that of the Preparative Example 3 was repeated except that N-cyanomethylaminoacrylonitrile (3.2 g, 30 mmol) and t-butyl 4-[2-bromo- 1-methyleneethyl] benzoate (8.8 g, 30 mmol) prepared in the Preparative Example 21 were used as the starting materials to give 7.5 g (774) of the objective compound, i.e., (E)-t-Butyl 4-[3-[N-cyanomethyl-N-β-cyanovinylamino]-1-propen-2-yl] benzoate [compound (13): n=1, R²=a phenylene group, R³-R⁴=a methylene group, R⁷=t-Bu].

¹H-NMR (CDCl₃) δ(ppm): 1.59 (9H, s, t-Bu), 3.99 (2H, s, N—CH₂—CN), 4.15 (1H, d, J=15Hz, —N—CH=CH—CN), 4.24 (2H, brs,

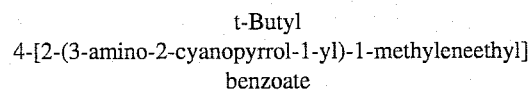

5.41 (1H, brs, olefinic proton), 5.71 (1H, brs, olefinic proton), 6.92 (1H, d, J=15Hz, —N—CH=CH—CN), 7.38 (2H, d, J=8Hz, ArH), 7.99 (2H, d, J=8Hz, ArH).

The E isomer prepared above was irradiated with light in a similar manner to that of the Preparative Example 3 to give 3 g (40%) of Z-t-butyl 4-[3-[N-cyanomethyl-N-β-cyanovinylamino]-1-propen-2-yl]benzoate [compound 14)].

¹H-NMR (CDCl₃) δ(ppm): 1.59 (9H, s, t-Bu), 4.06 (1H, d, J=10Hz, —N—CH=CH—CN), 4.27 (2H, s, N—CH₂—CN), 4.46 (2H, brs,

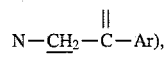

5.43 (1H, brs, olefinic proton), 5.7 (1H, brs, olefinic proton), 6.29 (1H, d, J=10Hz, —N—CH=CH—CN), 7.41 (2H, d, J=8Hz, ArH), 7.8 (2H, d, J=8Hz, ArH).

The Z isomer [compound (14)] (3 g) prepared above was subjected to the ring-closing reaction using LDA in a similar manner to that of the Preparative Example 3 to give 0.8 g (27%) of the objective title compound.

$^1$H-NMR (CDCl$_3$) δ(ppm): 1.59 (9H, s, t-Bu), 3.63 (2H, brs, NH$_2$), 4.83 (2H, brs,

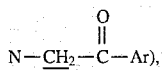

N—CH$_2$—C—Ar), 5.11 (1H, brs, olefinic proton), 5.57 (1H, brs, olefinic proton), 5.61 (1H, d, J=2.8Hz, pyrrole 4-H), 6.52 (1H, d, J=2.8Hz, pyrrole 5-H), 7.38 (2H, d, J=8.4Hz, ArH), 7.96 (2H, d, J=8.4Hz, ArH).

EXAMPLE 14 t-Butyl 4-[2-(2,4-diaminopyrrolo[3,2-d]pyrimidin-5-yl)-1-methyleneethyl]benzoate

[compound (6): n=1, R$^2$=a phenylene group, R$^3$-R$^4$=a methylene group, R$^7$ =t-Bu]

The compound (7) (0.8 g) prepared in the Preparative Example 22 was subjected to ring closure in a similar manner to that of the Example 1 to give 0.8 g (59%) of the objective title compound through the formation of a pyrrolopyrimidine ring.

$^1$H-NMR (CD$_3$OD) δ(ppm): 1.57 (9H, s, t-Bu), 5.42 (2H, brs,

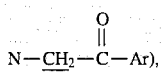

N—CH$_2$—C—Ar), 5.47 (1H, brs, olefinic proton), 5.62 (1H, brs, olefinic proton), 6.18 (1H, d, J=2.8Hz, 7-H), 7.39 (1H, d, J=2.8Hz, 6-H), 7.53 (2H, d, J=8.4Hz, ArH), 7.91 (2H, d, J=8.4Hz, ArH).

EXAMPLE 15

N-[4-[2-(2,4-Diaminopyrrolo[3,2-d]pyrimidin-5-yl)-1-methyleneethyl]benzoyl]-L-glutamate

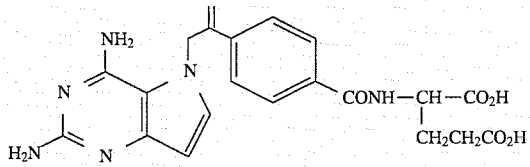

[compound (1): n=1, R$^2$=a phenylene group, R$^3$-R$^4$=a methylene group]

In a similar manner to that of the Example 2, the compound (6) (0.8 g) prepared in the Example 14 was hydrolyzed, condensed with diethyl L-glutamate by the use of DPPA, and hydrolyzed with an alkali to give 0.23 g (23%) of the title compound as a crystalline substance.

mol. form.: C$_{21}$H$_{22}$N$_6$O$_5$

MS: FAB-MS m/z: 439 (M+H$^+$)

$^1$H-NMR (DMSO-D$_2$O) δ(ppm): 1.86–2.23 (4H, m, —CONHCHCH$_2$CH$_2$—CO$_2$H), 4.17–4.22 (1H, m, —CONHCH—), 5.33 (2H, brs,

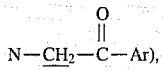

N—CH$_2$—C—Ar), 5.43–5.51 (2H, m, olefinic proton), 5.96 (1H, d, J=2.8Hz, 7-H), 7.25 (1H, d, J=2.8Hz, 6-H), 7.56 (2H, d, J=8.4Hz, ArH), 7.81 (2H, d, J=8.4Hz, ArH).

PREPARATIVE EXAMPLE 23

Ethyl 4-N-(2-bromoethyl)methylaminobenzoate

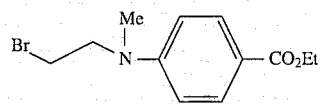

Ethyl 4-aminobenzoate (20 g) was dissolved in DMF (200 ml), followed by the addition of diisopropylethylamine (32 ml) and ethyl bromoacetate (16 ml). The obtained mixture was stirred at 70° C. to complete a reaction and the reaction mixture was poured into a saturated aqueous solution of ammonium chloride. The resulting mixture was extracted with ethyl acetate. The organic phase was distilled to remove the solvent and the obtained residue was subjected to silica gel column chromatography and eluted with a solvent (a 1:3 ethyl acetate/hexane mixture) to give 25 g of an ester. This ester was dissolved in a THF (200 ml)/DMF (40 ml) mixture. 60% Sodium hydride (4.56 g) was added to the solution thus prepared while stirring the solution under cooling with ice. Methyl iodide (8.8 ml) was added to the obtained mixture and the resulting mixture was stirred at room temperature to complete a reaction. The reaction mixture was poured into a saturated aqueous solution of ammonium chloride and the obtained mixture was extracted with ethyl acetate. The organic phase was distilled to remove the solvent. The residue was subjected to silica gel column chromatography and eluted with a solvent (a 1:3 ethyl acetate/hexane mixture) to give 15 g of an N-methyl compound. This compound was dissolved in THF (85 ml), followed by the addition of 1N sodium hydroxide (85 ml). The obtained mixture was stirred at room temperature for 2 hours to complete a reaction. The reaction mixture was neutralized with 1N hydrochloric acid and extracted with ethyl acetate to give a monocarboxylic acid. This acid was fully dried and dissolved in THF (100 ml). A 1M solution (85 ml) of BH$_3$ in THF was dropped into the obtained solution while stirring the solution under cooling with ice. The obtained mixture was stirred at room temperature for 5 hours to complete a reaction. The reaction mixture was poured into a saturated aqueous solution of ammonium chloride and the resulting mixture was extracted with ethyl acetate. The organic phase was distilled to remove the solvent and the residue was subjected to silica gel column chromatography and eluted with a solvent (a 1:1 ethyl acetate/hexane mixture) to give 11 g of a primary alcohol. This alcohol was converted into a mesyl derivative in a similar manner to that of the Preparative Example 2 and the product was further treated with LiBr to give 9 g of the title compound (28%).

NMR(CDCl$_3$) δ(ppm): 1.36(3H, t, —CO$_2$—CH$_2$—CH$_3$), 3.07(3H, s, —N—Me), 3.46(2H, t, J=7.6Hz, Br—CH$_2$—CH$_2$—N), 3.79(2H, t, J=7.6Hz, Br—CH$_2$—CH$_2$—N), 4.32(2H, q, —CO$_2$—CH$_2$—CH$_3$), 6.65(2H, d, J=9.2Hz, ArH), 7.92(2H, d, J=9.2Hz, ArH).

PREPARATIVE EXAMPLE 24

Ethyl 4-N-[2-(3-amino-2-cyanopyrrol-1-yl)ethyl]methylaminobenzoate

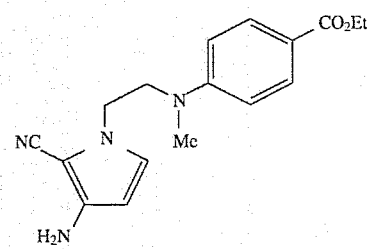

E-Ethyl 4-N-[2-[3-(N-cyanomethyl-N-β-cyanovinylamino)]ethyl]methylaminobenzoate (1 g) shown below was prepared from 3-(N-cyanomethyl)aminoacrylonitrile (0.8 g) and ethyl 4-N-(2-bromoethyl)methylaminobenzoate (2 g) prepared in the Preparative Example 23 in a similar manner to that of the Preparative Example 3 (46%).

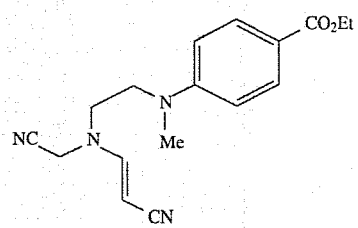

NMR (CDCl$_3$) δ(ppm): 1.37(3H, t, CO$_2$—CH$_2$—CH$_3$), 3.06(3H, s, N—Me), 3.47(2H, t, J=6Hz, N—CH$_2$—CH$_2$—N—Ar), 3.66(2H, t, J=6Hz, N—CH$_2$—CH$_2$—N—Ar), 3.94(2H, s, N—CH$_2$—CN), 4.07(1H, d, J=13.8Hz, N—CH=CH—CN), 6.64(2H, d, J=9.2Hz, ArH), 6.79(1H, d, J=13.8Hz, N—CH=CH—CN), 7.95(2H, d, J=9.2Hz, ArH).

The E isomer (3.5 g) prepared above was irradiated with light in a similar manner to that of the Preparative Example 3 to give 0.7 g of Z-Ethyl 4-N-[2-[3-(N-cyanomethyl-N-β-cyanovinylamino)]ethyl]methylaminobenzoate (20%) shown below.

NMR (CDCl$_3$) δ(ppm): 1.37(3H, t, CO$_2$—CH$_2$—CH$_3$), 3.09(3H, s, N—Me), 3.66(2H, t, J=6Hz, N—CH$_2$—CH$_2$—N—Ar), 3.76(2H, t, J=6Hz, N—CH$_2$—CH$_2$—N—Ar), 4.02(1H, d, J=10Hz. N—CH=CH—CN), 4.25(2H, s, N—CH$_2$—CN), 4.32(2H, q,—CO, —CH$_2$—CH$_3$), 6.16(1H, d, J=10Hz, N—CH=CH—CN), 6.67(2H, d, J=9.2Hz, ArH), 7.93(2H, d, J=9.2Hz, ArH)

The Z isomer (0.1 g) prepared above was converted into the title compound (0.2 g, 29%) by the use of LDA through ring closure in a similar manner to that of the Preparative Example 3.

$^1$H-NMR (CDCl$_3$) δ(ppm): 1.36 (3H, t, CO$_2$CH$_2$CH$_3$), 2.83 (3H, s, N—Me), 3.65 (2H, br, NH$_2$), 3.71 (2H, t, J=6Hz,

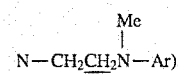

4.04 (2H, t, J=6Hz,

4.31 (2H, q, CO$_2$CH$_2$CH$_3$), 5.6 (1H, d, J=3.2Hz, pyrrole 4-H), 6.36 (1H, d, J=3.2Hz, pyrrole 5-H), 6.56 (2H, d, J=9.2Hz, ArH), 7.9 (2H, d, J=9.2Hz, ArH).

EXAMPLE 16

Ethyl 4-N-[2-(2,4-diaminopyrrolo[3,2-d]pyrimidin-5-yl)ethyl]methylaminobenzoate

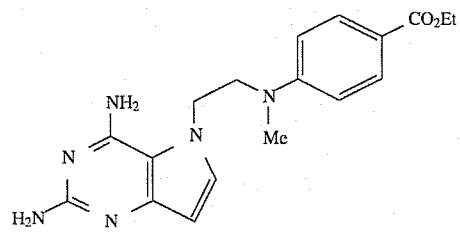

The compound prepared in the above Preparative Example 24 was converted into the title compound (120 mg, 52%) by converting the 3-amino-2-cyanopyrrole moiety into a pyrrolopyrimidine ring through ring closure in a similar manner to that of the Example 1.

$^1$H-NMR (CDCl$_3$) δ(ppm): 1.33 (3H, t, CO$_2$CH$_2$CH$_3$), 2.73 (3H, s, N—Me), 3.78 (2H, t, J=4.8Hz,

4.25 (2H, q, CO$_2$CH$_2$CH$_3$), 4.53 (2H, t, J=4.8Hz,

6.08 (1H, d, J=2.8Hz, 7-H), 6.48 (2H, d, J=9.2Hz, ArH), 7.1 (1H, d, J=2.8Hz, 6-H), 7.71 (2H, d, J=9.2Hz, ArH).

EXAMPLE 17

4-N-[2-(2,4-Diaminopyrrolo[3,2-d]pyrimidin-5-yl)ethyl]methylaminobenzoic acid

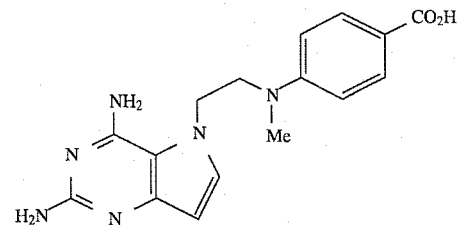

The pyrrolopyrimidine derivative (120 mg) prepared in the Example 16 was dissolved in ethanol (10 ml), followed by the addition of 1N sodium hydroxide (5 ml). The obtained mixture was heated under reflux to complete a reaction. The reaction mixture was neutralized with 1N HCl and distilled to remove the solvent. The obtained residue was subjected to silica gel column chromatography and eluted with a solvent (an 8:1:1 ethyl acetate/methanol acetic acid mixture) to give 100 mg (90%) of the title compound.

$^1$H-NMR (CD$_3$OD) δ(ppm): 2.75 (3H, s, N—Me), 3.78 (2H, t, J=4.8Hz,

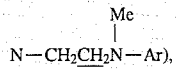

N—CH$_2$<u>CH$_2$</u>N—Ar), 4.56(2H, t, J=4.8Hz,

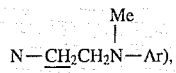

N—<u>CH$_2$</u>CH$_2$N—Ar), 6.15 (1H, d, J=2.8Hz, 7-H), 6.49 (2H, d, J=9.2Hz, ArH), 7.14 (1H, d, J=2.8Hz, 6-H), 7.76 (2H, d, J=9.2Hz, ArH).

EXAMPLE 18

N-[4-N-[2-(2,4-Diaminopyrrolo[3,2-d]pyrimidin-5-yl)ethyl]methyl aminobenzoyl]-L-glutamic acid

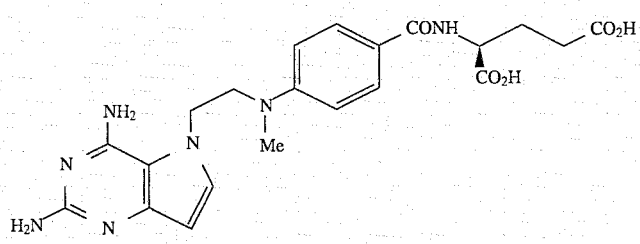

The carboxylic acid derivative (100 mg) prepared in the Example 17 was condensed with diethyl L-glutamate by the use of DPPA in a similar manner to that of the Example 2 and the condensate was hydrolyzed with an alkali to give 31 mg (21%) of the title compound as a crystalline substance.

mol. form.: C$_{21}$H$_{25}$N$_7$O$_5$ (MW: 455.47)

$^1$H-NMR (CD$_3$OD) δ(ppm): 1.98–2.37 (2H, m, NHCHCH$_2$CH$_2$CO$_2$H), 2.39–2.54 (2H, m, NHCHCH$_2$CH$_2$CO$_2$H ), 2.78 (3H, s, N—Me), 3.54–3.84 (2H, m,

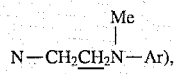

N—CH$_2$<u>CH$_2$</u>N—Ar), 4.46–4.61 (3H, m,

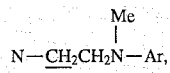

N—<u>CH$_2$</u>CH$_2$N—Ar,

—NHCH—), 6.48 (2H, d, J=9.2Hz, ArH), 7.16 (1H, d, J=2.8Hz, 6-H), 7.61 (2H, d, J=9.2Hz, ArH).

PREPARATIVE EXAMPLE 25

3-(N-Carboethoxymethyl)aminoacrylonitrile

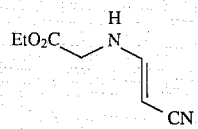

Ethyl aminoacetate hydrochloride (36 g), sodium acetate (32 g) and 3-dimethylaminoacrylonitrile (12.5 g) were added to a mixture comprising ethanol (300 ml) and water (20 ml). The obtained mixture was stirred at room temperature to complete a reaction, followed by the addition of water. The resulting mixture was extracted with ethyl acetate and the organic phase was distilled to remove the solvent. The obtained residue was subjected to silica gel column chromatography and eluted with a solvent (a 1:3 ethyl acetate/hexane mixture) to give 27.8 g (69%) of the objective compound.

$^1$H-NMR (CDCl$_3$) δ(ppm): 1.29 (3H, t, CO$_2$CH$_2$C, H$_2$), 3.71 (2H, d, J=3Hz, N—CH$_2$—CO$_2$Et), 3.88 (1H, d, J=16Hz, olefinic proton), 4.29 (2H, q, CO$_2$CH$_2$CH$_3$), 5.29 (br, NH), 7.07 (1H, dd, J=8Hz, J=16Hz, olefinic proton).

PREPARATIVE EXAMPLE 26 t-Butyl 4-[3-(3-amino-2-carboethoxypyrrol-1-yl)propyl]benzoate

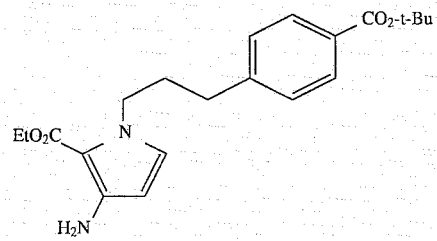

E-t-Butyl 4-[3-[3-(N-carboethoxymethyl)-N-β-cyanovinylamino]propyl]benzoate (4.8 g) shown below was prepared from 3-(N-carboethoxymethyl)aminoacrylonitrile (4.5 g) and the t-butyl 4-(3-iodopropyl)benzoate (10.1 g) prepared in the Preparative Example 2 in a similar manner to that of the Preparative Example 3 (44%).

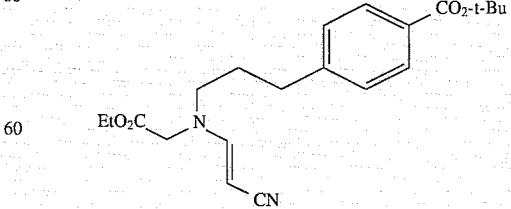

NMR (CDCl$_3$) δ(ppm): 1.28(3H, t, CO$_2$—CH$_2$—CH$_3$), 1.59(9H, s, t-Bu), 1.86–1.96(2H, m, N—CH$_2$—CH$_2$—CH$_2$—Ar), 2.68(2H, t, J=7.6Hz, N—CH$_2$—CH$_2$—CH$_2$—

Ar), 3.18(2H, t, J=7.6Hz, —N—CH$_2$—CH$_2$—CH$_2$—Ar), 3.76(1H, d, J=13.6Hz, —N—CH=CH—CN), 3.77(2H, s,N—CH$_2$—CO$_2$Et), 4.21(2H, q, CO,—CH$_2$—CH$_3$), 6.89(1H, d, J=13.6Hz, N—CH=CH—CN), 7.21 (2H, d, J=8.4Hz, ArH), 7.93(2H, d, J=8.4Hz, ArH).

Z-t-Butyl 4-[3-[3-(N-carboethoxymethyl)-N-β-cyanovinylamino]propyl]benzoate (1.48 g) shown below was prepared by irradiating the E isomer (4.8 g) prepared above with light in a similar manner to that of the Preparative Example 3 (31%).

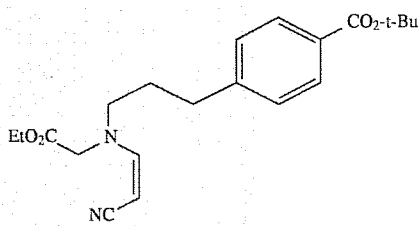

NMR (CDCl$_3$) δ(ppm): 1.29(3H, t, CO$_2$—CH$_2$—CH$_3$), 1.59(9H, s, t-Bu), 1.89–1.97(2H, m, N—CH$_2$—CH$_2$—CH$_2$—Ar), 2.72(2H, t, J=7.6Hz, N—CH$_2$—CH$_2$—CH$_2$—Ar), 3.34(2H, t, J=7.6Hz, N—CH$_2$—CH$_2$—CH$_2$—Ar), 3.75(1H, d, J=10Hz, N—CH—CH—CN), 4.08(2H, s, N—CH$_2$—CO$_2$Et), 4.24(2H, q, CO$_2$—CH$_2$—CH$_3$), 6.24(1H, d, J=10Hz, N—CH=CH—CN), 7.22(2H, d. J=8.4Hz, ArH), 7.9(2H, d, J=8.4Hz, ArH).

The Z isomer (1.48 g) prepared above in toluene (5 ml) was dropped into a t-BuOK (0.3 g)/toluene (20 ml) mixture under cooling with ice. The obtained mixture was stirred under cooling with ice to complete a reaction. The reaction mixture was poured into a saturated aqueous solution of ammonium chloride and the resulting mixture was extracted with toluene. The organic phase was distilled to remove the solvent and the residue was subjected to silica gel column chromatography and eluted with a solvent (a 1:3 ethyl acetate/hexane mixture) to give the title compound (0.6 g, 67%).

NMR (CDCl$_3$) δ(ppm): 1.35(3H, t, CO$_2$—CH$_2$—CH$_3$), 1.58(9H, s, t-Bu), 1.99–2.07(2H, m, N—CH$_2$—CH$_2$—Ar), 2.61 (2H, t. J=7.2Hz, N—CH$_2$—CH$_2$—CH$_2$—Ar), 4.13(2H, t, J=7.2Hz, N—CH$_2$—CH$_2$—CH$_2$—Ar), 4.3(2H, q, CO$_2$—CH$_2$—CH$_3$), 5.6(1H, d, J=2.8Hz, pyrrole-4H). 6.53(1H, d. J=2.8Hz, pyrrole-5H), 7.19(2H, d, J=8.4Hz, ArH), 7.89(2H, d, J=8.4Hz, ArH).

EXAMPLE 19 t-Butyl 4-[3-(2-amino-4-hydroxypyrrolo[3,2-d]pyrimidin-5-yl)propyl]benzoate

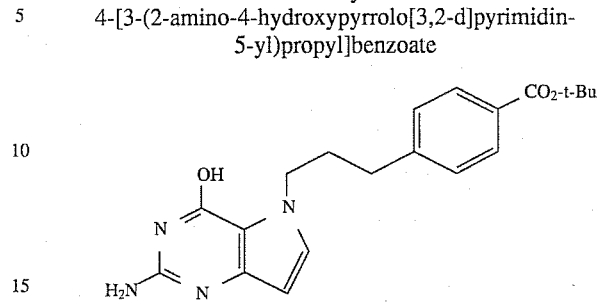

The compound prepared in the Preparative Example 26 was converted into the title compound by converting the 3-amino-2-carboethoxypyrrole moiety into a pyrrolopyrimidine ring through ring closure in a similar manner to that of the Example 1. 0.5 g (85%) of the title compound was obtained.

mol. form.: C$_{20}$H$_{24}$N$_4$O$_3$ (MW: 368.43)

MS: FAB-MS m/z: 369 (M+H)$^+$

NMR (CD$_3$OD) δ(ppm): 1.57(9H, s, t-Bu), 2.11–2.19(2H, m. N—CH$_2$—CH$_2$—CH$_2$—Ar), 2.65(2H, t, J=7.2Hz, N—CH$_2$—CH$_2$—CH$_2$—Ar), 4.33(2H, t,J=7.2Hz, N—CH$_2$—CH$_2$—CH$_2$—Ar), 6.02(1H, d, J=2.8Hz. 7H), 7.17(1H, d, J=2.8Hz, 6H), 7.24(2H, d, J=8.4Hz. ArH), 7.83(2H, d, J=8.4Hz, ArH).

PREPARATIVE EXAMPLE 20

N-[4-[3-(2-Amino-4-hydroxypyrrolo[3,2-d]pyrimidin-5-yl)propyl]benzoyl]-L-glutamic acid

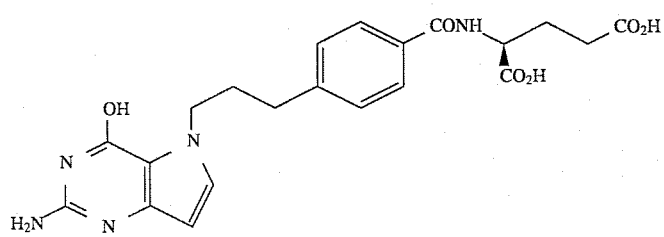

The compound prepared in the Example 19 was condensed with L-glutamic acid by the use of DPPA in a similar manner to that of the Example 2 to give the title compound.

mol. form.: C$_{21}$H$_{23}$N$_5$O$_6$ (MW: 441.44).

PREPARATIVE EXAMPLE 101

Preparation of 2-cyano-2-cyclopenten-1-one

A solution of p-toluenethiol (13.7 g, 0.11 mol) in anhydrous methylene chloride was stirred under cooling with ice in a nitrogen stream, followed by the addition of a solution of trimethylaluminium (7.9 g, 0.11 mol) in hexane. The obtained mixture was stirred for about 20 minutes and cooled in a dry ice-acetone bath, followed by the dropwise addition of a solution of 2-cyclopentenone (8.41 g, 0.10 mol)

in methylene chloride. The obtained mixture was further stirred for 30 minutes and diluted with anhydrous tetrahydrofuran, followed by the addition of a solution of p-toluenesulfonyl cyanide (22.9 g, 0.12 mol) in tetrahydrofuran at −50° C. or below. The mixture thus obtained was stirred for about 30 minutes and further in an ice bath for about 60 minutes. About 40 ml of methanol was dropped into the resulting mixture, followed by the addition of diethyl ether. The obtained mixture was washed with aqueous hydrochloric acid, an aqueous solution of sodium hydrogencarbonate and an aqueous solution of common salt, dehydrated and concentrated. The concentrated solution gave 2-cyano-3-(4-methylphenyl)thio-1-cyclopentanone as a crystalline powder by allowing the solution as such to stand or by adding a small amount of an n-hexane/ethyl acetate (1:1) mixture to the solution and allowing the obtained mixture to stand. yield: 22 g $^1$H-NMR (CDCl$_3$) δ(ppm): 1.82~2.00 (m, 1H), 2.37 (s, 3H), 2.30~2.60 (m, 3H), 3.04 (d, J=9.6Hz, 1H), 3.68~3.78 (m, 1H), 7.20 (d, J=8.4Hz, 2H), 7.42 (d, J=8.4Hz, 2H).

The above product (10 g, 43 mmol) was dissolved in tetrahydrofuran, adsorbed on silica gel column and chromatographed with an n-hexane/ethyl acetate mixture as a developer. The fractions containing the objective compound were concentrated. The objective compound was obtained as a colorless to yellow oil. yield: 2.9 g $^1$H-NMR (CDCl$_3$) δ(ppm): 2.55~2.58 (m, 2H), 2.90~2.94 (m, 2H), 8.32 (t, J=2.8Hz, 1H)

IR (neat) v(cm$^{-1}$): 2238, 1728, 1607.

PREPARATIVE EXAMPLE 102

Preparation of t-butyl 4-vinylbenzoater

A 1.6M solution of n-butyllithium (49.7 mmol) in hexane was added to a suspension of methyltriphenylphosphonium bromide (18.2 g, 50.9 mmol) in anhydrous tetrahydrofuran under cooling with dry ice/acetone in a nitrogen stream. The obtained mixture was stirred for a while and thereafter, under cooling with ice for about 30 minutes, followed by the addition of a solution of t-butyl terephthalaldehydate (10 g, 48.5 mmol) in anhydrous tetrahydrofuran. The obtained mixture was stirred for about 40 minutes. The reaction mixture was filtered to remove a formed precipitate and the filtrate was concentrated to dryness. The obtained residue was purified by silica gel column chromatography (developer: n-hexane/ethyl acetate=20:1) to give the objective compound. yield: 8.47

$^1$H-NMR (CDCl$_3$) δ(ppm): 1.59 (s, 9H), 5.36 (d-d, J=0.8Hz, 10.8Hz, 1H), 5.84 (d-d, J=0.8Hz, 17.6Hz, 1H), 6.74 (d-d, J=10.8Hz, 17.6Hz, 1H), 7.43 (d, J=8.0Hz, 2H), 7.94 (d, J=8.0Hz, 2H)

IR (neat) v(cm$^{-1}$): 2978, 1710, 1292, 1166, 916.

PREPARATIVE EXAMPLE 103

Preparation of t-butyl 4-(2-hydroxyethyl)benzoate

A solution of 9-borabicyclo[3.3.1]nonane (9-BBN, 5.65 g, 46.3 mmol) in anhydrous tetrahydrofuran was added to a solution of t-butyl 4-vinylbenzoate (8.47 g, 42.1 mmol) prepared in the Preparative Example 102 in anhydrous tetrahydrofuran in a nitrogen stream. The obtained mixture was stirred at room temperature for 3 hours. 15 ml of water and 17 ml of 3N NaOH were added to the reaction mixture successively, followed by the dropwise addition of 30% aqueous hydrogen peroxide at 50° C. or below. The obtained mixture was stirred as such for one hour and poured into water. The mixture thus obtained was extracted with ethyl acetate. The organic phase was washed with an aqueous solution of common salt, dehydrated and distilled to remove the solvent. The obtained residue was purified by silica gel column chromatography (developer: n-hexane/ethyl acetate=1:1) to give the objective compound. yield: 8.71 g $^1$H-NMR (CDCl$_3$) δ(ppm): 1.41 (t, J=6.6Hz), 1.59 (s, 9H), 2.92 (t, J=6.6Hz, 2H), 3.88 (q, J=6.6Hz, 2H), 7.28 (d, J=8.0Hz, 2H), 7.93 (d, J=8.0Hz, 2H)

IR (neat) v(cm$^{-1}$): 3150~3700, 2978, 1713, 1294, 1167.

PREPARATIVE EXAMPLE 104

Preparation of t-butyl 4-(2-bromoethyl)benzoate

A solution of methanesulfonyl chloride (5.8 g, 50.8 mmol) in methylene chloride was dropped into a solution of t-butyl 4-(2-hydroxyethyl)benzoate (8.7 g, 39.1 mmol) prepared in the Preparative Example 103 and triethylamine (5.9 g, 58.7 mmol) in methylene chloride under cooling with dry ice/acetone. The obtained mixture was stirred under cooling with ice for 30 minutes, followed by the addition of a 0.5 N aqueous solution of sodium hydrogensulfite. The mixture thus obtained was stirred. The organic phase was recovered from the mixture, washed with an aqueous solution of common salt, dried and distilled to remove the solvent. 11.7 g of a methanesulfonic ester was obtained. This ester was dissolved in 2-butanone, followed by the addition of lithium bromide (5.1 g, 58.4 mmol). The obtained mixture was stirred in a nitrogen stream at 65° C. for 12 hours and allowed to stand at room temperature. A formed precipitate was filtered out and the filtrate was concentrated to dryness. The residue was purified by silica gel column chromatography (developer: n-hexane/ethyl acetate=4:1) to give 9.8 g of the objective compound as a colorless to light brown crystal.

$^1$H-NMR (CDCl$_3$) δ(ppm): 1.59 (s, 9H), 3.21 (t, J=7.2Hz, 2H), 3.58 (t, J=7.2Hz, 2H), 7.26 (d, J=8.0Hz, 2H), 7.94 (d, J=8.0Hz, 2H).

PREPARATIVE EXAMPLE 105

Preparation of t-butyl 4-(2-(2-cyano-1-cyclopentanon- 3-yl)ethyl]benzoate

A solution of the 2-cyano-2-cyclopenten-1-one (2.41 g, 22.5 mmol) prepared in the Preparative Example 101 in anhydrous benzene and a solution of azobisisobutyronitrile (AIBN) (0.05 g, a catalytic amount) and tri-n-butyltin hydride (3.62 g, 12.4 mmol) in anhydrous benzene were simultaneously gradually dropped into a solution of t-butyl 4-(2-bromoethyl)benzoate (3.21 g, 11.3 mmol) prepared in the Preparative Example 104 in anhydrous benzene under reflux by heating. The obtained mixture was heated under reflux for about 20 minutes and distilled to remove the solvent. The residue was purified by silica gel column chromatography to give the objective compound. yield: 0.43 g $^1$H-NMR (CDCl$_3$) δ(ppm): 1.59 (s, 9H), 1.78~1.96 (m, 1H), 2.02~2.22 (m, 1H), 2.24~2.58 (m, 4H), 2.76~2.94 (m, 3H), 7.26 (d, J=8.2Hz, 2H), 7.93 (d, J=8.2Hz, 2H)

IR (neat) v(cm$^{-1}$): 2977, 2933, 2246, 1760, 1713

Mass(FAB) M+H$^+$=314.

PREPARATIVE EXAMPLE 106

Preparation of t-butyl
4-[2-(2-cyano-3-methoxy-2-cyclopentenyl)ethyl]
benzoate t-Butyl 4-[2-(2-cyano-1-cyclopentanon-3-yl)ethyl]benzoate (0.43 g, 1.37 mmol) prepared in the Preparative Example 105 and N,N-diisopropylethylamine (0.21 g, 1.64 mmol) were dissolved in a methanol/acetonitrile (1:5) mixture, followed by the addition of 3.2 g of a 10% by weight solution of trimethylsilyldiazomethane in hexane. The obtained mixture was stirred at room temperature for 2 hours, followed by the addition of a small amount of acetic acid. The mixture this obtained was stirred and distilled to remove the solvent. The residue was dissolved in diethyl ether, washed with diluted hydrochloric acid, dilute alkali ind an aqueous solution of common salt, dehydrated and concentrated to dryness. The residue was purified by silica gel column chromatography to give the objective compound. yield: 0.23 g $^1$H-NMR (CDCl$_3$) δ(ppm): 1.52~1.72 (m, 2H), 1.59 (s, 9H), 2.02~2.18 (m, 2H), 2.46~2.52 (m, 2H), 2.62~2.82 (m, 2H), 2.82~2.94 (m, 1H), 4.05 (s, 3H), 7.24 (d, J=8.2Hz, 2H), 7.90 (d, J=8.2Hz, 2H)

IR (neat) ν(cm$^{-1}$): 2977, 2933, 2203, 1710, 1632

Mass(FAB) M+H$^+$=328.

EXAMPLE 101

Preparation of t-butyl
4-[2-(2,4-diamino-6,7-dihydro-
5H-cyclopenta[d]pyrimidin-5-yl)ethyl]benzoate The compound (0.23 g, 0.7 mmol) prepared in the Preparative Example 106 and guanidine carbonate (0.63 g, 3.5 mmol) were mixed with 2-methyl-2-propanol. The obtained mixture was put in a pressure reactor in a nitrogen atmosphere and heated at 155°±3° C. under stirring for 8 hours, followed by the addition of additional guanidine carbonate (0.25 g, 1.4 mmol). The contents were stirred under heating at 185°±3° C. for 17 hours. The reaction mixture was cooled by allowing to stand and filtered to remove a precipitate. The filtrate was concentrated and the residue was purified by silica gel column chromatography (developer: chloroform/methanol=10:1) to give the objective compound as a white powder. yield: 0.25 g $^1$H-NMR (CDCl$_3$) δ(ppm): 1.59 (s, 9H), 1.64~1.78 (m, 1H), 1.84~1.98 (m, 2H), 2.16~2.28 (m, 1H), 2.60~2.71 (m, 2H), 2.71~2.80 (m, 1H), 2.80~2.91 (m, 1H), 2.95~3.05 (m, 1H), 4.40~4.47 (br, 2H), 4.63~4.70 (br, 2H), 7.23 (d, J=8.0Hz, 2H), 7.91 (d, J=8.0Hz, 2H)

IR (neat) ν(cm$^{-1}$): 3330, 3145, 1708, 1610, 1584

Mass(FAB) M+H$^+$=355.

EXAMPLE 102

Preparation of
4-[2-(2,4-diamino-6,7-dihydro-5H-cyclopenta[d]
pyrimidin-5-yl)ethyl]benzoic acid The compound (0.19 g, 0.54 mmol) prepared in the Example 101 was dissolved in a dioxane/water/concentrated hydrochloric acid (20:5:1) mixture. The obtained solution was heated under reflux for 4 hours and concentrated. Water and 1N sodium hydroxide were added to the residue to adjust the pH to above 10. The obtained mixture was filtered to remove insolubles. The filtrate was neutralized by the gradual addition of 1N hydrochloric acid to give a white precipitate. This precipitate was recovered by filtration and dried to give the objective compound. yield: 0.08 g $^1$H-NMR (CD$_3$OD) δ(ppm): 1.66~1.78 (m, 1H), 1.94~2.14 (m, 2H), 2.28~2.42 (m, 1H), 2.70~2.84 (m, 3H), 2.92~3.04 (m, 1H), 3.18~3.26 (m, 1H), 7.31 (d, J=8.4Hz, 2H), 7.92 (d, J=8.4Hz, 2H)

Mass(FAB) M+H$^+$=299.

EXAMPLE 103

Preparation of N-{4-[2-(2,4-diamino-6,7-dihydro-
5H-cyclopenta[d]pyrimidin-5-yl)ethyl]benzoyl}-
L-glutamic The compound (0.08 g, 0.27 mmol) prepared in the Example 102 and diethyl L-glutamate hydrochloride (0.137 g, 0.57 mmol) were suspended in anhydrous dimethylformamide and the obtained suspension was stirred under cooling with Ice in a nitrogen stream, followed by the addition of triethylamine (0.13 g, 1.28 mmol) and diphenylphosphoryl azide (0.16 g, 0.57 mmol). The obtained mixture was stirred under cooling with ice for about 2 hours and then at room temperature for about one hour and filtered to remove insolubles. The filtrate was concentrated and the residue was purified by silica gel column chromatography (developer: chloroform/methanol=10:1). The obtained diethyl ester compound was dissolved in a mixture comprising 10 ml of ethanol and 1.7 ml of 1N sodium hydroxide. The obtained solution was stirred at room temperature for 12 hours, followed by the addition of a small amount of water. The obtained mixture was filtered and the filtrate was concentrated, followed by the addition of 1N hydrochloric acid. A white precipitate thus formed was recovered by filtration and purified by silica gel column chromatography (developer: chloroform/methanol/acetic acid=10:1:1). The product thus purified was further purified by dissolving it in a dilute alkali and adding diluted hydrochloric acid to the solution to conduct reprecipitation. The objective compound was obtained as a white powder.

$^1$H-NMR (DMSO-d$_6$) δ(ppm): 1.45~1.57 (m, 1H), 1.76~2.00 (m, 3H), 2.00~2.12 (m, 2H), 2.33 (t, J=7.6Hz, 2H), 2.42~2.52 (m, 1H), 2.60~2.77 (m, 3H), 3.01~3.10 (m, 1H), 4.33~4.41 (m, 1H), 6.00~6.16 (br, 2H), 6.36~6.50 (br, 2H), 7.30 (d, J=8.0Hz, 2H), 7.78 (d, J=8.0Hz, 2H), 8.43 (d, J=6.8Hz, 1H)

Mass(FAB) M+H$^+$=428.

PREPARATIVE EXAMPLE 107

Preparation of t-butyl
5-(2-ethoxycarbonyl-E-ethenyl)-
2-thiophenecarboxylate

A solution of t-butyl 2-thiophenecarboxylate (1.84 g, 10 mmol) and N,N,N',N'-tetramethylethylenediamine (1.74 g, 15 mmol) in anhydrous tatrahydrofuran was stirred in a nitrogen stream under cooling with dry ice/acetone, followed by the dropwise addition of a 1.7M solution (8.0 ml) of t-butyllithium (13.6 mmol) in pentane. The obtained mixture was stirred as such for about 50 minutes. Anhydrous dimethylformamide (15 ml) was gradually dropped into the resulting mixture to conduct a reaction. The dry ice/acetone was removed to raise the temperature of the mixture to room one. The resulting mixture was stirred for 40 minutes and poured into 300 ml of a diethyl ether/0.3 N HCl (3:1)

mixture. The obtained mixture was stirred for a while. The organic layer was recovered, washed with a phosphate buffer solution having a pH of 7 and an aqueous solution of common salt, dehydrated and distilled to remove the solvent. The residue was purified by silica gel column chromatography (developer: n-hexane/ethyl acetate=8:1) to give t-butyl 5-formyl-2-thiophenecarboxylate. yield: 1.7 g $^1$H-NMR (CDCl$_3$) δ(ppm): 1.59 (s, 9H), 7.70 (d, J=4.0Hz, 1H), 7.75 (d, J=4.0Hz, 1H), 9.95 (s, 1H)

IR (neat) ν(cm$^{-1}$): 2981, 1713, 1682.

Sodium hydride (min 60% paraffinic dispersion, 1.88 g, about 47 mmol) was washed with anhydrous hexane in a nitrogen stream and suspended in anhydrous tetrahydrofuran. The obtained suspension was stirred under cooling with ice, followed by the gradual dropwise addition of a solution of ethyl diethylphosphonoacetate (10.53 g, 47 mmol) in anhydrous tetrahydrofuran. The obtained mixture was stirred at room temperature for 15 minutes. A solution of the t-butyl 5-formyl-2-thiophenecarboxylate (6.65 g, 31.3 mmol) prepared above in anhydrous tetrahydrofuran was gradually dropped into the resulting mixture under cooling with ice. The obtained mixture was stirred at room temperature for 30 minutes, diluted with diethyl ether, washed with a dilute alkali, diluted hydrochloric acid and an aqueous solution of common salt, dehydrated and evaporated in a vacuum to dryness. The residue was purified by silica gel column chromatography (developer: n-hexane/ethyl acetate=8:1) to give the objective compound. yield: 7.58 g $^1$H-NMR (CDCl$_3$) δ(ppm): 1.33 (t, J=7.2Hz, 3H)0 1.57 (s, 9H), 4.25 (q, J=7.2Hz, 2H), 6.33 (d, J=15.6Hz, 1H), 7.18 (d, J=4.0Hz, 1H), 7.61 (d, J=4.0Hz, 1H), 7.70 (d, J=15.6Hz, 1H)

IR (neat) ν(cm$^{-1}$): 2980, 1713, 1706, 1630, 969.

PREPARATIVE EXAMPLE 108

Preparation of t-butyl 5-(2-ethoxycarbonylethyl)-2-thiophenecarboxylate

The α,β-unsaturated ester (7.58 g, 26.8 mmol) prepared in the Preparative Example 107 was catalytically reduced in the presence of 10% palladium-carbon (1.05 g) in ethanol at room temperature. After the completion of the reaction, the catalyst was filtered out and the filtrate was concentrated and evaporated in a vacuum to dryness, giving the objective compound. yield: 7.6 g $^1$H-NMR (CDCl$_3$) δ(ppm): 1.26 (t, J=7.2Hz, 3H), 1.56 (s, 9H), 2.68 (t, J=7.6Hz, 2H), 3.15 (t-d, J=7.6Hz, 0.8Hz, 2H), 4.15 (q, J=7.2Hz, 2H), 6.79 (dr, J=3.6Hz, 0.8Hz, 1H), 7.54 (d, J=3.6Hz, 1H).

PREPARATIVE EXAMPLE 109

Preparation of t-butyl 5-(3-hydroxypropyl)-2-thiophenecarboxylate

The diester (7.6 g, 26.8 mmol) prepared in the Preparative Example 108 was partially hydrolyzed in an ethanol/1N aqueous sodium hydroxide mixture at room temperature to give 6.1 g of 3-(5-t-butoxycarbonylthiophen-2-yl)propionic acid. This acid was dissolved in anhydrous tetrahydrofuran and the obtained solution was dropped into a borane-tetrahydrofuran solution prepared from sodium borohydride (3.37 g, 89 mmol) and a trifluoroborane-diethyl ether complex (16.9 g, 119 mmol) in about 30 minutes under cooling with ice. The obtained mixture was stirred for 30 minutes, followed by the dropwise addition of methanol. After the generation of hydrogen gas had discontinued, the reaction mixture was filtered and the filtrate was evaporated to dryness. Methanol was added to the residue to remove the boron compound by azeotropic distillation. The residue was dissolved in diethyl ether, and the solution was washed with diluted hydrochloric acid and an aqueous solution of common salt, dehydrated and distilled to remote the solvent. The residue was dried in a vacuum to give the objective compound. yield: 6.0 g $^1$H-NMR (CDCl$_3$) δ(ppm): 1.56 (s, 9H), 1.94 (tt, J=7.6Hz, J=6.4Hz, 2H), 2.93 (J=7.6Hz, 0.8Hz, 2H), 3.70 (t, J=6.4Hz, 2H), 6.78 (dr, J=3.6Hz, 0.8Hz, 1H), 7.54 (d, J=3.6Hz, 1H)

IR (neat) ν(cm$^{-1}$): 3200~3700, 2978, 2935, 1703.

PREPARATIVE EXAMPLE 110

Preparation of t-butyl 5-(3-bromopropyl)-2-thiophenecarboxylate

The alcohol (6.0 g, 23.9 mmol) prepared in the Preparative Example 109 was converted into a corresponding bromide according to the same procedure as that of the Preparative Example 104. yield: 6.2 g $^1$H-NMR (CDCl$_3$) δ(ppm): 1.56 (s, 9H), 2.21 (tt, J=7.6Hz, 6.4Hz, 2H), 3.00 (td, J=7.2Hz, 0.8Hz, 2H), 3.42 (t, J=6.4Hz, 2H), 6.81 (dr, J=3.6Hz, 0.8Hz, 1H), 7.55 (d, J=3.6Hz, 1H).

PREPARATIVE EXAMPLE 111

Preparation of t-butyl 5-[3-(2-cyano-1-cyclopentanon-3-yl)propyl]-2-thiphenecarboxylate The bromide (4.25 g, 14 mmol) prepared in the Preparative Example 110 was converted into the objective compound according to the same procedure as that of the Preparative Example 105. yield: 0.83 g $^1$H-NMR (CDCl$_3$) δ(ppm): 1.40~1.72 (m, 2H), 1.56 (s, 9H), 1.74~1.94 (m, 2H), 2.24~2.56 (m, 4H), 2.83 (d, J=12Hz, 1H), 2.82~2.94 (m, 2H), 6.77 (dt, J=3.6Hz, 0.8Hz, 1H), 7.55 (d, J=3.6Hz, 1H)

IR (neat) ν(cm$^{-1}$): 2979, 2935, 2246, 1760, 1704

Mass(FAB) M+H$^+$=334.

PREPARATIVE EXAMPLE 112

Preparation of t-butyl 5-[3-(2-cyano-3-methoxy-2-cyclopentenyl)propyl]-2-thiophenecarboxylate The compound (0.83 g, 2.5 mmol) prepared in the Preparative Example 111 was converted into the objective compound according to the same procedure as that of the Preparative Example 106. yield: 0.82 g $^1$H-NMR (CDCl$_3$) δ(ppm): 1.40~1.84 (m, 5H), 1.56 (s, 9H), 2.02~2.14 (m, 1H), 2.44~2.50 (m, 2H), 2.78~2.92 (m, 3H), 4.04 (s, 3H), 6.76 (d, J=3.6Hz, 1H), 7.54 (d, J=3.6Hz, 1H)

IR(neat) ν(cm$^{-1}$): 2978, 2936, 2204, 1704, 1632

Mass(FAB) M+H$^+$=348.

EXAMPLE 104

Preparation of 5-[3-(2,4-diamino-6,7-dihydro-5H-cyclopenta[d]pyrimidin-5-yl)propyl]-2-thiophenecarboxylic acid The compound (0.82 g, 2.35 mmol) prepared in the Preparative Example 112 and guanidine carbonate (4.3 g, 23.6 mmol) were mixed with 2-methyl-2-propanol. The obtained mixture was put in a pressure reactor in a nitrogen atmosphere and heated under stirring at 155°±3° C. for 24 hours and then at 180°±3° C. for 40 hours. The reaction mixture was cooled by allowing to stand and filtered. The filtrate was evaporated in a vacuum to dryness. The obtained residue was purified by silica gel column chromatography (developer: chloroform/methanol/acetic acid=20:2:1 to 10:2:1). The product thus purified was further purified by dissolving it in a dilute alkali and adding diluted hydrochloric acid to the solution to conduct reprecipitation. The objective compound was obtained as a white powder. yield: 0.33 g $^1$H-NMR (CDCl$_3$) δ(ppm): 1.2~1.3 (m, 1H), 1.5~1.7 (m, 4H), 1.9~2.1 (m, 1H), 2.35~2.5 (m, 1H), 2.5~2.7 (m, 1H), 2.7~2.8 (m, 2H), 2.9~3.0 (m, 1H), 5.9~6.0 (br, 2H), 6.15~6.3 (br, 2H), 6.84 (d, J=3.6Hz, 1H), 7.45 (d, J=3.6Hz, 1H)

Mass(FAB) M+H$^+$=319.

EXAMPLE 105

Preparation of N-{5-[3-(2,4-diamino-6,7-dihydro-5H-cyclopenta[d]pyrimidin-5-yl)propyl]-2-thenoyl}-L-glutamic acid The carboxylic acid (0.30 g, 0.94 mmol) prepared in the Example 104 was converted into a corresponding glutamic acid derivative according to the same procedure as that of the Example 103. yield: 0 15 g $^1$H-NMR (DMSO-d$_6$) δ(ppm): 1.20~1.32 (m, 1H), 1.54~1.72 (m, 4H), 1.82~2.08 (m, 3H), 2.24~2.46 (m, 3H), 2.56~2.68 (m, 1H), 2.74~2.82 (m, 2H), 2.92~3.01 (m, 1H), 4.24~4.36 (m, 1H), 5.80~5.90 (br, 2H), 6.10~6.30 (br, 2H), 6.85 (d, J=3.6Hz, 1H), 7.65 (d, J=3.6Hz, 1H), 8.39 (d, J=7.6Hz, 1H)

Mass(Fab) M+H$^+$=448.

PREPARATIVE EXAMPLE 113

Preparation of t-butyl 4-(2-ethoxycarbonyl-E-ethenyl)benzoate t-Butyl terephthalaldehydate (30 g, 0.146 mol) was converted into a corresponding α,β-unsaturated ester according to the same procedure as that of the Preparative Example 107. yield: 38.5 g $^1$H-NMR (CDCl$_3$) δ(ppm): 1.35 (t, J=7.2Hz, 3H ), 1.60 (s, 9H), 4.28 (q, J=7.2Hz, 2H), 6.51 (d, J=16.0Hz, 1H), 7.56 (d, J=8.8Hz, 2H), 7.70 (d, J=16.0Hz, 1H), 7.99 (d, J=8.8Hz, 2H).

PREPARATIVE EXAMPLE 114

Preparation of t-butyl 4-(2-ethoxycarbonylethyl)benzoate

The α,β-unsaturated ester (38.5 g, 0.139 mol) prepared in the Preparative Example 113 was converted into the objective compound according to the same procedure as that of the Preparative Example 108. yield: 38 g $^1$H-NMR (CDCl$_3$) δ(ppm): 1.23 (t, J=7.2Hz, 3H), 1.58 (s, 9H), 2.63 (t, J=8.0Hz, 2H), 2.99 (t, J=8.0Hz, 2H), 4.12 (q, J=7.2Hz, 2H ), 7.24 (d, J=8.4Hz, 2H), 7.91 (d, J=8.4Hz, 2H).

PREPARATIVE EXAMPLE 115

Preparation of t-butyl 4-(3-hydroxypropyl)benzoate

The diester (38 g, 0.137 mol) prepared in the Preparative Example 114 was converted into a corresponding alcohol according to the same procedure as that of the Preparative Example 109. yield: 25 g $^1$H-NMR (CDCl$_3$) δ(ppm): 1.59 (s, 9H), 1.91 (tt, J=8.0Hz, 6.4Hz, 2H), 2.76 (t, J=8.0Hz, 2H), 3.67 (t, J=6.4Hz, 2H), 7.24 (d, J=8.4Hz, 2H), 7.91 (d, J=8.4Hz, 2H).

PREPARATIVE EXAMPLE 116

Preparation of t-butyl 4-(3-bromopropyl)benzoate

The alcohol (25 g, 0.105 mol) prepared in the Preparative Example 115 was converted into a corresponding bromide according to the same procedure as that of the Preparative Example 104. yield: 25 g $^1$H-NMR (CDCl$_3$) δ(ppm): 1.59 (s, 9H), 2.1~2.22 (m, 2H), 2.83 (t, J=7.2Hz, 2H), 3.38 (t, J=6.4Hz, 2H ), 7.24 (d, J=8.0Hz, 2H), 7.92 (d, J=8.0Hz, 2H).

PREPARATIVE EXAMPLE 117

Preparation of t-butyl 4-[3-(2-cyano-1-cyclopentanon-3-yl)propyl]benzoate

The bromide (1.5 g, 5 mmol) prepared in the Preparative Example 116 was converted into the objective compound according to the same procedure as that of the Preparative Example 105. yield: 0.43 g $^1$H-NMR (CDCl$_3$) δ(ppm): 1.40~1.66 (m, 2H), 1.59 (s, 9H), 1.70~1.92 (m, 3H), 2.20~2.56 (m, 4H), 2.60~2.80 (m, 2H), 2.81 (d, J=11.6Hz, 1H), 7.22 (d, J=8.0Hz, 2H), 7.91 (d, J=8.0Hz, 2H)

IR (neat) ν(cm$^{-1}$): 2958, 2932, 2248, 1760, 1710

Mass (EI) M$^+$=327.

PREPARATIVE EXAMPLE 118

Preparation of t-butyl 4-[3-(2-cyano-3-methoxy-2-cyclopentenyl)propyl]benzoate

The compound (0.41 g) prepared in the Preparative Example 117 was converted into the objective compound according to the same procedure as that of the Preparative Example 106. yield: 0.31 g $^1$H-NMR (CDCl$_3$) δ(ppm): 1.30~1.41 (m, 1H), 1.41~1.55 (m, 1H), 1.59 (s, 9H), 1.55~1.82 (m, 3H), 2.02~2.12 (m, 1H), 2.42~2.48 (m, 2H), 2.61~2.76 (m, 2H), 2.82~2.91 (m, 1H), 4.03 (s, 3H), 7.22 (d, J=8.0Hz, 2H), 7.90 (d, J=8.0Hz, 2H)

IR (neat) ν(cm$^{-1}$): 2978, 2935, 2203, 1712, 1632

Mass(EI) M$^+$=341.

EXAMPLE 106

Preparation of t-butyl 4-[3-(2,4-diamino-6,7-dihydro-5H-cyclopenta[d]pyrimidin-5-yl)propyl]benzoate The compound (1.06 g, 3.1 mmol) prepared in the Preparative Example 118 was converted into the objective compound according to the same procedure as that of the Example 101. yield: 0.95 g $^1$H-NMR (CDCl$_3$) δ(ppm): 1.34~1.47 (m, 1H), 1.56~1.82 (m, 4H), 1.59 (s, 9H), 2.10~2.23 (m, 1H), 2.56~2.86 (m, 4H), 2.95~3.02 (m, 1H), 4.40~4.50 (br, 2H), 4.60~4.70 (br, 2H), 7.21 (d, J=8.4Hz, 2H), 7.90 (d, J=8.4Hz, 2H).

Mass(FAB) M+H$^+$=369.

EXAMPLE 107

Preparation of 4-[3-(2,4-diamino-6,7-dihydro-5H-cyclopenta[d]pyrimidin-5-yl)propyl]benzoic acid The compound (0.73 g, 2.0 mmol) prepared in the Example 106 was converted into a corresponding carboxylic acid according to the same procedure as that of the Example 102. yield: 0.5 g $^1$H-NMR (DMSO-d$_6$) δ(ppm): 1.16~1.32 (m, 1H), 1.50~1.64 (m, 3H), 1.64~1.74 (m, 1H), 1.94~2.08 (m, 1H), 2.40~2.52 (m, 1H), 2.54~2.74 (m, 3H), 2.92~3.02 (m, 1H), 6.20~6.35 (br, 2H), 6.60~6.76 (br, 2H), 7.28 (d, J=8.4Hz, 2H), 7.83 (d, J=8.4Hz, 2H)

Mass(FAB) M+H$^+$=313.

EXAMPLE 108

Preparation of N-{4-[3-(2,4-diamino-6,7-dihydro-5H-cyclopenta[d]pyrimidin-5-yl)propyl]benzoyl-L-glutamic The carboxylic acid (0.1 g, 0.32 mmol) prepared in the Example 107 was converted into a corresponding glutamic acid derivative in a similar manner to that of Example 103. yield: 0.08 g $^1$H-NMR (DMSO-d$_6$) δ(ppm): 1.20~1.30 (br, 1H), 1.50~1.72 (m, 4H), 1.88~2.12 (m, 3H), 2.30~2.37 (m, 2H), 2.37~2.50 (m, 2H), 2.55~2.70 (m, 3H), 2.94~3.02 (m, 1H), 4.30~4.42 (m, 1H), 5.70~5.85 (br, 2H), 6.05~6.20 (br, 2H), 7.27 (d, J=8.0Hz, 2H), 7.78 (d, J=8.0Hz, 2H), 8.36~8.42 (br, 1H)

Mass(FAB) M+H$^+$=442.

PREPARATIVE EXAMPLE 119

Preparation of t-butyl 4-(1-ethyl-3-iodopropyl)benzoate t-Butyl p-formylbenzoate (20 g, 97 mmol) was dissolved in ether (300 ml), followed by the dropwise addition of ethylmagnesium bromide (3M ethereal solution, 33 ml) under cooling with ice. The obtained mixture was stirred to complete a reaction. The reaction mixture was poured into a saturated aqueous solution of ammonium chloride and the obtained mixture was extracted with ether. The organic phase was distilled to remove the solvent and the obtained residue was subjected to silica gel column chromatography and eluted with a solvent (ethyl acetate/hexane=1:4) to give 22.3 g of t-butyl 4-(1-hydroxypropyl)benzoate. This product was dissolved in petroleum ether (500 ml), followed by the addition of active manganese dioxide (165 g). The obtained mixture was heated under reflux for 30 hours to complete a reaction. The reaction mixture was filtered and the filtrate was concentrated to give 21.1 g of t-butyl 4-propionylbenzoate.

The ketone thus prepared was subjected to the Horner-Emmons reaction. That is, potassium t-butoxide (19 g) was added to a solution of ethyl diethylphosphonoacetate (36 ml) in tetrahydrofuran (400 ml). The obtained mixture was stirred at room temperature for 30 minutes, followed by the addition of a solution of the above ketone (21.1 g) in tetrahydrofuran (40 ml). The obtained mixture was stirred at 55° to 65° C. for 1.5 hours to complete a reaction. The reaction mixture was poured into a saturated aqueous solution of ammonium chloride to give 22.7 g of t-butyl 4-(1-ethyl-2-ethoxycarbonyl-E-ethenyl)benzoate.

The α,β-unsaturated ester thus prepared was catalytically reduced with 10% palladium/carbon (0.5 g) in methanol (300 ml) to give t-butyl 4-(1-ethyl-2-ethoxycarbonylethyl)benzoate. This product was added to a mixture comprising a 1N aqueous solution of sodium hydroxide (150 ml) and methanol (150 ml). The obtained mixture was stirred at room temperature for 2 hours to complete a reaction. The reaction mixture was made weakly acidic with 1N aqueous hydrochloric acid and extracted with ethyl acetate. The organic phase was distilled to remove the solvent and the residue was purified by silica gel column chromatography to give 17.7 g of 3-(4-t-butoxycarbonylphenyl)pentanoic acid. This acid was dissolved in tetrahydrofuran (200 ml), followed by the dropwise addition of a 1M solution of boron hydride (BH$_3$) in tetrahydrofuran (80 ml) under cooling with ice. The obtained mixture was stirred at room temperature for one hour to complete a reaction. The reaction mixture was poured into a saturated aqueous solution of ammonium chloride and the obtained mixture was extracted with ethyl acetate. The organic phase was distilled to remove the solvent and the residue was subjected to silica gel column chromatography and eluted with a solvent (ethyl acetate/hexane=1:1) to give 16.7 g of t-butyl 4-(3-hydroxyethylpropyl)benzoate. This alcohol was dissolved in ether (400 ml), followed by the addition of triethylamine (4.4 ml) and methanesulfonyl chloride (9.8 ml) under cooling with ice. The obtained mixture was stirred to complete a reaction. The reaction mixture was poured into a saturated aqueous solution of ammonium chloride. The obtained mixture was extracted with ether and the organic phase was distilled to remove the solvent. Thus, a mesylate was obtained. This mesylate was dissolved in acetone (400 ml), followed by the addition of sodium iodide (40 g). The obtained mixture was heated under reflux to complete a reaction. The reaction mixture was poured into a saturated aqueous solution of ammonium chloride. The obtained mixture was extracted with ether. The organic phase was distilled to remove the solvent and the residue was subjected to silica gel column chromatography and eluted with a solvent (ether/hexane=1:15) to give 20 g of the title compound as a colorless oil (55%).

$^1$H-NMR (CDCl$_3$) δ(ppm): 0.77 (3H, t, J=7.2Hz, —CH$_2$CH$_3$), 1.58 (9H, s, t-Bu), 1.57~1.76 (2H, m, —CH$_2$CH$_3$), 2.01~2.24 (2H, m, I—CH$_2$CH$_2$CH—Ar), 2.63~3.09 (3H, m, I—CH$_2$CH$_2$CH—Ar), 7.22 (2H, d, J=8.4Hz, ArH), 7.94 (2H, d, J=8.4Hz, ArH).

PREPARATIVE EXAMPLE 120

Preparation of t-butyl 4-(3-iodo-1-methylpropyl)benzoate t-Butyl p-formylbenzoate (20 g, 97 mmol) was dissolved in dry diethyl ether (300 ml), followed by the dropwise addition of methylmagnesium bromide (3M ethereal solution, 33 ml) under cooling with ice and stirring. The obtained mixture was stirred for one hour and poured into a saturated aqueous solution of ammonium chloride, and the obtained mixture was extracted with ether. The ethereal phase was washed with water, dried and distilled to remove the solvent. The pale-yellow viscous liquid residue thus obtained was subjected to silica gel column chromatography and eluted with a solvent (ethyl acetate/hexane=1:4) to give 21.8 g of t-butyl 4-(hydroxyethyl)benzoate.

The hydroxy compound thus prepared was subjected to the same reaction as that of the Preparative Example 119 to give 8.5 g of the objective iodo compound (494).

$^1$H-NMR (CDCl$_3$) δ(ppm): 1.28 (3H, d, J=7.2Hz, -Me), 1.58 (9H, s, t-Bu), 2.06~2.13 (2H, m, I—CH$_2$CH$_2$CH—Ar), 2.87~2.98 (2H, m, I—CH$_2$CH$_2$CH—Ar), 3.05~3.12 (1H, m, I—CH$_2$CH$_2$CH—Ar), 7.25 (2H, d, J=8Hz, ArH), 7.93 (2H, d, J=8Hz, ArH).

PREPARATIVE EXAMPLE 121 t-Butyl 4-(3-bromo-1-methylpropyl)benzoate t-Butyl 4-(3-hydroxy-1-methylpropyl) benzoate was prepared in a similar manner to that of the Preparative Example 120. This compound (15.6 g, 66.6 mmol) was brominated in a similar manner to that of the Preparative Example 104 to give the objective compound. Yield: 20.5 g.

$^1$H-NMR (CDCl$_3$) δ(ppm): 1.29(3H, d, J=6.8Hz), 1.59(9H, s), 2.12(2H, dr, J=6, 8Hz, 6, 8Hz), 3.03(1H, ddq, J=6.8Hz, 6.8Hz, 6.8Hz), 3.15(1H, dr, J=10.0Hz, 6.8Hz), 3.31 (1H, dr, J=10.0Hz, 6.8Hz), 7.25(2H, d, J=8.4Hz), 7.93 (2H, d, J=8.4Hz).

PREPARATIVE EXAMPLE 122 t-Butyl 4-[3-(2-cyano-1-cyclopentanon-3-yl)-1-methylpropyl]benzoate

The bromide (7.9 g, 25 mmol) prepared in the Preparative Example 121 was converted into the corresponding objective compound in a similar manner to that of the Preparative Example 105. Yield: 1.6 g.

$^1$H-NMR (CDCl$_3$) δ(ppm): 1.20–1.85(5H, m), 1.50(OH, s), 2.16–2.58(4H, m), 2.75(1H, d, J=12.0Hz), 2.71–2.84(1H, m), 7.28(2H, d, J=8.4Hz), 7.08(2H, d. J=8.4Hz)

Mass(EI) M$^+$=341.

PREPARATIVE EXAMPLE 123 t-Butyl 4-[3-(2-cyano-3-methoxy-2-cyclopentenyl)-1-methylpropyl]benzoate

The compound (1.57 g, 4.6 mmol) prepared in the Preparative Example 122 was converted into the corresponding objective compound in a similar manner to that of the Preparative Example 106. Yield: 1.6

$^1$H-NMR (CDCl$_3$) δ(ppm): 1.00–1.76(6H, m), 1.25(1H×½, s), 1.27(1H×½, s), 1.58(9H, s), 1.97–2.09(1H, m), 2.36–2.46(2H, m), 2.68–2.85(2H, m), 3.99(3H×½, s), 4.01 (3H, ½, s), 7.22(2H×½, d, J=8.4Hz), 7.22 (2H×½, d, J=8.4H Mass(EI) M$^+$=355.

EXAMPLE 109

4-[3-(2,4-Diamino-6,7-dihydrocyclopenta[d]pyrimidin-5-yl)-1-methylpropyl]benzoic acid The compound (1.6 g, 4.5 mmol) prepared in the Preparative Example 123 was converted into the objective compound in a similar manner to that of the Example 104. Yield: 0.39 g.

$^1$H-NMR (DMSO-d$_6$) δ(ppm): 0.90–1.68(5H, m), 1.18(3H×½, d, J=6.8Hz), 1.20(3H×½, d, J=6.8Hz) 1.88–2.02(1H, m), 2.30–2.78(3H, m), 2.86–2.96(1H, m), 5.66–5.78(2H, br) 5.92–6.06(2H, br), 7.28(2H×½, d, J=8.4Hz), 7.30(2H×½, d, J=8.4Hz), 7.84(2H×½, d, J=8.4Hz), 7.85(2H×½, d, J=8.4Hz).

Mass(FAB) M+H$^+$=327.

EXAMPLE 110

N-[4-[3-(2,4-Diamino-6,7-dihydrocyclopenta[d]pyrimidin-5-yl)-1-methyl]propyl benzoyl]-L-glutamic The carboxylic acid (0.88 g, 1.2 mmol) prepared in the Example 109 was converted into the corresponding glutamic acid derivative in a similar manner to that of the Example 103. Yield: 0.21 g.

$^1$H-NMR (DMSO-d$_6$) δ(ppm): 0.90–1.70(5H, m), 1.18(3H×½, d, J=7.2Hz), 1.18 (3H×½, d, J=7.2Hz), 1.80–2.10(3H, m), 2.16–2.80(5H, m), 2.80–2.96(1H, m), 4.28–4.40(1H,m), 5.78–5.90(2H, br), 6.08–6.18(2H, br), 7.20–7.30(2H, m), 7.72–7.82(2H, m), 8.82–8.42(1H, m).

Mass (FAB) M+H$^+$=456.

PREPARATIVE EXAMPLE 124 t-Butyl 4-[2-(2-methoxycarbonyl-1-cyclopentanon-3-yl)ethyl]benzoate

The objective compound was prepared from the bromide (5.9 g, 21 mmol) prepared in the Preparative Example 104 and 2-methoxycarbonyl-2-cyclopenten-1-one (6.4 g, 41 mmol) which can be prepared by a known process in a similar manner to that of the Preparative Example 105. Yield: 0.41 g.

$^1$H-NMR (CDCl$_3$) δ(ppm): 1.46–1.60(1H, m), 1.59(9H, s), 1.70–1.82(1H, m), 1.86–1.98(1H, m), 2.22–2.52(3H, m), 2.54–2.82(3H, m), 2.90(1H, d, J=10.8Hz), 3.76(3H, s 7.22(2H, d, J=8.4Hz), 7.91 (2H, d, J=8.4Hz).

EXAMPLE 111 t-butyl 4-[2-(2-amino-3,4,6,7-tetrahydro-4-oxo-5H-cyclopenta[d]pyrimidin-5-yl)ethyl]benzoate The compound (0.4 g, 1.2 mmol) prepared in the Preparative Example 124 was converted into the objective compound in a similar manner to that of the Example 101. Yield: 0.27 g.

$^1$H-NMR (CDCl$_3$) δ(ppm): 1.58(9H, s), 1.62–1.84(2H, m), 2.12–2.28(2H, m), 2.56–2.85(4H, m), 3.07–3.17(1H, m), 5.38–5.60(2H, br), 7.22(2H, d. J=8.4Hz), 7.87(2H, d, J=8.4Hz), 11.70–12.10(1H, br)

Mass(FAB) M+H$^+$=356 mol. form. C$_{20}$H$_{25}$N$_3$O$_3$

| elem. anal. | |
|---|---|
| calculated (%) | found (%) |
| C 67.58 | C 67.48 |
| H 7.09 | H 7.12 |
| N 11.82 | N 11.81 |

EXAMPLE 112

4-[2-(2-Amino-3,4,6,7-tetrahydro-4-oxo-5H-cyclopenta-[d]pyrimidin-5-yl)ethyl]benzoic acid The compound (0.25 g, 0.7 mmol) prepared in the Example 111 was converted into the corresponding carboxylic acid in a similar manner to that of the Example 102. Yield: 0.16 g.

$^1$H-NMR (DMSO-$d_6$) δ(ppm): 1.45–1.67(2H, m), 2.00–2.18(2H, m), 2.38–2.50(1H, m), 2.52–2.72(3H, m), 2.86–2.96(1H, m), 6.24–6.42(2H, br), 7.30(2H, d, J=8.4Hz), 7.82(2H, d, J=8.4Hz), 10.40–10.60(1H, br)

Mass(FAB) M+H$^+$=300 mol. form. $C_{16}H_{17}N_3O_3 \cdot 0.5H_2O$

| elem. anal. | |
|---|---|
| calculated (%) | found (%) |
| C 62.33 | C 62.28 |
| H 5.88 | H 5.82 |
| N 13.63 | N 13.63 |

EXAMPLE 113

N-[4-[2-(2-Amino-3,4,6,7-tetrahydro-4-oxo-5H-cyclopenta[d]pyrimidin-5-yl)ethylbenzoyl]-L-glutamic The carboxylic acid (0.15 g, 0.5 mmol) prepared in the Example 112 was converted into the corresponding glutamic acid derivative in a similar manner to that of the Example 103. Yield: 0.09 g.

$^1$H-NMR (DMSO-$d_6$) δ(ppm): 1.44–1.70(2H, m), 1.86–2.20(4H, m), 2.28–2.35(2H, m). 2.35–2.72(4H, m). 2.85–2.96(1H, m), 4.30–4.42(1H, m), 6.25–6.40(2H, br), 7.28(2H, d, J=8.4Hz), 7.77(2H, d, J=8.4Hz). 8.40–8.50(1H, m), 10.40–10.60(1H, br).

PREPARATIVE EXAMPLE 125

Ethyl 4-(ethoxycarbonylmethyloxy)benzoate

Sodium hydride (min. 604 paraffinic dispersion, 2.95 g, about 74 mmol) was washed with anhydrous hexane in a nitrogen stream and suspended in anhydrous dimethylformamide. The obtained suspension was stirred under cooling with ice, followed by the dropwise addition of a solution of ethyl 4-hydroxybenzoate (11.2 g, 67 mmol) in dimethylformamide. The obtained mixture was stirred at room temperature for 30 minutes and cooled with ice again, followed by the dropwise addition of a solution of ethyl bromoacetate (12.9 g, 77 mmol) in anhydrous dimethylformamide. The obtained mixture was stirred at room temperature to complete a reaction. The reaction mixture was filtered to remove insolubles and the filtrate was concentrated under a reduced pressure. The residue was dissolved in diethyl ether and the obtained solution was washed with an aqueous solution of sodium hydrogencarbonate and an aqueous solution of common salt, dried and distilled to remove the solvent. The residue was purified by silica gel column chromatography. Yield: 16.8 g.

$^1$H-NMR (CDCl$_3$) δ(ppm): 1.29(3H, t, J=7.2Hz), 1.37(3H, t, J=7.2Hz), 4.28(2Ho q, J=7.2Hz), 4.34 (2H, q, J=7.2Hz), 4.67(2H, s), 6.92(2H, d, J=8.8Hz), 8.00(2H, d, J=8.8Hz).

PREPARATIVE EXAMPLE 126

Ethyl 4-(2-hydroxyethyloxy)benzoate

The ester (16.8 g, 67 mmol) prepared in the Preparative Example 125 was converted into the objective hydroxyl compound in a similar manner to that of the Preparative Example 109. Yield: 13.7 g.

$^1$H-NMR (CDCl$_3$) δ(ppm): 1.38(3H, t, J=7.2Hz), 1.74–1.88(1H, br), 4.00(2H, t, J=4.4Hz), 4.14(2H, t, J=4.4Hz), 4.35(2H, q, J=7.2Hz), 6.94(2H, d, J=9.2Hz), 8.00(2H, d, J=9.2Hz).

PREPARATIVE EXAMPLE 127

Ethyl 4-(2-bromoethyloxy)benzoate

The hydroxyl compound (13.7 g, 65 mmol) prepared in the Preparative Example 126 was subjected to the same reaction as that of the Preparative Example 110 to give the objective bromo compound as a colorless solid. Yield: 15.8 g.

$^1$H-NMR (CDCl$_3$) δ(ppm): 1.38(3H, t, J=6.8Hz), 3.66(2H, t, J=6.4Hz), 4.34 (2H, t, J=6.4Hz), 4.35(2H, q, J=6.8Hz), 6.92(2H, d, J=8.8Hz), 8.00(2H, d, J=8.8Hz)

Mass(FAB) M+H$^+$=273, 275 mol. form. $C_{11}H_{13}O_3Br$

| elem. anal. | |
|---|---|
| calculated (%) | found (%) |
| C 48.37 | C 48.15 |
| H 4.80 | H 4.71 |

PREPARATIVE EXAMPLE 128

Ethyl 4-[2-(2-cyano-1-cyclopentanon-3-yl)ethyloxy]benzoate

The bromide (7.7 g, 28 mmol) prepared in the Preparative Example 127 was converted into the objective compound in a similar manner to that of the Preparative Example 105. Yield: 1.1 g.

$^1$H-NMR (CDCl$_3$) δ(ppm) 1.38(3H, t, J=7.2Hz), 1.50–1.78(1H, m), 2.00–2.80(7H, m), 3.00(1H, d, J=12.0Hz), 4.20(2H, t, J=6.0Hz), 4.35(2H, q, J=7.2Hz), 6.92(2H, d, J=9.2Hz), 8.00(2H, d, J=9.2Hz).

PREPARATIVE EXAMPLE 129 t-Butyl 4-[2-(2-cyano-3-methoxy-2-cyclopentenyl)ethyloxy]benzoate

The compound (1.1 g, 3.7 mmol) prepared in the Preparative Example 128 was converted into the objective compound in a similar manner to that of the Preparative Example 106. Yield: 0.78 g.

$^1$H-NMR (CDCl$_3$) δ(ppm) 1.38(3H, t. J=7.2Hz), 1.60–1.74(1H, m), 1.76–1.90(1H, m), 2.12–2.32(2H, m), 2.46–2.54(2H, m), 3.06–4.08(1H, m), 4.12(2H, t, J=6.0Hz), 4.34(2H, q, J=7.2Hz), 6.90(2H, d, J=8.8Hz), 7.99(2H, d, J=8.8Hz)

Mass(FAB) M+H$^+$=316.

EXAMPLE 114

4-[2-(2,4-Diamino-6,7-dihydro-5H-cyclopenta[d] pyrimidin-5-yl)ethyloxy]benzoic acid The compound (0.78 g, 2.5 mmol) prepared in the Preparative Example 129 was converted into the objective compound in a similar manner to that of the Example 104. Yield: 0.37 g.

$^1$H-NMR (DMSO-$d_6$) δ(ppm): 1.64–1.85(2H, m), 1.94–2.08(2H, m), 2.32–2.45(1H, m), 2.58–2.72(1H, m), 3.00–3.12(1H, m), 4.04(2H, t, J=7.2Hz), 5.60–5.67(2H, br), 5.97–6.05(2H, br), 6.94(2H, d, J=8.8Hz), 7.84(2H, d, J=8.8Hz)

Mass(FAB) M+H$^+$=315.

EXAMPLE 115

N-[4-[2-(2,4-Diamino-6,7-dihydro-5H-cyclopenta[d] pyrimidin-5-yl) ethyloxy]benzoyl]-L-glutamic acid The carboxylic acid (0.48 g, 1.5 mmol) prepared in the Preparative Example 114 was converted into the objective compound in a similar manner to that of the Example 103.

$^1$H-NMR (DMSO-$d_6$) δ(ppm): 1.66–2.10(6H, m), 2.27–2.35(2H, m), 2.36–2.50(1H, m), 2.62–2.74(1H, m), 3.02–3.13(1H, m), 4.05(2H, t, J=6.8Hz), 4.29–4.38(1H, m), 5.81–5.98(2H, br), 6.18–6.30(2H, br), 6.97(2H, d, J=8.8Hz), 7.82(2H, d, J=8.8Hz), 8.34(1H, d, J=7.2Hz)

Mass(FAB) M+H$^+$=444.

PREPARATIVE EXAMPLE 130 t-Butyl 4-(1-fluoro-3-butenyl)benzoate

A 1.0M solution (200 ml, 200 ml) of allylmagnesium bromide in diethyl ether was dropped into a solution of t-butyl 4-formylbenzoate (30.9 g, 150 mmol) in anhydrous tetrahydrofuran, while stirring the latter under cooling with ice in a nitrogen stream. After the completion of the dropping, the obtained mixture was further stirred for 30 minutes, followed by the addition of 220 ml of 1N hydrochloric acid cooled with ice. The obtained mixture was vigorously stirred. The aqueous layer was further extracted with diethyl ether. The organic layers were combined, washed with an aqueous solution of common salt, dried and concentrated. The residue was purified by silica gel column chromatography to give t-butyl 4-(1-hydroxy-3-butenyl)benzoate. Yield: 8.2 g.

The hydroxyl compound (12 g, 48.3 mmol) prepared above was dissolved in anhydrous methylene chloride. The obtained solution was dropped into a solution of diethylaminosulfur trifluoride (9.0 g, 56 mmol) in anhydrous methylene chloride, which was kept in a dry ice-acetone bath, in a nitrogen atmosphere. After the completion of the dropping, the obtained mixture was stirred at room temperature, followed by the addition of a phosphate buffer (pH: 7). The organic layer was recovered, washed with an aqueous solution of common salt, dried and distilled to remove the solvent. The residue was purified by silica gel column chromatography to give the objective compound. Yield: 8.5 g.

$^1$H-NMR (CDCl$_3$) δ(ppm): 1.60(9H, s), 2.50–2.78(2H, m), 5.10–5.17(2H, m), 5.53(1H, ddd, J=5.2Hz, 7.6Hz, J$_{HF}$=47.6Hz), 5.72–5.83(2H, m), 7.37 (2H, d, J=8.0Hz), 7.99(2H, d, J=8.0Hz)

IR (neat) ν(cm$^{-1}$):2980, 1715, 1291, 1166, 1118.

PREPARATIVE EXAMPLE 131 t-Butyl 4-(1-fluoro-3-hydroxypropyl)benzoate

The fluoro compound (8.5 g, 34 mmol) prepared in the Preparative Example 130, N-methylmorpholine N-oxide (5.0 g, 44 mmol) and osmium tetraoxide (1 g/100 cc, t-BuOH, 8.6 ml, 33.7×$\frac{1}{100}$ mmol) were dissolved in an acetone/water mixture. The obtained solution was stirred at room temperature to complete a reaction. The reaction mixture was filtered to remove insolubles and the filtrate was distilled to remove the acetone. 75 ml of 1N hydrochloric acid was added to the residue and the obtained mixture was extracted with ethyl acetate. The organic layers were combined, washed with an aqueous solution of common salt, dried and evaporated to dryness under a reduced pressure to give t-butyl 4-(1-fluoro-3,4-dihydroxybutyl)benzoate.

The diol prepared above was dissolved in diethyl ether, followed by the gradual addition of an aqueous solution of sodium periodate (71 g, 51 mmol) under stirring and cooling with ice. After the completion of the dropping, the obtained mixture was further stirred for 2 hours. The organic layer was recovered and the aqueous layer was further extracted with diethyl ether. The organic layers were combined, washed with an aqueous solution of common salt, dried and evaporated to dryness under a reduced pressure to give t-butyl 4-(1-fluoro-3-oxypropyl)benzoate.

The aldehyde prepared above was dissolved in tetrahydrofuran and sodium borohydride (1.9 g, 51 mmol) was gradually added to the resulting solution while stirring the solution under cooling with ice. The obtained mixture was stirred at room temperature to complete a reaction, followed by the addition of diethyl ether and ice-water. The organic layer was recovered and the aqueous layer was further extracted with diethyl ether. The organic layers were combined, washed with an aqueous solution of common salt, dried and distilled to remove the solvent. The residue was purified by silica gel column chromatography to give the objective compound. Yield: 6.4 g.

$^1$H-NMR (CDCl$_3$) δ(ppm): 1.49–1.55(1H, m), 1.60(9H, s), 1.96–2.28(2H, m), 3.74–3.84(1H, m), 3.84–3.95(1H, m), 5.74(1H, ddd, J=4, 0Hz, 8.8Hz, J$_{HF}$=48.0Hz), 7.39(2H, d, J=8.0Hz), 8.00(2H, d, J=8.0Hz).

PREPARATIVE EXAMPLE 132 t-Butyl 4-(3-bromo-1-fluoropropyl)benzoate

The hydroxyl compound (6.4 g, 25 mmol) prepared in the Preparative Example 131 was subjected to the same reaction as that of the Preparative Example 110 to give 7.4 g of the objective bromo compound.

$^1$H-NMR (CDCl$_3$) δ(ppm): 1.60(9H, s), 2.19–2.39(1H, m), 2.41–2.57(1H, m), 3.40–3.47(1H, m), 3.54–3.62(1H, m), 5.72(1H, ddd, J=4.0Hz, 9.2Hz, J$_{HF}$=48.0Hz), 7.39(2H, d, J=8.4Hz), 8.01 (2H, d, J=8.4Hz)

IR (neat) ν(cm$^{-1}$) ;2979, 1715, 1291, 1166, 1118.

PREPARATIVE EXAMPLE 133 t-Butyl 4-[3-(2-cyano-1-cyclopentenon-3-yl)-1-fluoropropyl] benzoate

The bromide (5.2 g, 16 mmol) prepared in the Preparative Example 132 was converted into the objective compound in a similar manner to that of the Preparative Example 105. Yield 0.8 g.

PREPARATIVE EXAMPLE 134 t-Butyl 4-[3-(2-cyano-3-methoxy-2-cyclopentenyl)-1-fluoropropyl]benzoate

The compound (0.8 g, 2.3 mmol) prepared in the Preparative Example 133 was converted into the objective compound in a similar manner to that of the Preparative Example 106. Yield: 0.57 g.

$^1$H-NMR (CDCl$_3$) δ(ppm): 1.34–1.66(2H, m), 1.60(9H, s), 1.70–2.16(4H, m), 2.42–2.52(2H, m), 2.80–2.98(1H, m), 4.03(3H×½, s), 4.04(3H×½, s), 5.51 (1H, ddd, J=4.8Hz, 7.6Hz, J$_{HF}$=47.6Hz), 7.36(2H×½, d, J=8.0Hz), 7.37(2H×½, d, J=8.0Hz), 7.99(2H, d, J=8.0Hz)

IR (neat) ν(cm$^{-1}$); 2978, 2947, 2203, 1712, 1629, 1294, 1166, 1119.

EXAMPLE 116 t-Butyl 4-[3-(2,4-diamino-6,7-dihydro-5H-cyclopenta-[d]pyrimidin-5-yl)-1-fluoropropyl]benzoate The compound (0.57 g, 1.6 mmol) prepared in the Preparative Example 134 was converted into the objective compound in a similar manner to that of the Example 101. Yield: 0.4 g.

$^1$H-NMR (CDCl$_3$) δ(ppm): 1.38–1.66(1H, m), 1.59(9H, s), 1.68–2.04(4H, m), 2.11–2.25(1H, m), 2.57–2.68(1H, m), 2.73–2.85(1H, m), 3.00–3.12(1H, m), 4.46–4.59(2H, br), 4.59–4.72(2H, br). 5.40–5.64(1H, m), 7.34(2H, d, J=8.4Hz), 7.99(2H, d, J=8.4Hz).

EXAMPLE 117

4-[3-(2,4-Diamino-6,7-dihydro-5H-Cyclopenta[d]pyrimidin-5-yl)-1-fluoropropyl]benzoic acid The compound (0.35 g. 0.91 mmol) prepared in the Example 116 was converted into the corresponding carboxylic acid in a similar manner to that of the Example 102. Yield: 0. 26 g.

EXAMPLE 118

N-[4-[3-(2,4-Diamino-6,7-dihydro-5H-cyclopenta[d]pyrimidin-5-yl)-1-fluoropropyl]benzoyl]-L-glutamic acid The carboxylic acid (0.26 g. 0.78 mmol) prepared in the Example 117 was converted into the corresponding glutamic acid derivative in a similar manner to that of the Example 103. Yield: 0.085 g.

$^1$H-NMR (DMSO-d$_6$) δ(ppm): 1.10–2.15(8H, m). 2.20–2.70(2H, m), 2.32(2H, t, J=7.6Hz), 2.90–3.05(1H, m), 4.32–4.40(1H, m), 5.45–5.68(1H, m). 6.00–6.30(2H, br), 6.30–6.60(2H, br), 7.41 (2H, d, J=8.0Hz), 7.87(2H, d, J=8.0Hz), 8.55(1H, d, J=7.2Hz)

Mass(FAB) M+H$^+$=460 mol. form. C$_{22}$H$_{26}$N$_5$O$_5$F·1H$_2$O

| elem. anal. | | |
|---|---|---|
| | calculated (%) | found (%) |
| | C 55.34 | C 55.05 |
| | H 5.91 | H 5.80 |
| | H 14.67 | H 14.54 |

PREPARATIVE EXAMPLE 135

2-(2-Cyano-1-cyclopentanon-3-yl)ethylbenzoate

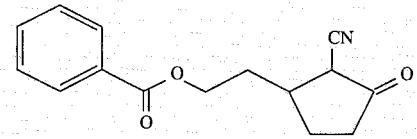

2-Bromoethyl benzoate (7.9 g, 34 mmol) was converted into the corresponding objective compound in a similar manner to that of the Example 105. yield: 2.6 g.

PREPARATIVE EXAMPLE 136

2-(2-Cyano-3-methoxy-2-cyclopentenyl)ethylbenzoate

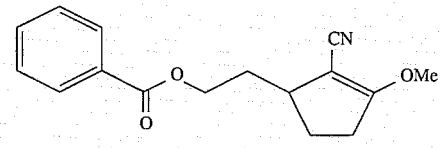

The compound (2.6 g, 10 mmol) prepared in the Preparative Example 135 was converted into the corresponding objective compound in a similar manner to that of the Preparative Example 106. yield: 1.4 g.

$^1$H-NMR (CDCl$_3$) δ(ppm): 1.61~1.73 (1H, m), 1.78~1.86 (1H, m), 2.13~2.82 (2H, m), 2.46~2.56 (2H, m), 3.01~3.12 (1H, m), 4.05 (3H, s), 4.41 (2H, t, J=6.4Hz), 7.40~7.48 (2H, m), 7.58~7.60 (1H, m), 8.01~8.07 (2H, m).

PREPARATIVE EXAMPLE 137

1-Cyano-5-(2-hydroxyethyl)-2-methoxy-1-cyclopentene

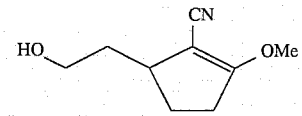

6 ml of 1N sodium hydroxide was added to a solution of the compound (1.4 g, 5 mmol) prepared in the Preparative Example 136 in methanol. The obtained mixture was stirred at room temperature to complete a reaction. The reaction mixture was distilled to remove the methanol and the residue was dissolved in ethyl acetate. The obtained solution was washed with an aqueous solution of sodium hydrogencarbonate and an aqueous solution of common salt, dried over magnesium sulfate, and distilled to remove the solvent, thus obtaining the objective compound. yield: 0.82 g.

$^1$H-NMR (CDCl$_3$) δ(ppm): 1.50~1.70 (3H, m), 1.96~2.06 (1H, m), 2.10~2.20 (1H, m), 2.42~2.57 (2H, m), 2.98~3.07 (1H, m), 3.69~3.84 (2H, m), 4.05 (3H, s).

PREPARATIVE EXAMPLE 138

1-Cyano-5-(2-iodoethyl)-2-methoxy-1-cyclopentene

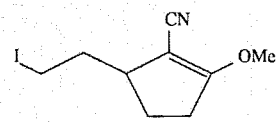

The alcohol (0.82 g, 4.9 mmol) prepared in the Preparative Example 137 was converted into the corresponding iodo compound according to the same procedure as that of the Preparative Example 104 except that sodium iodide was used instead of the lithium bromide. yield: 1.3 g.

$^1$H-NMR (CDCl$_3$) δ(ppm): 1.44~1.60 (1H, m), 1.78~1.90 (1H, m), 2.08~2.20 (1H, m), 2.23~2.34 (1H, m), 2.45~2.53 (2H, m), 2.93~3.03 (1H, m), 3.12~3.20 (1H, m), 3.23~3.32 (1H, m), 4.05 (3H, s).

PREPARATIVE EXAMPLE 139

Ethyl 4-[N-benzoyl-N-[2-(2-cyano-3-methoxy-2-cyclopentenyl)ethyl]amino]benzoate

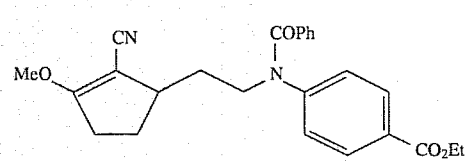

Sodium hydride (min 60% paraffinic dispersion, 0.14 g, 3.5 mmol) was washed with anhydrous hexane in a nitrogen stream and suspended in anhydrous dimethylformamide, followed by the addition of ethyl 4-benzoylaminobenzoate. The obtained mixture was stirred at room temperature for 30 minutes, followed by the addition of a solution of the iodo compound (0.72 g, 3.2 mmol) prepared in the Preparative Example 138 in anhydrous dimethylformamide. The obtained mixture was stirred at 60° C. for one hour and distilled to remove the solvent. The residue was dissolved in ethyl acetate and the obtained solution was washed with an aqueous solution of common salt, dried and subjected to silica gel column chromatography to give the objective compound. yield: 0.62 g.

$^1$H-NMR (CDCl$_3$) δ(ppm): 1.36(3H, t, J=7.2Hz), 1.60–1.75(2H, m), 2.00–2.11 (1H, m), 2.14–2.25(1H, m), 2.47–2.54(2H, m), 2.85–2.96(1H, m), 4.39–4.42(2H, m), 4.02(3H, s), 4.33(2H, q, J=7.2Hz), 7.08(2H, d, J=8.8Hz), 7.28–7.60(5H, m 7.90(2H, d, J=8.8Hz)

IR (neat) ν(cm$^{-1}$):2983, 2946, 2203, 1716, 1647, 1604, 1275, 1104.

EXAMPLE 119

4-[N-[2-(2,4-Diamino-8,7-dihydro-5H-cyclopenta-[d]pyrimidin-5-yl)ethyl]-N-benzoylamino]benzoic acid

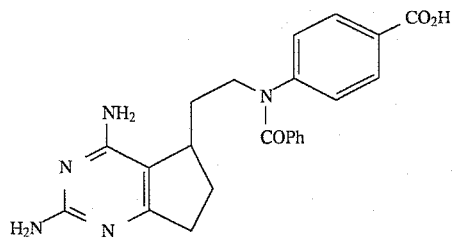

The compound (0.61 g, 1.45 mmol) prepared in the Preparative Example 139 was converted into the corresponding objective compound in a similar manner to that of the Example 104. yield: 0.11 g.

NMR (DMSO-d$_6$) δ(ppm) 1.42–1.54(1H, m), 1.63–1.85(2H, m), 1.91–2.04(1H, m), 2.32–2.67(2H, m), 2.90–3.00(1H, m), 3.80–3.96(2H, m), 5.77–5.87(2H, br), 6.07–6.15(2H, br), 7.15–7.28(7H, m), 7.75(2H, d, J=8.4Hz).

EXAMPLE 120

4-[N-[2-(2,4-Diamino-6,7-dihydro-5H-cyclopenta-[d]pyrimidin-5-yl)ethyl]]aminobenzoic acid

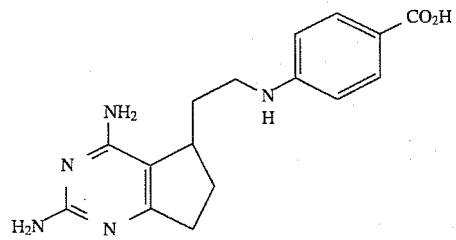

The carboxylic acid (0.11 g, 0.26 mmol) prepared in the Example 119 and lithium hydroxide monohydrate (0.11 g, 2.6 mmol) were dissolved in distilled water and the obtained solution was stirred under heating at 80° C. to complete a reaction. The reaction mixture was acidified by the addition of 1N hydrochloric acid, followed by the addition of chloroform. The obtained mixture was vigorously stirred and filtered to recover precipitates. The precipitates were washed with chloroform and reprecipitated from 1N sodium hydroxide and 1N hydrochloric acid to give the objective compound. yield: 70 mg.

NMR (DMSO-d$_6$) δ(ppm): 1.39–1.51 (1H, m), 1.71–1.92(2H, m), 1.94–2.07(1H, m), 2.40–2.50(1H, m), 2.63–2.74(1H, m), 2.98–3.15(3H, m), 5.88–6.03(2H, br), 6.37(1H, t, J=4.8Hz), 6.34–6.50(2H, br), 6.54(2H, d, J=8.4Hz), 7.64(2H, d, J=8.4Hz).

EXAMPLE 121

N-[4-[N'-[2-(2,4-Diamino-6,7-dihydro-5H-cyclopenta[d]pyrimidin-5-yl)ethyl]]amino]benzoyl-L-glutamic acid

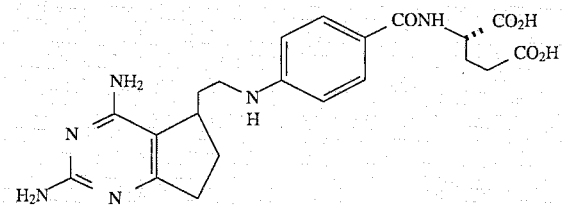

The carboxylic acid (65 mg, 0.21 mmol) prepared in the Example 120 was converted into the corresponding objective compound in a similar manner to that of the Example 103. yield: 10 mg.

NMR (DMSO-$d_6$) δ(ppm): 1.36–1.51 (1H, m), 1.69–2.07(5H, m), 2.21–2.52(3H, m), 2.59–2.72(1H, m), 3.00–3.16(3H, m), 4.26–4.35(1H, m), 5.75–5.90(2H, br). 6.15(1H, t, J=4.8Hz), 6.15–6.35(2H, br), 6.34(2H, d, J=8.4Hz), 7.64(2H, d, J=8.4Hz), 8.02(1H, d, J=7.2Hz)

Mass (FAB) M+H$^+$=443.

What we claimed is:

1. A pyrrolo[3,2-d]pyrimidine derivative represented by the following formula (1) or a pharmacologically acceptable salt thereof:

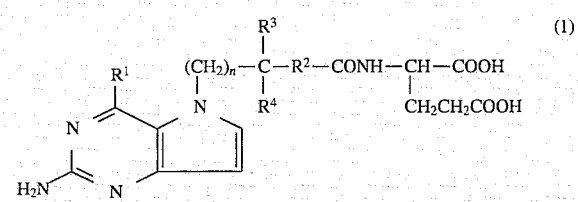

wherein R$^1$ represents a hydroxyl or amino group; R$^2$ represents a phenylene group or a group represented by the formula:

wherein X represents a sulfur or oxygen atom; R$^3$ and R$^4$ may be the same or different from each other and each represents a hydrogen atom or a straight-chain or branched hydrocarbon group having 1 to 6 carbon atoms, or alternatively R$^3$ and R$^4$ may be united to form an alkylidene group, and n is an integer of 1 to 3.

2. A compound having the formula

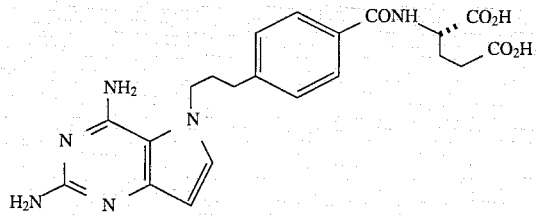

or a pharmaceutically acceptable salt thereof.

3. A compound having the formula

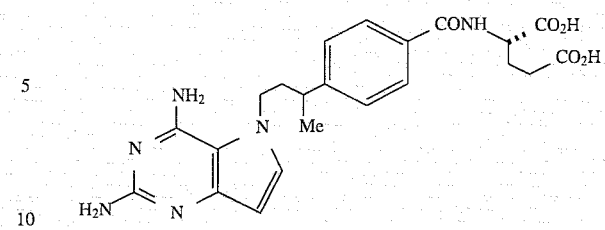

or a pharmaceutically acceptable salt thereof.

4. The pyrrolo[3,2-d]pyrimidine derivative or a pharmacologically acceptable salt thereof as set forth in claim 1, wherein R$^2$ is a thiophene residue.

5. The pyrrolo[3,2-d]pyrimidine derivative or a pharmacologically acceptable salt thereof as set forth in claim 1, wherein R$^3$ and R$^4$ are the same or different from each other and are each a hydrogen atom or a lower alkyl, lower alkenyl or lower alkynyl group.

6. The pyrrolo[3,2-d]pyrimidine derivative or a pharmacologically acceptable salt thereof as set forth in claim 1, wherein n is 2.

7. The pyrrolo[3,2-d]pyrimidine derivative or a pharmacologically acceptable salt thereof as set forth in claim 1, wherein R$^2$ is a phenylene group.

8. A drug composition comprising an effective antitumor amount of the pyrimidine derivative or pharmacologically acceptable salt thereof as set forth in claim 1 and a pharmaceutically acceptable carrier.

9. A method for treating a patient with leukemia, which comprises administratering an effective amount of the pyrimidine derivative or pharmacologically acceptable salt thereof as set forth in claim 1 to the patient.

10. A compound having the formula

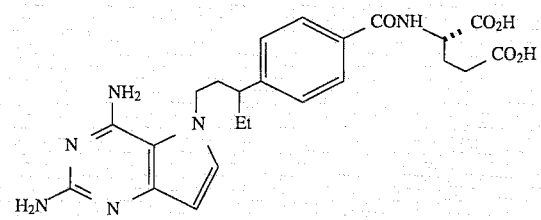

or a pharmaceutically acceptable salt thereof.

11. A compound having the formula

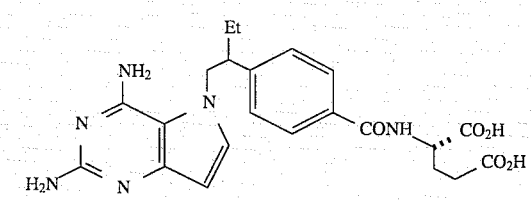

or a pharmaceutically acceptable salt thereof.

12. The compound N-[5-[3-(2,4-Diaminopyrrolo[3,2-d]pyrimidin-5 -yl)propyl] thienoyl]-L-glutamate;

or a pharmaceutically acceptable salt thereof.

13. A compound having the formula

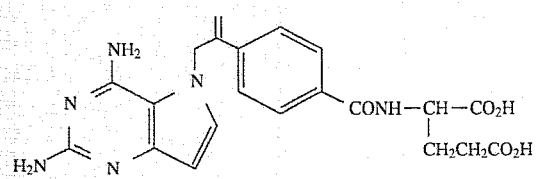

or a pharmaceutically acceptable salt thereof.

14. A pharmaceutical composition which comprises a compound according to claim 2 and a pharmaceutically acceptable carrier.

15. A pharmaceutical composition which comprises a compound according to claim 3 and a pharmaceutically acceptable carrier.

16. A pharmaceutical composition which comprises a compound according to claim 10 and a pharmaceutically acceptable carrier.

17. A pharmaceutical composition which comprises a compound according to claim 11 and a pharmaceutically acceptable carrier.

18. A pharmaceutical composition which comprises a compound according to claim 12 and a pharmaceutically acceptable carrier.

19. A pharmaceutical composition which comprises a compound according to claim 13 and a pharmaceutically acceptable carrier.

20. A method for treating choriocarcinoma which comprises administering to a patient in need thereof, an antitumor effective amount of a compound according to claim 1.

21. A method for treating epidermal carcinoma of the head which comprises administering to a patient in need thereof, an antitumor effective amount of a compound according to claim 1.

22. A method for treating epidermal carcinoma of the neck which comprises administering to a patient in need thereof, an antitumor effective amount of a compound according to claim 1.

23. A method for treating squamocellular lung cancer which comprises administering to a patient in need thereof, an antitumor effective amount of a compound according to claim 1.

24. A method for treating parvicellular lung cancer which comprises administering to a patient in need thereof, an antitumor effective amount of a compound according to claim 1.

25. A method for treating lymphosarcoma which comprises administering to a patient in need thereof, an antitumor effective amount of a compound according to claim 1.

26. The pyrrolo[3,2-d]pyrimidine derivative or a pharmacologically acceptable salt thereof as set forth in claim 1, wherein $R^1$ is an amino group.

* * * * *